(12) United States Patent
Law et al.

(10) Patent No.: US 8,663,642 B2
(45) Date of Patent: *Mar. 4, 2014

(54) ANTI-CD70 ANTIBODY-DRUG CONJUGATES AND THEIR USE FOR THE TREATMENT AND PREVENTION OF CANCER AND IMMUNE DISORDERS

(75) Inventors: Che-Leung Law, Shoreline, WA (US); Julie McEarchern, Mill Creek, WA (US); Jonathan G. Drachman, Seattle, WA (US)

(73) Assignee: Seattle Genetics, Inc., Bothell, WA (US)

( * ) Notice: Subject to any disclaimer, the term of this patent is extended or adjusted under 35 U.S.C. 154(b) by 471 days.

This patent is subject to a terminal disclaimer.

(21) Appl. No.: 12/891,716

(22) Filed: Sep. 27, 2010

(65) Prior Publication Data

US 2011/0150908 A1 Jun. 23, 2011

Related U.S. Application Data

(63) Continuation of application No. 11/735,376, filed on Apr. 13, 2007, now abandoned, which is a continuation-in-part of application No. 10/546,304, filed as application No. PCT/US2004/005247 on Feb. 20, 2004, now Pat. No. 7,662,387, and a continuation-in-part of application No. PCT/US2006/015145, filed on Apr. 19, 2006.

(60) Provisional application No. 60/449,055, filed on Feb. 20, 2003, provisional application No. 60/792,127, filed on Apr. 13, 2006, provisional application No. 60/673,070, filed on Apr. 19, 2005.

(51) Int. Cl.
*A61K 39/00* (2006.01)

(52) U.S. Cl.
USPC .................. 424/178.1; 424/179.1; 424/181.1; 424/182.1; 424/183.1

(58) Field of Classification Search
None
See application file for complete search history.

(56) References Cited

U.S. PATENT DOCUMENTS

| | | | |
|---|---|---|---|
| 5,573,924 A | 11/1996 | Beckmann et al. | |
| 6,214,345 B1 | 4/2001 | Firestone et al. | |
| 6,342,219 B1 | 1/2002 | Thorpe et al. | |
| 6,884,869 B2 | 4/2005 | Senter et al. | |
| 7,261,892 B2 | 8/2007 | Terrett et al. | |
| 7,491,390 B2 | 2/2009 | Law et al. | |
| 7,498,298 B2 | 3/2009 | Doronina et al. | |
| 7,615,211 B2 | 11/2009 | Swamy et al. | |
| 7,662,387 B2 * | 2/2010 | Law et al. | 424/178.1 |
| 7,745,394 B2 | 6/2010 | Doronina et al. | |
| 8,067,546 B2 * | 11/2011 | McDonagh et al. | 530/387.3 |
| 2002/0168360 A1 | 11/2002 | Dingivan et al. | |
| 2003/0083263 A1 | 5/2003 | Doronina et al. | |
| 2003/0096743 A1 | 5/2003 | Senter et al. | |
| 2003/0105000 A1 * | 6/2003 | Pero et al. | 514/12 |
| 2003/0130189 A1 | 7/2003 | Senter et al. | |
| 2004/0157782 A1 | 8/2004 | Doronina et al. | |
| 2004/0180002 A1 | 9/2004 | Young | |
| 2005/0113308 A1 | 5/2005 | Senter et al. | |
| 2005/0118656 A1 | 6/2005 | Terrett | |
| 2005/0123547 A1 | 6/2005 | Terrett | |
| 2005/0191299 A1 | 9/2005 | Swamy et al. | |
| 2005/0238649 A1 | 10/2005 | Doronina et al. | |
| 2006/0074008 A1 | 4/2006 | Senter et al. | |
| 2006/0083736 A1 | 4/2006 | Law et al. | |
| 2006/0233794 A1 | 10/2006 | Law et al. | |
| 2007/0292422 A1 | 12/2007 | Law et al. | |
| 2008/0138341 A1 | 6/2008 | Law et al. | |
| 2008/0138343 A1 | 6/2008 | Law et al. | |
| 2008/0226657 A1 | 9/2008 | Doronina et al. | |
| 2008/0248051 A1 | 10/2008 | Doronina et al. | |
| 2008/0248053 A1 | 10/2008 | Doronina et al. | |
| 2009/0047296 A1 | 2/2009 | Doronina et al. | |
| 2009/0074772 A1 | 3/2009 | Law et al. | |
| 2009/0148942 A1 | 6/2009 | McDonagh et al. | |
| 2009/0232806 A1 | 9/2009 | Law et al. | |
| 2010/0183636 A1 | 7/2010 | Law et al. | |

FOREIGN PATENT DOCUMENTS

| | | |
|---|---|---|
| EP | 1 594 542 A2 | 9/2004 |
| EP | 1 799 262 A2 | 4/2006 |
| EP | 1 871 418 A2 | 10/2006 |
| WO | WO01/94629 A2 | 12/2001 |
| WO | WO02/088172 A2 | 11/2002 |
| WO | WO03/026577 A2 | 4/2003 |
| WO | WO03/046581 A2 | 6/2003 |
| WO | WO2004/010957 A2 | 2/2004 |
| WO | WO2004/073656 A2 | 9/2004 |
| WO | WO2004/104045 A1 | 12/2004 |
| WO | WO2005/081711 A2 | 9/2005 |
| WO | WO2006/044643 A2 | 4/2006 |
| WO | WO2006/113909 A2 | 10/2006 |
| WO | WO2007/038637 A2 | 4/2007 |
| WO | WO2008/074004 A2 | 6/2008 |

OTHER PUBLICATIONS

Janeway et al. (Immunobiology 5, 2001, p. 100-101).*
Cohen (Int J Radiat. Oncol. Biol. Phys. 1987, 13:251-8).*
McEarchern et al. (Blood, Meeting Info. 47th Annual Meeting of Amer. Soc. Hematology Nov. 16, 2005, 106 (11, pt. 1): 456A).*
Adam, et al. "CD70 (TNFSF7) is expressed at high prevalence in renal cell carcinomas and is rapidly internalised on antibody binding" *British J. of Cancer.* 95:298-306 (2006).
Agathanggelou et al., "Expression of immune regulatory molecules in Epstein-Barr virus-associated nasopharyngeal carcinomas with prominent lymphoid stroma. Evidence for a functional interaction between epithelial tumor cells and infiltrating lymphoid cells", *Am J. Pathol.*, 147(4):1152-1160 (1995).

(Continued)

*Primary Examiner* — Peter J Reddig
(74) *Attorney, Agent, or Firm* — Alston & Bird LLP

(57) ABSTRACT

Disclosed are anti-CD70 antibodies and derivatives thereof conjugated to cytotoxic, immunosuppressive, or other therapeutic agents, as well as pharmaceutical compositions and kits comprising the antibody- and antibody derivative-drug conjugates. Also disclosed are methods, for the treatment of CD70-expressing cancers and immunological disorders, comprising administering to a subject the disclosed pharmaceutical compositions.

21 Claims, 29 Drawing Sheets

(56) References Cited

OTHER PUBLICATIONS

Agematsu et al., "B cell subpopulations separated by CD27 and crucial collaboration of CD27+ B cells and helper T cells in immunoglobulin production," *Eur. J. Immunol.*, 27(8):2073-2079 (1997).

Agematsu et al., "Generation of plasma cells from peripheral blood memory B cells: synergistic effect of interleukin-10 and CD27/CD70 interaction," *Blood*, 91(1):173-180 (1998).

Akiba et al., "Critical contribution of OX40 ligand to T helper cell type 2 differentiation in experimental leishmaniasis", *J. Exp. Med.*, 191(2):375-380 (2000).

Baert, et al., "Influence of Immunogenicity on the Long-Term Efficacy of Infliximab in Crohn's Disease", *N. Engl. J. Med.*, 348(7):601-608 (2003).

Bahler et al., "Antigen selection in human lymphomagenesis", *Cancer Res.*, 52(19 Suppl.):5547s-5551s (1992).

Bahler et al., "Clonal evolution of a follicular lymphoma: evidence for antigen selection," *PNAS*, 89(15):6770-6774 (1992).

Bowman et al., "The cloning of CD70 and its identification as the ligand for CD27", *J. Immunol.*, 152(4):1756-1761 (1994).

Brugnoni et al., "CD70 expression on T-cell subpopulations: study of normal individuals and patients with chronic immune activation", *Immunol. Lett.*, 55(2):99-104 (1997).

Burgess et al., "Possible dissociation of the heparin-binding and mitogenic activities of heparin-binding (acidic fibroblast) growth factor-1 from its receptor-binding activities by site-directed mutagenesis of a single lysine residue", *J. Cell Biol.* 111:2129-2138 (1990).

Carter, P., "Improving the Efficacy of Antibody-Based Cancer Therapies", *Nature Reviews*, (1):118-129 (2001).

Casset, et al., "A peptide mimetic of an anti-CD4 monoclonal antibody of rational design", *Biochem, Biophys. Res.*, 307:198-205 (2003).

Chen et al., "Enhancement and destruction of antibody function by somatic mutation: unequal occurrence is controlled by V gene combinatorial associations", EMBO 14 (12):2784-2794, 1995.

Chen et al., "Selection and Analysis of an Optimized Anti-VEGF Antibody: Crystal Structure of an Affinity-matured Fab in Complex with Antigen", *J. Mol. Biol.* 5:293(4):865-81 (1999).

Coleman, PM., "Effects of amino acid sequence changes on antibody-antigen interactions" *Res. Immunology*, 145:33-36 (1994).

De Jong et al., "Regulation of expression of CD27, a T cell-specific member of a novel family of membrane receptors", *J. Immunol.*, 146(8):2488-2494 (1991).

De Pascalis et al., "Grafting of "Abbreviated" Complementarity-Determining Regions Containing Specificity-Determining Residues Essential of Ligand Contact to Engineer a Less Immunogenic Humanized Monoclonal Antibody", *J. Immunol.* 15/169(6):3076-84 (2002).

Den Haan et al., "Identification of a graft versus host disease-associated human minor histocompatibility antigen" *Science*, 268(5216):1476-1480 (1995).

Dillman, R. O., "Monoclonal Antibodies for Treating Cancer", *Ann. Int. Med.*, 111:592-603 (1989).

Doronina et al., "Development of potent monoclonal antibody auristatin conjugates for cancer therapy", *Nature Biotechnology*, 21(7):778-784 (2003) + erratum: 21(8):941 (2003).

Emery, et al., "Humanised monoclonal antibodies for therapeutic applications", *Exp. Opin. Invest. Drugs*, 3(3):241-251 (1994).

Freshney, *Culture of Animal Cells, A Manual of Basic Technique*, Alan R. Liss, Inc., 1983, New York, p. 4.

Giralt et al., "Leukemia relapse after allogeneic bone marrow transplantation: a review", *Blood*, 84(11):3603-3612 (1994).

Goodwin et al., "Molecular and biological characterization of a ligand for CD27 defines a new family of cytokines with homology to tumor necrosis factor", *Cell*, 73(3):447-456 (1993).

Gordon et al., "Humanized Anti-CD70 Auristatin Antibody-Drug Conjugates Show Potent In Vitro Cytotoxicity in Renal Cell Carcinoma Primary Cultures Established from Patient Tumor Isolates," Abstract No. 3733, 97th Annual Meeting of the American Association for Cancer Research, Apr. 1-5, 2006, Washington, D.C.

Gravestein et al., "Cloning and expression of murine CD27: comparison with 4-1BB, another lymphocyte-specific member of the nerve growth factor receptor family", *Eur. J. Immunol.*, 23(4):943-950 (1993).

Gravestein et al., "Novel mAbs reveal potent co-stimulatory activity of murine CD27", *Int. Immunol.*, 7(4):551-557 (1995).

Grewal. "CD70 as a therapeutic target in human malignancies", *Expert Opin. Ther. Targets.* (2008) 12(3):341-351.

Gruss et al., "Pathophysiology of Hodgkin's disease: functional and molecular aspects", *Baillieres Clin. Haematol.*, 9(3):417-446 (1996).

Gura, "Systems for Identifying New Drugs Are Often Faulty", *Science*, vol. 279 (1997).

Held-Feindt et al., "CD70/CD27 ligand, a member of the TNF family, is expressed in human brain tumors", *Int. J. Cancer*, 98(3):352-356 (2002).

Hintzen et al., "A soluble form of the human T cell differentiation antigen CD27 is released after triggering of the TCR/CD3 complex," *J. Immunol.*, 147(1):29-35 (1991).

Hintzen et al., "CD27: marker and mediator of T-cell activation?", *Immunol. Today*, 15(7):307-311 (1994).

Hintzen et al., "CD70 represents the human ligand for CD 27", *Int. Immunol.*, 6(3):477-480 (1994).

Hintzen et al., "Characterization of the human CD27 ligand, a novel member of the TNF gene family", *J. Immunol.*, 152(4):1762-1773 (1994).

Hintzen et al., "Engagement of CD27 with its ligand CD70 provides a second signal for T cell activation", *J. Immunol.*, 154(6):2612-2623 (1995).

Hintzen et al., "Regulation of CD27 expression on subsets of mature T-lymphocytes", *J. Immunol.*, 151(5):2426-2435 (1993).

Hishima et al., "CD70 expression in thymic carcinoma", *Am. J. Surg. Pathol.*, 24(5):742-746 (2000).

Holm et al., "Functional mapping and single chain construction of the anti-cytokeratin 8 monoclonal antibody TS1", *Mol. Immunol.*, 44:1075-84.(2007). Epub 2006.

Jacquot et al., "CD154/CD40 and CD70/CD27 interactions have different and sequential functions in T cell-dependent B cell responses: enhancement of plasma cell differentiation by CD27 signaling", *J. Immunol.*, 159(6):2652-2657 (1997).

Jeffrey et al., "Development and properties of beta-glucuronide linkers for monoclonal antibody-drug conjugates", *Bioconjug. Chem.*, 17(3):831-840 (2006). (300EP SR).

Klussman, et al., "Immune Modulation Mediated by the Humanized Anti-CD70 Monoclonal Antibody SGN-70", Experimental Biology, San Diego, California, Apr. 5-9, 2008 (poster).

Knoll et al., "Targeted Therapy of Experimental Renal Cell Carcinoma with a Novel Conjugate of Monoclonal Antibody 138H11 and Calicheamicin θI¹", *Cancer Research*, 60:6089-6094 (2000). (300EP SR)

Kobata et al., "CD27-CD70 interactions regulate B-cell activation by T cells," *PNAS*, 92(24):11249-11253 (1995).

Kussie et al., "A Single Engineered Amino Acid Substitution Changes Antibody Fine Specificity", *J. Immunol.* 152:146-152, 1994.

Law et al., "Anti-CD70 Antibody Drug Conjugates Mediate Renal Carcinoma Cell Killing Through Cytotoxic Drug Delivery and Antibody-Dependent Cellular Cytotoxicity (abstract only)", *Proc Amer Assoc Cancer Res.* 46:6143 (2005).

Law et al., "Lymphocyte Activation Antigen CD70 Expressed by Renal Cell Carcinoma Is a Potential Therapeutic Target for Anti-CD70 Antibody-Drug Conjugates", *Cancer Res.*, 2006; 66:(4) 2328-2337.

Lazar et al., "Transforming growth factor a: mutation of aspartic acid 47 and leucine 48 results in different biological activities", *Mol. Cell. Biol.* 8:1247-1252 (1988).

Lens et al., "Aberrant expression and reverse signaling of CD70 on malignant B cells," *Br. J. Haematol.*, 106(2):491-503 (1999).

Lens et al., "Antigen-presenting cell-derived signals determine expression levels of CD70 on primed T cells", *Immunol.*, 90:38-45 (1997).

(56) References Cited

OTHER PUBLICATIONS

Lens et al., "Control of lymphocyte function through CD27-CD70 interactions," *Semin Immunol.*, 10(6):491-499 (1998).
Lens et al., "Phenotype and function of human B cells expressing CD70 (CD27 ligand)", *Eur. J. Immunol.*, 26(12):2964-2971 (1996).
Liu et al., "Chimeric Mouse-Human IGG1 Antibody That Can Mediate Lysis of Cancer Cells", *Proc Natl Acad Sci* 84(1): 3439-3443 (1987).
Locksley et al., "The TNF and TNF receptor superfamilies: integrating mammalian biology", *Cell*, 104(4):487-501 (2001).
MacCallum, et al "Antibody-antigen Interactions: Contact Analysis and Binding Site Topography", *J. Mol. Biol.*, 262:732-745 (1996).
Manocha et al., "Blocking CD27-CD70 Costimulatory Pathway Suppresses Experimental Colitis", J Immunol 183: 270-276 (2009).
Maurer et al., "CD27 expression by a distinct subpopulation of human B lymphocytes," *Eur. J. Immunol.*, 20(12):2679-2684 (1990).
McEarchern et al., "Engineered Anti-CD70 Antibody with Multiple Effector Functions Exhibits in vitro and in vivo Antitumor Activities", *Blood*, 2007; 109(3) 1185-1192.
McEarchern, Julie, "Antitumor Activities of Engineered Anti-CD70 Antibody (h1F6)", *Presentation by Seattle Genetics at Annual Meeting of American Association for Cancer Research* Apr. 16-20:1-15 (2005).
McEarchern et al., "Targeting CD70 for the Treatment of Autoimmune Disorders", ACR, San Francisco, California, Oct. 24-29, 2008 (poster).
Morrison, "In Vitro Antibodies: Strategies for Production and Application", *Annual Rev Immunol* 10(1): 239-265 (1992).
Nakajima et al., "Involvement of CD70-CD27 interactions in the induction of experimental autoimmune encephalomyelitis", *J. Neuroimmunol.*, 109(2):188-196 (2000).
Nakajima et al., "Roles of IL-4 and IL-12 in the development of lupus in NZB/W F1 mice", *J. Immunol.*, 158(3):1466-1472 (1997).
Oelke et al., "Overexpression of CD70 and Overstimulation of IgG Synthesis by Lupus T Cells and T Cells Treated With DNA Methylation Inhibitors", *Arthritis & Rheumatism*, 50(6):1850-1860 (2004).
Oflazoglu et al., "Inhibition of collagen-induced arthritis by an antibody targeting CD70", FOCIS 2008, Boston, MA, Jun. 7, 2008 (poster).
Oflazoglu et al. "Blocking of CD27-CD70 Pathway by Anti-CD70 Antibody Ameliorates Joint Disease in Murine Collagen-Induced Arthritis", J Immunol 183: 3770-3777 (2009).
Orengo et al., "Reciprocal expression of CD70 and of its receptor, CD27, in human long term-activated T and natural killer (NK) cells: inverse regulation by cytokines and role in induction of cytotoxicity", *Clin. Exp. Immunol.*, 107(3):608-613 (1997).
Oshima et al., "Characterization of murine CD70 by molecular cloning and mAb", *Int. Immunol.*, 10(4):517-526 (1998).
Paul, Willliam, "Fundamental Immunology", 3rd edition, Laboratory of Immunology National Institute of Allergy and Infectious Diseases 292-295 (1993).
Peitsch et al., "Comparative molecular modeling of the Fas-ligand and other members of the TNF family", *Mol. Immunol.*, 32(10):761-772 (1995).
Reff, M. et al., "Future of Monoclonal Antibodies in the Treatment of Hematologic Malignancies," *Cancer Control.* 9(2):152-166 (2002).
Rudikoff et al.,"Single amino acid substitution altering antigen-binding specificity", *PNAS*, 79(6):1979-1983, Mar. 1982.
Schnell et al., "Current Strategies of Antibody-Based Treatment in Hodgkin's Disease", *Annals of Oncology*, 13 (Supplement 1): 57-66, 2002.
Skolnick et al., "From genes to protein structure and function: novel applications of computational approaches in the genomic era", *Trends in Biotechnology* 18:34-39 (2000).
Smith et al., "A receptor for tumor necrosis factor defines an unusual family of cellular and viral proteins", *Science*, 248(4958):1019-1023 (1990).
Stein et al., "A5 Cluster Report: CDw70", pp. 446-449 from Leucocyte Typing IV White Cell Differentiation Antigens, Knapp, eds., Oxford University Press, 1989.

Sugita et al., "Participation of the CD27 antigen in the regulation of IL-2-activated human natural killer cells", J. Immunol., 149(4):1199-1203 (1992).
Tesselaar et al., "Characterization of murine CD70, the ligand of the TNF receptor family member CD27," *J. Immunol.*, 159(10):4959-4965 (1997).
Tesselaar et al., "Lethal T cell immunodeficiency induced by chronic costimulation via CD27-CD70 interactions", *Nature Immunol* 4(1): 49-54 (2003).
Vajdos et al. "Comprehensive Functional Maps of the Antigen-binding Site of an Anti-ErbB2 Antibody Obtained with Shotgun Scanning Mutagenesis", *J. Mol Biol.*, 5;320(2):415-28 (2002).
Van Lier et al., "Tissue distribution and biochemical and functional properties of Tp55 (CD27), a novel T cell differentiation antigen", *J. Immunol.*, 139(5):1589-1596 (1987).
White, "Antibody-Targeted Immunotherapy For Treatment of Malignancy", *Annual Review of Medicine*; 2001; 52, Health & Medical Complete, p. 25.
Wischhusen et al., "Identification of CD70-mediated apoptosis of immune effector cells as a novel immune escape pathway of human glioblastoma", *Cancer Res.*, 6299):2592-2599 (2002).
Witzig et al., "Radioimmunotherapy for patients with relapsed B-cell non-Hodgkin lymphoma", *Cancer Chemother. Pharmacol.*, 48(suppl. 1):S91-S95 (2001).
Wu et al., "Humanization of a Murine Monoclonal Antibody by Simultaneous Optimization of Framework and CDR Residues", *J. Mol. Biol.*, 19:294(1):151-62 (1999).
Zips et al., "New Anticancer Agents: In Vitro and In Vivo Evaluation", *In Vivo* 19:1-8 (2005).
PCT/US04/05247 (published as WO 2004/073656 A3), International Search Report mailed Dec. 22, 2004.
PCT/US04/05247 (published as WO 2004/073656 A3), International Search Report mailed Dec. 22, 2004 (Corrected Version as published on Sep. 1, 2005).
PCT/US05/36994 (published as WO/2006/044643 A3), International Search Report mailed Jun. 2, 2006.
PCT/US05/36994 (published as WO/2006/044643 A3), Written Opinion of the International Searching Authority mailed Jun. 2, 2006.
PCT/US06/015145 (published as WO 2006/113909 A3), International Search Report and Written Opinion mailed Oct. 16, 2007.
PCT/US06/037753 (published as WO 2007/038637 A3), International Search Report mailed Oct. 4, 2007.
PCT/US07/087401 (published as WO 2008/074004 A3), International Search Report mailed Oct. 7, 2008.
U.S. Appl. No. 10/546,304, Amendment filed Nov. 21, 2008 in response to Final Office Action mailed May 22, 2008.
U.S. Appl. No. 10/546,304, Final Office Action mailed May 22, 2008.
U.S. Appl. No. 10/546,304, Non-Final Office Action mailed Feb. 13, 2009.
U.S. Appl. No. 10/546,304, Amendment filed May 18, 2009 in response to Non-Final Office Action mailed Feb. 13, 2009.
U.S. Appl. No. 10/983,340, Amendment filed Jul. 9, 2007 in response to Office Action mailed Mar. 9, 2007.
U.S. Appl. No. 10/983,340, Office Action mailed Oct. 4, 2007.
Hurwitz et al., "Suppression and promotion of tumor growth by monoclonal antibodies to Erbil-2 differentially correlate with cellular uptake," Proc. Natl. Acad. Sci. USA, 92(8):3353-3357, (1995).
Law et al., "Anti-CD70 Auristatin Conjugates with Potent and Selective Activity Against Renal Cell Carcinoma," poster presentation, 4th International Kidney Cancer Symposium, Oct. 21-23, 2005, Chicago, IL.
McEarchern et al., "Engineered Anti-CD70 Antibody Variants Support Multiple Effector Functions and Exhibit Potent In Vitro and In Vivo Antitumor Activities (abstract only)", *Proc Amer Assoc Cancer Res.* 46:6142 (2005).
McEarchern et al., "A Humanized Anti-CD70 Monoclonal Antibody Targets CD70-Expressing Multiple Myeloma," Publication No. 1591, 47th Annual Meeting and Exposition of The American Society of Hematology, Dec. 10-13, 2005, Atlanta, Georgia.
Oflazoglu et al. "In Vivo Characterization of the Mechanism of Action of c1F6, an Anti-CD70 Antibody," Abstract No. 3732, 97th Annual Meeting of the American Association for Cancer Research, Apr. 1-5, 2006, Washington, D.C.

(56) References Cited

OTHER PUBLICATIONS

EP 1 594 542 (EP App. No. 04713441), Supplementary Partial European Search Report mailed Mar. 12, 2007.
EP 1 799 262, Supplemental European Search Report mailed Sep. 17, 2009.
U.S. Appl. No. 10/546,304, Non-Final Office Action mailed Jul. 23, 2007.
U.S. Appl. No. 10/546,304, Notice of Allowance mailed Sep. 18, 2009.
U.S. Appl. No. 10/546,304, Restriction Requirement mailed Apr. 13, 2007.
U.S. Appl. No. 11/735,376, Non Final Office Action mailed May 26, 2010.
U.S. Appl. No. 11/735,376, Non Final Office Action mailed Aug. 3, 2009.
U.S. Appl. No. 11/735,376, Notice of Abandonment mailed Dec. 27, 2010.
U.S. Appl. No. 11/735,376, Restriction Requirement mailed Nov. 5, 2008.
U.S. Appl. No. 12/467,182, Restriction Requirement mailed Apr. 21, 2011.
U.S. Appl. No. 12/467,182, Non Final Office Action mailed Aug. 23, 2011.
U.S. Appl. No. 12/635,607, Non Final Office Action mailed Oct. 11, 2011.
U.S. Appl. No. 12/635,607, Non Final Office Action mailed Oct. 18, 2012.
U.S. Appl. No. 12,635,571, Non-Final Office Action mailed Oct. 13, 2011.
U.S. Appl. No. 12/635,571, Final Office Action mailed Mar. 7, 2012.
U.S. Appl. No. 12/467,182, Notice of Allowance mailed Mar. 1, 2012.
U.S. Appl. No. 13/491,475, Notice of Allowance mailed Jan. 22, 2013.

\* cited by examiner

Figure 1

1F6 VL nucleotide sequence:

```
  1  atggagacag acacactcct gttatggta  ctgctgtctct gggttccagg ttccactggt   60
 61  gacattgtgc tgacacagtc tcctgcttcc aagtgtcagt ctctgggca gaggccacc    120
121  atctcatgca gggccagcaa aagtgtcagt acatctgct atagtttat gcactggtat    180
181  caacagaaac caggacagcc acccaaactc ctcatctatc ttgcatccaa cctagaatct    240
241  ggggtccctg ccaggttcag tggcagtggg tctgggacag acttcaccct caacatccat    300
301  cctgtggagg aggaggatgc tgcaacctat tactgtcagc acagtaggga ggttcccgtgg    360
361  acgttggtg gaggcaccaa gctggaaatc aaacgg                                 396   (SEQ ID NO:57)
```

1F6 VL amino acid sequence:

```
-20  METDTLLLWV LLLWVPGSTG                                                     0   (SEQ ID NO:14)
  1  DIVLTQSPAS LAVSLGQRAT ISCRASKSVS TSGTSFMHWY QQKPGQPPKL LIYLASNLES        60
 61  GVPARFSGSG SGTDFTLNIH PVEEEDAATY YCQHSREVPW IFGGGTKLEI KR              112   (SEQ ID NO:51)
```

1F6 VH nucleotide sequence:

```
  1  atggcttggg tgtggacctt gctattcctg atgcagctg gctattccctg ccaagcacag       60
 61  atccagttg tgcagtctgg acctgaggtg aagaagcctg gagagactcc caagatctcc      120
121  tgcaaggctt ctgggtatac cttcacaaac tatggaatga actgggtgaa gcaggctcca      180
181  ggaaagggtt taaagtggat gggctggata aacacctaca ctggagagcc aacatatgct      240
241  gatgcctcca agggacggtt tgccttctct ttggaaacct ctgccagcac tgcctatttg      300
301  cagatcaaca acctcaaaga tgaggacact gctacatatt tctgtgcaag agactaacggc     360
361  gactatggta tggactactg gggtcaagga acctcagtca cgccctctcc a               411   (SEQ ID NO:58)
```

1F6 VH amino acid sequence:

```
-19  MAWVWTLLFL MAAAQSAGA                                                       0   (SEQ ID NO:4)
  1  QIQLVQSGPE VKKPGETVKI SCKASGYTFT NYGMNWVKQA PGKGLKWMGW INTYTGEPTY        60
 61  ADAFKGRFAF SLETSASTAY LQINNLKNED TATYFCARDY GYGMDYWGQ GTSVTVSS          118   (SEQ ID NO:50)
```

Figure 2

2F2 VL nucleotide sequence:

```
  1  atggagacag acacactcct gttatggta ctgctgtctc tggttccagg ttccactggt   60
 61  gacattgtgc tgacacagtc tcctgcttcc gagtgtcagt ctgtgtctat ttaactgtat  120
121  atctcatgca gggccagcaa caggacagtc acccaaactc acatctgget ctcatctat   180
181  caactgaaac caggacagtc caggacagtc tgcaccttca ttgcgtccaa cctaccatct  240
241  gggtccctg  ccaggttcag tggcagtggg tctgggacag acttcacct  caaaatccat  300
301  cctgtggagg aggaggatgc tgcaacctat tactgtcagc acagtaggga gattccgtac  360
361  acgttcggag gggggaccaa gctggaaata acacgg                            396
```

2F2 VL amino acid sequence:

```
-20  METDTILLWV LLLWVPGSTG                                               0  (SEQ ID NO:59)
  1  DIVLTQSPAS LTVSLGQRAT ISCRASKSVS TSGYSFMHWY QIKPGQSPKL LIYLASNLES   60  (SEQ ID NO:34)
 61  GVPARFSGSG SGTDFTLKIH PVEEEDAATY YCQHSREIPY TR                    112  (SEQ ID NO:53)
```

2F2 VH nucleotide sequence:

```
  1  atggaatgga cctggtctt  tctcttcctc ctgtcagtaa ctgcagatgt ccaaatccag   60
 61  gttcagctgc aacagtctgg ggctgagctg atgaagcctg gggcctcagt gacgatgtcc  120
121  tgcaagactt ctgcctacac attcagtacc tactgaata  gtgggtaaa  acagaggcct   180
181  ggacatggcc ttgagtggat tggagaatt  tggactggaa gtggttatac tgactacaat  240
241  gagaagttca agaccaaggc cacattcact gaagatacat cctccaacac agcctacatg  300
301  caactcagca gcctgacctc tgaggactct gcggtctatt actgtgcaag atgggatagg  360
361  ctctatgcta tggactactg gggtcaagga acctcagtca ccgtctcctc a           411  (SEQ ID NO:60)
```

2F2 VH amino acid sequence:

```
-19  MEWTWVFLEL LSVTADVQS                                               0  (SEQ ID NO:24)
  1  QVQLQQSGTE LMKPGASVTM SCKTSGYTFS TYWIEWVKQR PGHGLEWIGE ILPGSGYTDY  60
 61  NEKFKAKATF TADTSSNTAY MQLSSLASED SAVYYCARWD RLYAMDYWGQ GTSVTVSS   118  (SEQ ID NO:52)
```

Figure 3

| | | |
|---|---|---|
| 1F6 CDR-L1 (residues 23 to 38): | R A S K S V S T S G Y S F M H | (SEQ ID NO:16) |
| 2F2 CDR-L1 (residues 23 to 38): | R A S K S V S T S G Y S F M H | (SEQ ID NO:36) |
| 1F6 CDR-L2 (residues 54 to 60): | L A S N L E S | (SEQ ID NO:18) |
| 2F2 CDR-L2 (residues 54 to 60): | L A S N L P S | (SEQ ID NO:38) |
| 1F6 CDR-L3 (residues 93 to 101): | Q H S R E V P W T | (SEQ ID NO:20) |
| 2F2 CDR-L3 (residues 93 to 101): | Q H S R E I P Y T | (SEQ ID NO:40) |
| 1F6 CDR-H1 (residues 26 to 35): | G Y T F T N Y G M N | (SEQ ID NO:6) |
| 2F2 CDR-H1 (residues 26 to 35): | G Y T F T Y W I E | (SEQ ID NO:26) |
| 1F6 CDR-H2 (residues 49 to 66): | W I N T Y T G E P T Y A D D A F K G | (SEQ ID NO:8) |
| 2F2 CDR-H2 (residues 49 to 66): | E I L G P S G Y T D Y N E F K A | (SEQ ID NO:28) |
| 1F6 CDR-H3 (residues 99 to 107): | D Y G D Y G M D Y | (SEQ ID NO:10) |
| 2F2 CDR-H3 (residues 99 to 107): | W D R L Y A M D Y | (SEQ ID NO:30) |

Figure 4

| | Tissue origin | Source | CD70 expression* |
|---|---|---|---|
| CA46 | American Burkitt's lymphoma | ATCC | 3.3 |
| Ramos | American Burkitt's lymphoma | ATCC | 3.2 |
| DAUDI | African Burkitt's lymphoma | ATCC | 2.6 |
| HS Sultan | African Burkitt's lymphoma | ATCC | 5.5 |
| Raji | African Burkitt's lymphoma | ATCC | 5.4 |
| MC116 | Undifferentiated B lymphoma | ATCC | 12.2 |
| Toledo | Diffused large cell B lymphoma | ATCC | 8.0 |
| WSU-NHL | Histiocytic B lymphoma | ATCC | 11.0 |
| RL | B lymphoblastic lymphoma | ATCC | 1.3 |
| HT | Diffused mixed B lymphoma | ATCC | 1.8 |
| 29SR | Large cell lymphoblastic lymphoma | ATCC | 1.9 |
| DB | Large cell lymphoblastic lymphoma | ATCC | 1.4 |
| MHH-PREB-1 | B lymphoblastic lymphoma | DSMZ | 12.2 |
| U-698-M | B lymphoblastic lymphoma | DSMZ | 3.7 |
| SU-DHL-4 | Diffused histiocytic B lymphoma | DSMZ | 1.1 |
| KMH2 | Hodgkin's disease | DSMZ | 25.0 |
| L428 | Hodgkin's disease | DSMZ | 12.9 |
| CESS | B lymphoblastoid cell line | ATCC | 20.7 |
| IM-9 | B lymphoblastoid cell line | ATCC | 14.8 |
| Jurkat | Acute T leukemia | ATCC | 1.1 |

* Ratio between the mean log fluorescence intensities for anti-CD70 binding and control IgG binding

Figure 7

| Sample | Pathology | Age | Sex | CD70 |
|---|---|---|---|---|
| RCC211 | clear cell adenocarcinoma | 67 | M | 2.6 |
| RCC213 | clear cell adenocarcinoma | 74 | M | 133.8 |
| RCC214 | clear cell adenocarcinoma | 34 | M | 92.7 |
| RCC215 | clear cell adenocarcinoma | 47 | M | 1.7 |
| RCC216 | renal cell carcinoma | 57 | M | 133.9 |
| RCC226 | renal cell carcinoma | 85 | F | 0.8 |
| RCC227 | renal cell carcinoma | 62 | F | 4.0 |
| Rcc306 | renal cell carcinoma | 49 | F | 26.0 |

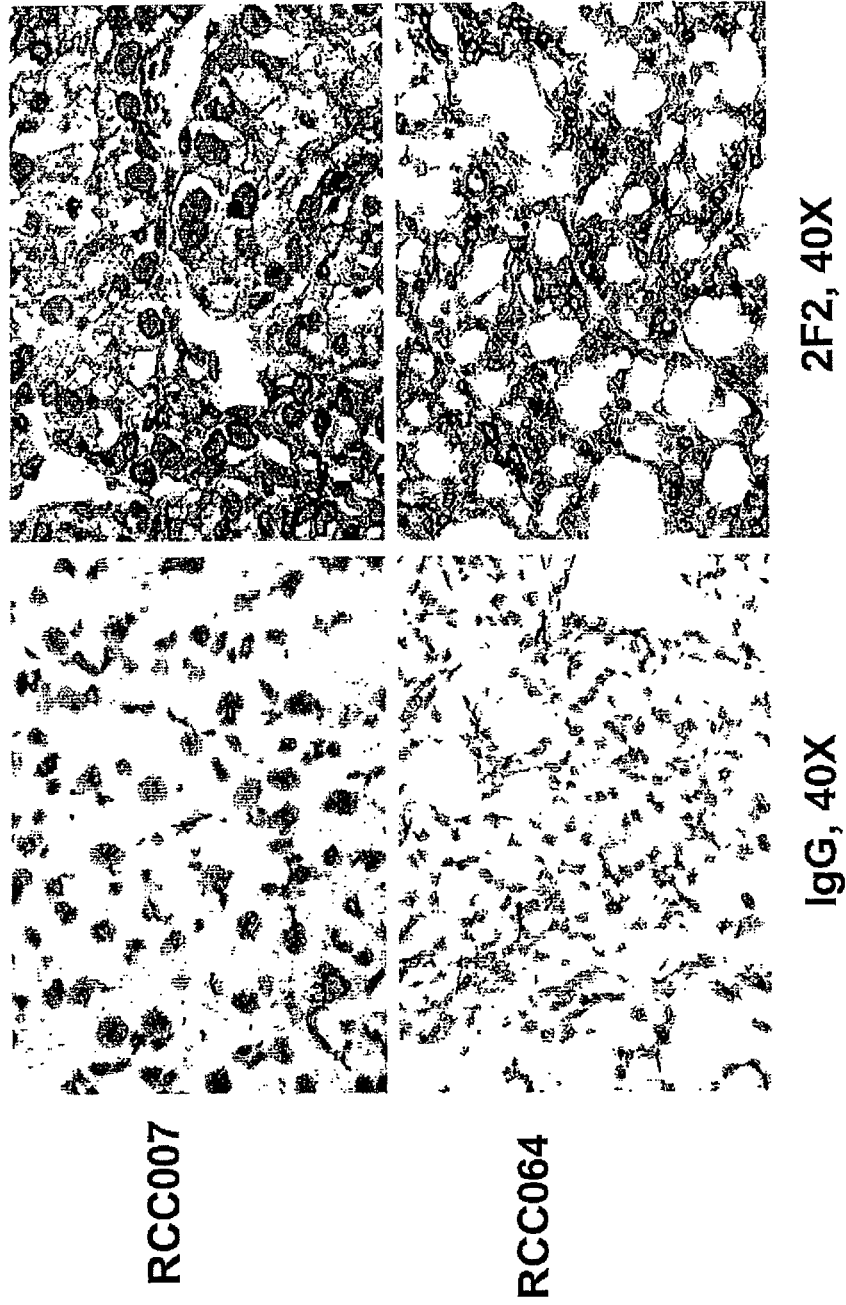

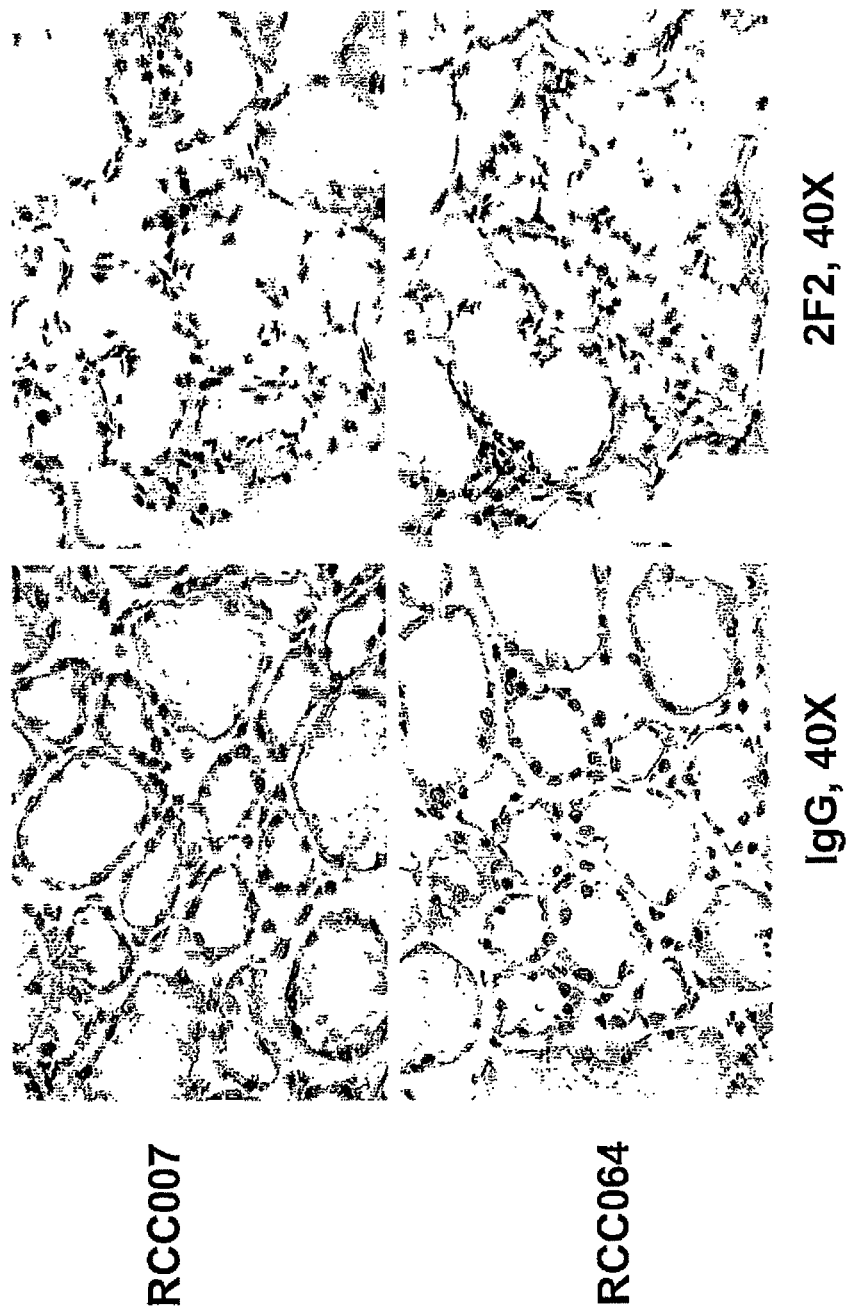

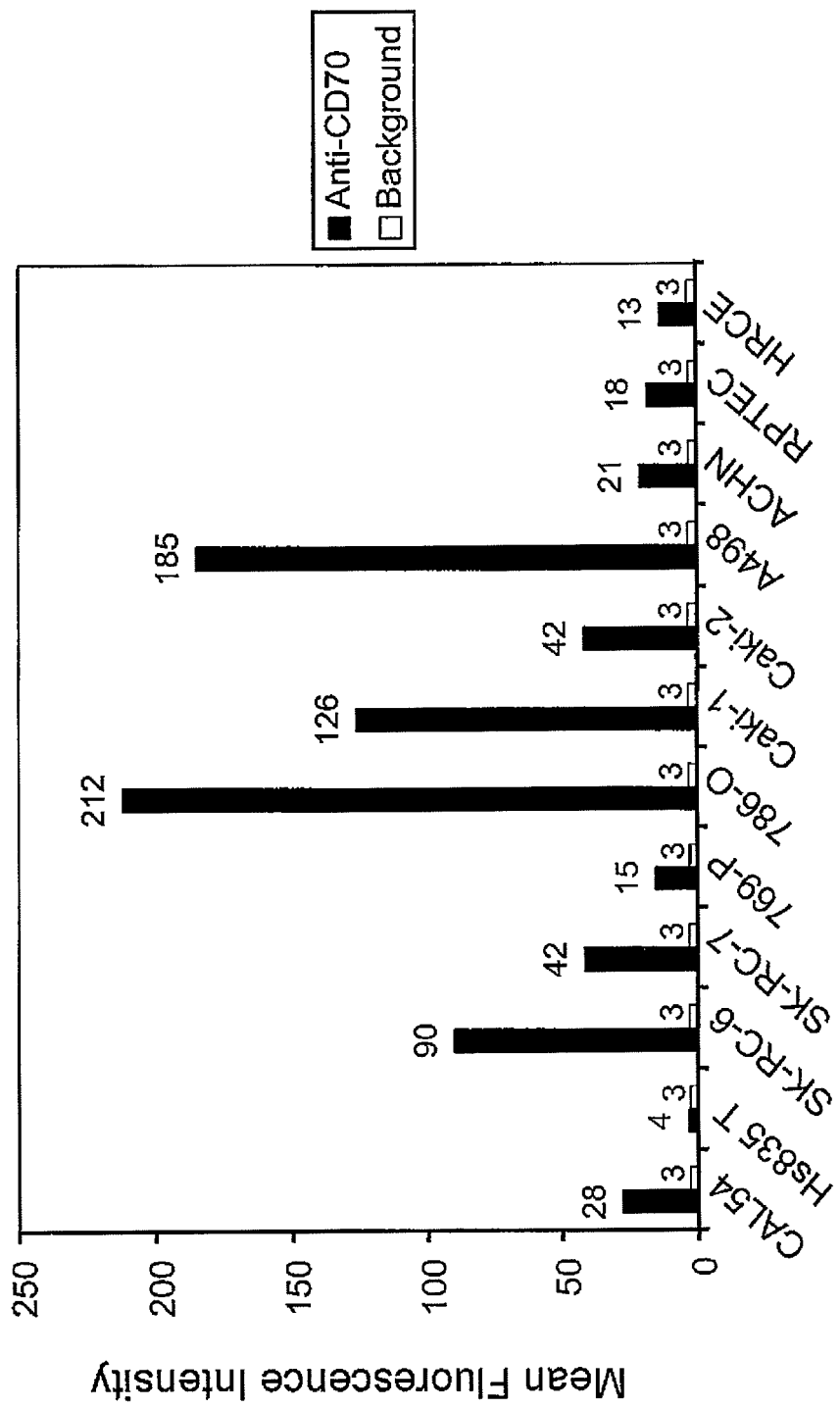

Figure 11

| | Proliferation inhibition (IC50, ng/ml) | | | | Cytotoxicity (IC50, ng/ml) | |
|---|---|---|---|---|---|---|
| | 1F6-vcMMAE | 1F6-vcMMAF | 1F6-vcAFP | IgG-vcMMAE | IgG-vcAFP | 1F6-vcMMAF | 1F6-vcAFP |
| Caki-1 | 16 | 6 | 9 | 5000 | >2000 | 24 | 14 |
| Caki-2 | 10 | 1 | 2 | 4000 | 1150 | 3 | 3 |
| 786-O | >5000 | 6 | 9 | >5000 | >5000 | 12 | 15 |
| 769-P | 2833 | 21 | 152 | >5000 | 2500 | 311 | 1238 |
| SK-RC-6 | >5000 | ND | 12 | ND | ND | ND | ND |
| SK-RC-7 | >5000 | ND | 73 | >5000 | >5000 | ND | ND |
| ACHN | >5000 | 28 | 247 | >5000 | >5000 | 696 | 800 |
| CAL54 | >5000 | 11 | 17 | ND | ND | 21 | 240 |
| A498 | >5000 | 2 | 5 | ND | ND | 2 | 2 |
| Hs 835.T | 3833 | ND | 1167 | 1500 | 1250 | ND | ND |
| RPTEC | 1325 | ND | 325 | ND | ND | >10000 | >10000 |
| HRCE | >5000 | ND | 1150 | ND | ND | >10000 | >10000 |

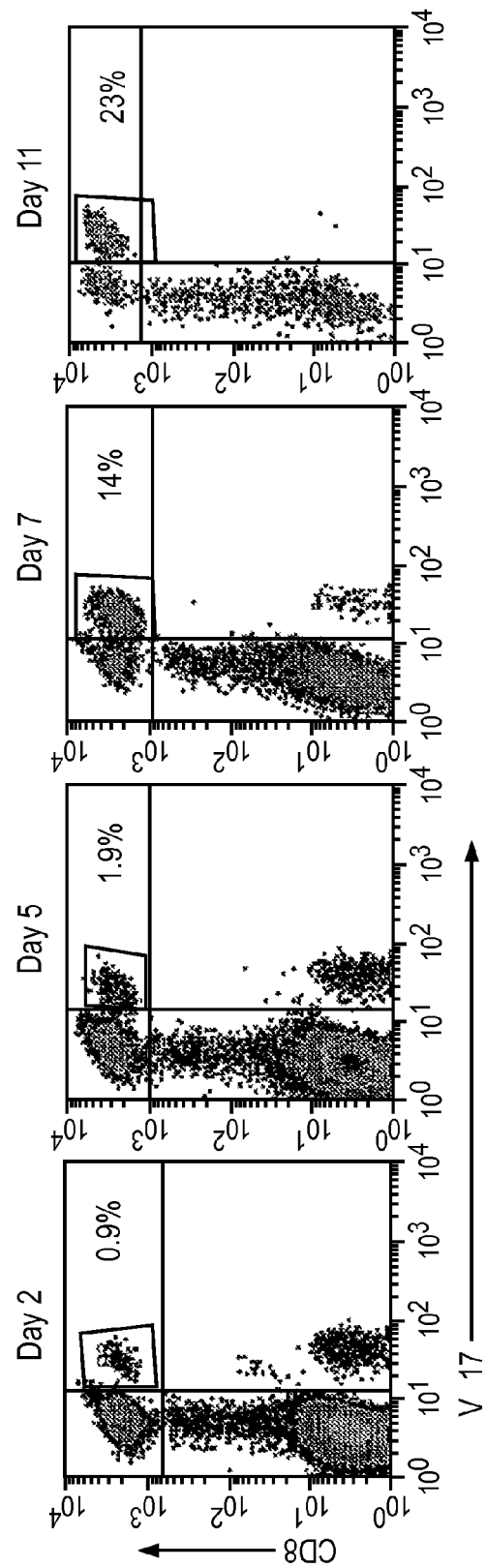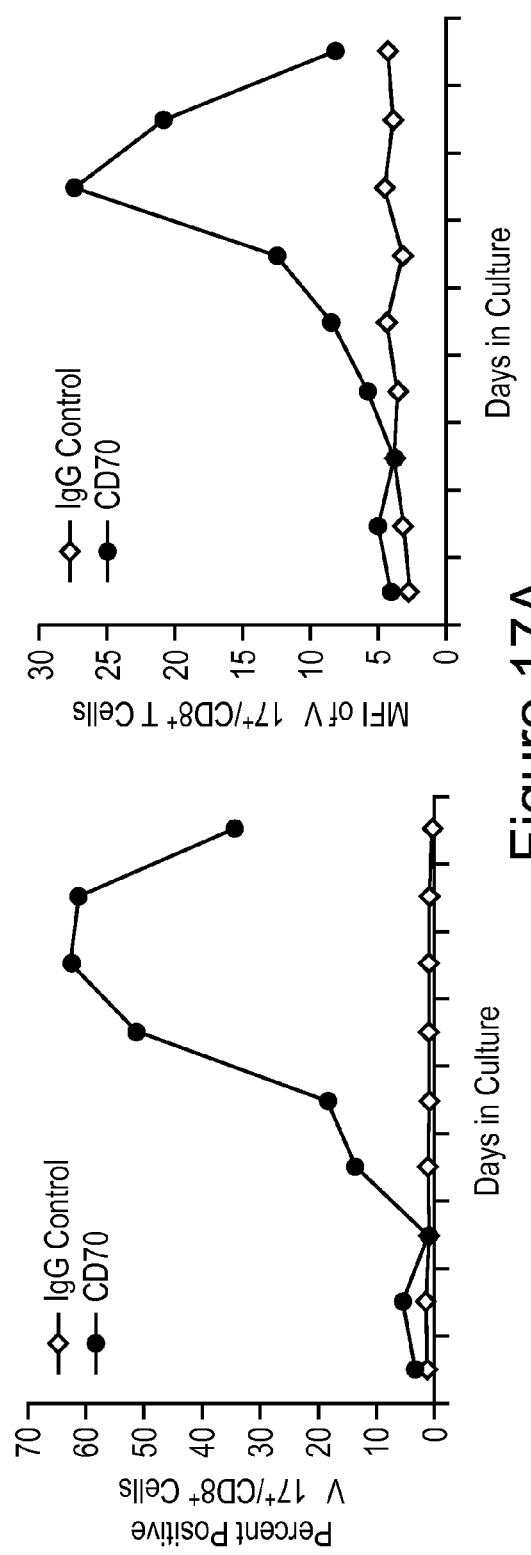
Figure 17A

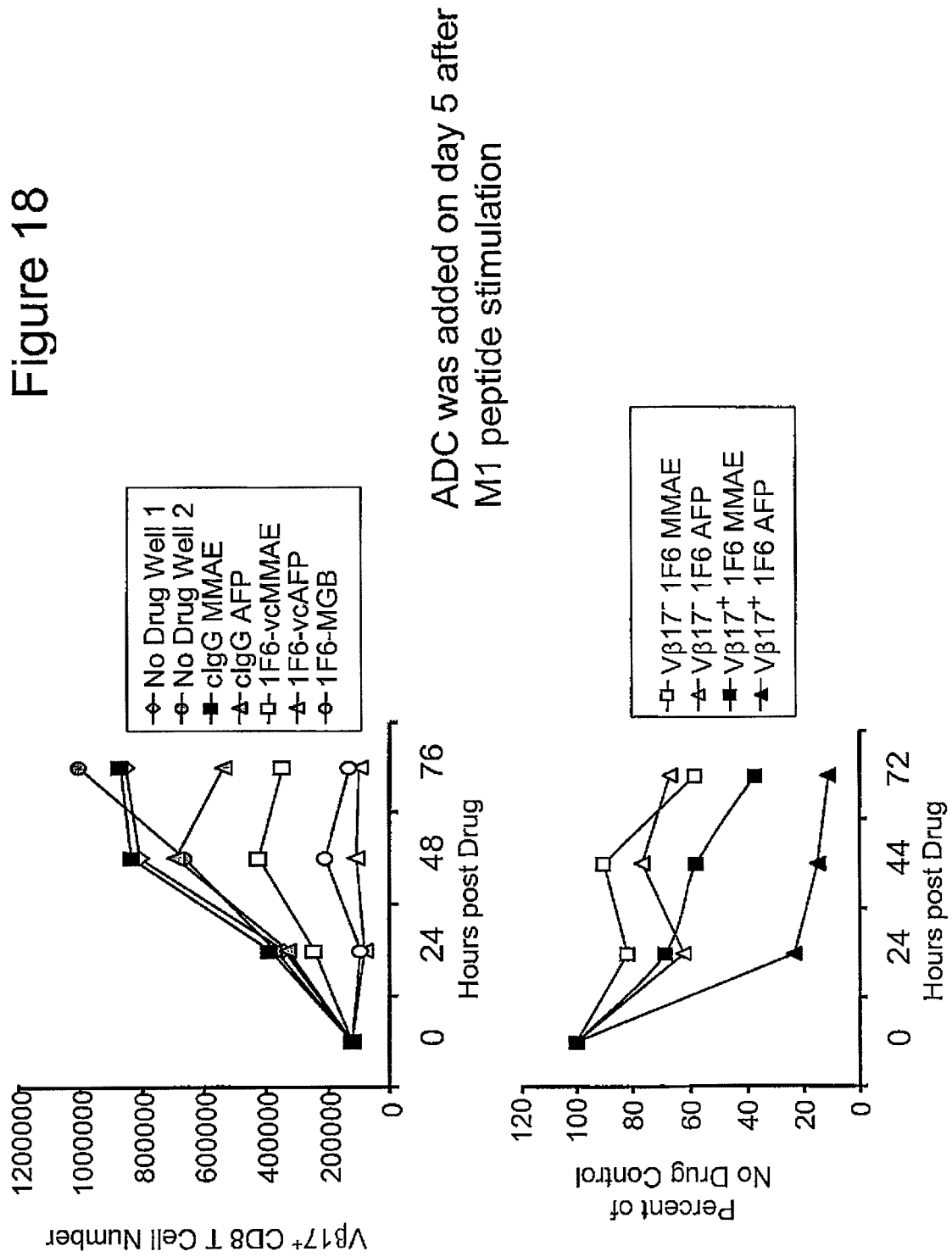

ial phomas and leukemias. This could potentially lead to functional CD27-CD70 interactions on these cells in the form of an autocrine loop, resulting in CD27 signaling and in CD70-induced proliferation, thereby providing a growth advantage to malignant cells (Lens et al., 1999, supra).

The available data supports a model in which ligation of CD27 on activated lymphocytes by CD70 delivers signals to the CD27-expressing cells, including co-stimulatory signals in T, B, and NK cells. (See, e.g., Goodwin et al., supra; Hintzen et al., 1995, *J Immunol* 154:2612-23; Oshima et al., 1998, *Int Immunol* 10:517-26; Smith et al., supra; Van Lier et al., 1987, *J Immunol* 139:1589-96; Gravestein et al., 1995, *Int Immunol* 7:551-7; Tesselaar et al., 1997, *J Immunol* 159: 4959-65; Jacquot et al., supra; Agematsu et al., 1998, *Blood* 91:173-80; Kobata et al., supra; Agematsu et al., 1997, *Eur J Immunol* 27:2073-79; Sugita et al., 1992, *J Immunol* 149: 1199-1203; Orengo et al., 1997, *Clin Exp Immunol* 107:608-13). Antibodies against both murine and human CD70 have been demonstrated to inhibit such activities, presumably by blocking the CD70/CD27 interaction (Hintzen et al., 1994, supra; Hintzen et al., 1995, supra; Oshima et al., supra).

Limited information is available on the modulation of cellular functions through CD70 signaling upon CD70/CD27 interaction, i.e., 'reverse signaling'. Some CD70 antibodies have the ability to enhance T cell proliferation when they are presented to CD70-expressing T cells either cross-linked with a secondary antibody or immobilized on tissue culture plates (Bowman et al., 1994, *J Immunol* 152:1756-61; Brugnoni, 1997, *Immunol Lett* 55:99-104). Such 'reverse signaling' has also been described in a subset of B chronic lymphocytic leukemia (B-CLL) cells, and CD70 can function as a receptor to transduce signals to facilitate proliferation of PMA-stimulated purified B-CLL cells (Lens et al., 1999, supra). These observations suggest situations in which engagement of CD27 and CD70 can result in the delivery of agonistic signals to both the CD27 and CD70 expressing cells.

The role of CD70/CD27 co-stimulation in cell-mediated autoimmune diseases has been investigated in a model of experimental autoimmune encephalomyelitis (EAE) (Nakajima et al., 2000, *J Neuroimmunol* 109:188-96). In vivo administration of a particular anti-mouse CD70 mAb (clone FR-70) markedly suppressed the onset of EAE by inhibiting antigen-induced TNF-alpha production without affecting T cell priming, Ig production or $T_H1/T_H2$ cell balance. However, such treatment had little efficacy in established disease. It has been reported that expression of CD70 on T cells was enhanced by TNF-alpha and IL-12 and down regulated by IL4 (Lens et al., 1998, supra). Thus, the CD70/CD27 mediated T cell-T cell interactions may play a role in enhancing $T_H1$-mediated immune responses rather than $T_H2$-mediated responses. Supporting this hypothesis, the anti-mouse CD70 mAb FR-70 is also effective in inhibiting $T_H1$-mediated collagen-induced arthritis (Nakajima et al., 2000, supra). In contrast, the same anti-mouse CD70 mAb did not show any efficacy in modulating lupus in NZB/NZW F1 mice and experimental Leishmania major infection in susceptible BALB/c mice, both of which are predominantly $T_H2$-mediated autoimmue response (Nakajima et al., 1997, *J Immunol* 158, 1466-72; Akiba et al., 2000, *J Exp Med* 191:375-380).

The role of CD70 has not yet been investigated in acute graft versus host disease (aGVHD), another $T_H1$-mediated immune response. GVHD is a major and often lethal consequence of allogeneic bone marrow transplantation (BMT) therapy that occurs when histocompatibility antigen differences between the BM donor and the recipient of the transplant are present (den Haan et al., 1995, *Science* 268:1476). GVHD is caused by mature T cells present in the transplanted marrow, as well as other minor cell populations (Giralt and Champlin, 1994, *Blood* 84:3603). It is noteworthy that CD70 has been detected in vivo on CD4+ cells in conditions characterized by allogeneic reaction, as in cases of maternal T cell engraftment in severe combined immune deficiency patients (Brugnoni et al., *Immunol Lett* 55:99-104). Prophylaxis of GVHD is achieved by pan-T cell immunosuppressive agents such as cyclosporine, corticosteroids, or methotrexate. In addition to the lack of specificity, these agents are also associated with significant adverse side effects. To limit these undesirable effects and the disruption of normal T cell functions, other therapeutic interventions based on selective targeting of T cells directly participating in allo-recognition and graft rejection are much needed.

CD70 is a potentially useful target for antibody-directed immunotherapy. As indicated supra, CD70 has a restricted expression pattern in normal cells: CD70 expression is mostly restricted to recently antigen-activated T and B cells under physiological conditions, and its expression is down-regulated when antigenic stimulation ceases. The key role of CD70 is believed to be facilitating plasma cell differentiation and contributing to the generation and maintenance of long-term T cell memory. Further, evidence from animal models suggests that unregulated CD70/CD27 interaction may contribute to immunological disorders, and, in humans, experimental data have also pointed towards potential abnormal regulation of the CD70/CD27 pathway in $T_H1$-mediated immune disorders such as, e.g., rheumatoid arthritis, psoriasis, and multiple sclerosis. It is of particular interest that CD70 is expressed on a variety of transformed cells including lymphoma B cells, Hodgkin and Reed-Sternberg cells, malignant cells of neural origin, and a number of carcinomas.

Several groups have demonstrated the inhibitory effect of anti-CD70 mAb in both in vitro models of lymphocyte activation and animal models of $T_H1$-mediated responses. The focus has been on the use of antibodies to block the CD70/CD27 co-stimulation pathway to achieve therapeutic efficacy. However, one main shortcoming of such an approach is the large number of signaling receptors, e.g., the CD28/CD80/CD86 co-stimulatory pathway, known to participate in immunological diseases. Consequently, blocking one specific signaling pathway may only have minimal impact on disease development. This is supported by the observations that anti-CD70 mAb can only partially inhibit in vitro T cell activation induced by allogeneic stimulator cells (Hintzen et al., 1995, supra) and an anti-CD70 mAb showed no therapeutic efficacy in EAE once the disease is established (Nakajima et al., 2000, supra).

Thus, there is a need in the art for developing an approach for depleting or inhibiting the growth of CD70-expressing cells involved in cancers and/or immunological diseases by means other than or in addition to blocking the CD70/CD27 interaction. As CD70 is expressed on the surface of mature antigen presenting dendritic cells, activated T cells, and activated B cells, agents that can target and inhibit or deplete $CD70^+$ cells may prove to be effective in the removal of antigen presenting cells presenting autoantigens and offending autoreactive activated T or B cells, as wells as CD70-expressing tumor cells.

Approaches that have been used for increasing the therapeutic efficacy of antibodies are radiolabeling and combination with chemotherapy; however, these approaches include associated with undesirable side effects. For example, isotope therapy is associated with myelosuppression (Witzig, 2001, *Cancer Chemother Pharmacol* 48 (Suppl 1):S91-5), and combining therapy with antibodies and chemotherapeutics is associated with immunosuppression. Further, isotopically labeled substances are difficult to produce, and patients often experience relapse after initial treatment with isotopically labeled substances.

Accordingly, there is a need for anti-CD70 antibody-drug conjugates (ADCs) that are constructed in such a manner so as to be capable of exerting a clinically useful cytotoxic, cytostatic, or immunosuppressive effect on CD70-expressing cells, particularly without exerting undesirable effects on non-CD70-expressing cells. Such compounds would be useful therapeutic agents against cancers that express CD70 or immune disorders that are mediated by CD70-expressing cells. (The recitation of any reference in this application is not an admission that the reference is prior art to this application.)

BRIEF SUMMARY OF THE INVENTION

The present invention provides antibody-drug conjugates (ADCs) and ADC derivatives and methods relating to the use of such conjugates to treat CD70-expressing cancers and immunological disorders. The antibody, or other targeting moiety in the ADC, binds to CD70. A drug conjugated to the antibody or targeting moiety exerts a cytotoxic, cytostatic, or immunosuppressive effect on CD70-expressing cells to treat or prevent recurrence of CD70-expressing cancers or immunological disorders.

In one aspect, methods are provided for the treatment of a CD70-expressing cancer in a subject. The methods generally include administering to the subject an effective amount of an antibody-drug conjugate. The antibody-drug conjugate includes an antibody that binds to CD70 ("CD70 antibody"). The antibody is conjugated to a drug that is a cytotoxic or cytostatic agent. In certain embodiments, the antibody is the monoclonal antibody 1F6 or 2F2.

In other embodiments, the antibody binds to CD70 and competes for binding to CD70 with monoclonal antibody 1F6 or 2F2 . Such a CD70 antibody can include at least one polypeptide region selected from (a) an H1 region having at least 80% sequence identity to the amino acid sequence set forth in SEQ ID NO:6; (b) an H2 region having at least 80% sequence identity to the amino acid sequence set forth in SEQ ID NO:8; an H3 region having at least 80% sequence identity to the amino acid sequence set forth in SEQ ID NO:10; (d) an L1 region having at least 80% sequence identity to the amino acid sequence set forth in SEQ ID NO:16; (e) an L2 region having at least 80% sequence identity to the amino acid sequence set forth in SEQ ID NO:18; (f) an L3 region having at least 80% sequence identity to the amino acid sequence set forth in SEQ ID NO:20; (g) an H1 region having at least 80% sequence identity to the amino acid sequence set forth in SEQ ID NO:26; (h) an H2 region having at least 80% sequence identity to the amino acid sequence set forth in SEQ ID NO:28; (i) an H3 region having at least 80% sequence identity to the amino acid sequence set forth in SEQ ID NO:30; (j) an L1 region having at least 80% sequence identity to the amino acid sequence set forth in SEQ ID NO:36; (k) an L2 region having at least 80% sequence identity to the amino acid sequence set forth in SEQ ID NO:38; and (l) an L3 region having at least 80% sequence identity to the amino acid sequence set forth in SEQ ID NO:40.

In certain embodiments, the CD70 antibody includes the H1, H2, and H3 regions of (a), (b), and (c) (supra); or the H1, H2, and H3 regions of (g), (h), and (i) (supra). In additional embodiments, the H1, H2, H3, L1, L2 and L3 regions of the CD70 antibody include polypeptide regions have the amino acid sequences set forth in SEQ ID NO:6, SEQ ID NO:8, SEQ ID NO:10; SEQ ID NO:16, SEQ ID NO:18, and SEQ ID NO:20, respectively.

In additional embodiments, the H1, H2, and H3 regions correspond to (a), (b), and (c) (supra) and the L1, L2, and L3 regions correspond to (d), (e), and (f) (supra), respectively; or the H1, H2, and H3 regions correspond to (g), (h), and (i) (supra) and the L1, L2, and L3 regions correspond to (j), (k), and (l) (supra). In further embodiments, the CD70 antibody comprises a heavy chain variable region having at least 80% sequence identity to the amino acid sequence set forth in SEQ ID NO:2 or SEQ ID NO 22 . The CD70 heavy chain variable region also can have the amino acid sequence set forth in SEQ ID NO:2 or SEQ ID NO:22.

In yet other embodiments, the heavy chain variable region has at least 80% sequence identity to SEQ ID NO:2 or SEQ ID NO:22, and the light chain variable region has at least 80% sequence identity to the amino acid sequence set forth in SEQ ID NO:12 or SEQ ID NO:32 . The light chain variable region also can have the amino acid sequence set forth in SEQ ID NO:12 or SEQ ID NO:32.

In exemplary embodiments, the antibody-drug conjugate is 1F6-val-cit-AFP, 1F6-val-cit-MMAF, 1F6-val-cit-MMAE, 2F2-val-cit-AFP, 2F2-val-cit-MMAF, and 2F2-val-cit-MMAE.

The CD70 antibody can be, for example, a chimeric, humanized, or human antibody. In certain embodiments, the CD70 antibody is a chimeric antibody having a human constant region. The CD70 antibody can be monovalent or polyvalent.

Suitable cytotoxic agents can be, for example, an auristatin, a DNA minor groove binding agent, a DNA minor groove alkylating agent, an enediyne, a lexitropsin, a duocarmycin, a taxane, a puromycin, a dolastatin, a maytansinoid, and a vinca alkaloid. In specific embodiments, the cytotoxic agent is AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, or netropsin. Other suitable cytotoxic agents include anti-tubulin agents, such as an auristatin, a vinca alkaloid, a podophyllotoxin, a taxane, a baccatin derivative, a cryptophysin, a maytansinoid, a combretastatin, or a dolastatin. In specific embodiments, the antitubulin agent is AFP, MMAF, MMAE, AEB, AEVB, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM-1, or eleutherobin.

In antibody drug conjugates, the antibody can be conjugated directly to the cytotoxic agent or via a linker. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit) or a phenylalanine-lysine (phe-lys) linker. Other suitable linkers include linkers hydrolyzable at a pH of less than 5.5, such as a hydrazone linker. Additional suitable cleavable linkers include disulfide linkers.

An antibody-drug conjugate can be targeted to CD70-expressing cells, such as for example, Hodgkin's disease (e.g., Reed-Sternberg cells); cancers of the B-cell lineage, including, e.g., diffuse large B-cell lymphomas, follicular lymphomas, Burkitt's lymphoma, mantle cell lymphomas, B-cell lymphocytic leukemias (e.g., acute lymphocytic leukemia, chronic lymphocytic leukemia); Epstein Barr Virus positive B cell lymphomas; gliomas; glioblastomas; neuroblastomas;

astrocytomas; meningiomas; Waldenstrom macroglobulinemia; multiple myelomas; and colon, stomach, and rectal carcinomas. The antibody-drug conjugate also can be targeted to CD70-expressing immune cells, such as an activated T cell, an activated B cell, or a mature dendritic cell. The antibody-drug conjugates can be administered to humans or to non-human animals.

In another aspect, methods are provided for treating an immunological disorder. The methods generally include administering to a subject an amount effective of an antibody-drug conjugate comprising an antibody that binds CD70. The antibody is conjugated to a cytotoxic agent or an immunosuppressive agent. In certain embodiments, the antibody is the monoclonal antibody 1F6 or 2F2.

In other embodiments, the antibody binds to CD70 and competes for binding to CD70 with monoclonal antibody 1F6 or 2F2. The CD70 antibody can include at least one polypeptide region selected from (a) an H1 region having at least 80% sequence identity to the amino acid sequence set forth in SEQ ID NO:6; (b) an H2 region having at least 80% sequence identity to the amino acid sequence set forth in SEQ ID NO:8; an H3 region having at least 80% sequence identity to the amino acid sequence set forth in SEQ ID NO:10; (d) an L1 region having at least 80% sequence identity to the amino acid sequence set forth in SEQ ID NO:16; (e) an L2 region having at least 80% sequence identity to the amino acid sequence set forth in SEQ ID NO:18; (f) an L3 region having at least 80% sequence identity to the amino acid sequence set forth in SEQ ID NO:20; (g) an H1 region having at least 80% sequence identity to the amino acid sequence set forth in SEQ ID NO:26; (h) an H2 region having at least 80% sequence identity to the amino acid sequence set forth in SEQ ID NO:28; (i) an H3 region having at least 80% sequence identity to the amino acid sequence set forth in SEQ ID NO:30; (j) an L1 region having at least 80% sequence identity to the amino acid sequence set forth in SEQ ID NO:36; (k) an L2 region having at least 80% sequence identity to the amino acid sequence set forth in SEQ ID NO:38; and (l) an L3 region having at least 80% sequence identity to the amino acid sequence set forth in SEQ ID NO:40.

In certain embodiments, the CD70 antibody includes the H1, H2, and H3 regions of (a), (b), and (c) (supra); or the H1, H2, and H3 regions of (g), (h), and (i) (supra), respectively. In additional embodiments, the H1, H2, H3, L1, L2 and L3 regions of the CD70 antibody includes polypeptide regions have the amino acid sequences set forth in SEQ ID NO:6, SEQ ID NO:8, SEQ ID NO:10; SEQ ID NO:16, SEQ ID NO:18, and SEQ ID NO:20, respectively.

In additional embodiments, the H1, H2, and H3 regions correspond to (a), (b), and (c) (supra) and the L1, L2, and L3 regions correspond to (d), (e), and (f) (supra), respectively; or the H1, H2, and H3 regions correspond to (g), (h), and (i) (supra) and the L1, L2, and L3 regions correspond to (j), (k), and (l) (supra), respectively. In further embodiments, the CD70 antibody comprises a heavy chain variable region having at least 80% sequence identity to the amino acid sequence set forth in SEQ ID NO:2 or SEQ ID NO 22. The CD70 heavy chain variable region also can have the amino acid sequence set forth in SEQ ID NO:2 or SEQ ID NO:22.

In yet other embodiments, the heavy chain variable region has at least 80% sequence identity to SEQ ID NO:2 or SEQ ID NO:22, and the light chain variable region has at least 80% sequence identity to the amino acid sequence set forth in SEQ ID NO:12 or SEQ ID NO:32. The light chain variable region also can have the amino acid sequence set forth in SEQ ID NO:12 or SEQ ID NO:32.

In exemplary embodiments, the antibody-drug conjugate is 1F6-vat-cit-AFP, 1F6-val-cit-MMAF, 1F6-val-cit-MMAE, 2F2-val-cit-AFP, 2F2-val-cit-MMAF, and 2F2-val-cit-MMAE.

The CD70 antibody can be, for example, a chimeric, humanized, or human antibody. In certain embodiments, the CD70 antibody is a chimeric antibody having a human constant region. The CD70 antibody can be monovalent or polyvalent.

Suitable cytotoxic agents can be, for example, an auristatin, a DNA minor groove binding agent, a DNA minor groove alkylating agent, an enediyne, a lexitropsin, a duocarmycin, a taxane, a puromycin, a dolastatin, a maytansinoid, and a vinca alkaloid. In specific embodiments, the drug is cytotoxic agent is AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, or netropsin. Other suitable cytotoxic agents include anti-tubulin agents, such as an auristatin, a vinca alkaloid, a podophyllotoxin, a taxane, a baccatin derivative, a cryptophysin, a maytansinoid, a combretastatin, or a dolastatin. In specific embodiments, the antitubulin agent is AFP, MMAF, MMAE, AEB, AEVB, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM-1, or eleutherobin.

Suitable immunosuppressive agents include, for example, gancyclovir, etanercept, cyclosporine, tacrolimus, rapamycin, cyclophosphamide, azathioprine, mycophenolate mofetil, methotrexate, cortisol, aldosterone, dexamethasone, a cyclooxygenase inhibitor, a 5-lipoxygenase inhibitor, or a leukotriene receptor antagonist.

In antibody drug conjugates, the antibody can be conjugated directly to the cytotoxic agent or immunosuppressive agent, or via a linker. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease.

In exemplary embodiments, the linker can be a dipeptide linker, such as a valine-citrulline (val-cit) or a phenylalanine-lysine (phe-lys) linker. Other suitable linkers include cleavable linker hydrolyzable at a pH of less than 5 5, such as a hydrazone linker. Further suitable cleavable linkers include disulfide linkers.

The ADC can be targeted to cells of an immunological disorder, such as, for example, Th1-mediated immunological disorders. Th1-mediated immunological disorders include, for example, rheumatoid arthritis, multiple sclerosis, psoriasis, Sjorgren's syndrome, Hashimoto's thyroiditis, Grave's disease, primary biliary cirrhosis, Wegener's granulomatosis, tuberculosis, or acute graft versus host disease. Other immunological disorders include, for example, an activated B-lymphocyte disorder. The subject can be a human or a non-human animal.

In yet another aspect, antibody-drug conjugates are provided. The antibody-drug conjugates include an antibody that binds to CD70. The antibody is conjugated to a cytotoxic agent or an immunosuppressive agent. The antibody-drug conjugate can exerts a cytotoxic or cytostatic effect on a CD70-expressing cancer cell line, and/or a cytotoxic, cytostatic, or immunosuppressive effect on a CD70-expressing immune cell.

In certain embodiments, the antibody is the monoclonal antibody 1F6 or 2F2. In other embodiments, the antibody binds to CD70 and competes for binding to CD70 with monoclonal antibody 1F6 or 2F2. The CD70 antibody can include at least one polypeptide region selected from (a) an H1 region having at least 80% sequence identity to the amino acid sequence set forth in SEQ ID NO:6; (b) an H2 region having at least 80% sequence identity to the amino acid sequence set forth in SEQ ID NO:8; (c) an H3 region having at least 80% sequence identity to the amino acid sequence set forth in SEQ ID NO:10; (d) an L1 region having at least 80% sequence identity to the amino acid sequence set forth in SEQ ID NO:16; (e) an L2 region having at least 80% sequence identity to the amino acid sequence set forth in SEQ ID NO:18; (f) an L3 region having at least 80% sequence identity to the amino acid sequence set forth in SEQ ID NO:20; (g) an H1 region having at least 80% sequence identity to the amino acid sequence set forth in SEQ ID NO:26; (h) an H2 region having at least 80% sequence identity to the amino acid sequence set forth in SEQ ID NO:28; (i) an H3 region having at least 80% sequence identity to the amino acid sequence set forth in SEQ ID NO:30; (j) an L1 region having at least 80% sequence identity to the amino acid sequence set forth in SEQ ID NO:36; (k) an L2 region having at least 80% sequence identity to the amino acid sequence set forth in SEQ ID NO:38; and (l) an L3 region having at least 80% sequence identity to the amino acid sequence set forth in SEQ ID NO:40.

In certain embodiments, the CD70 antibody includes the H1, H2, and H3 regions of (a), (b), and (c) (supra); or the H1, H2, and H3 regions of (g), (h), and (i) (supra), respectively. In additional embodiments, the H1, H2, H3, L1, L2 and L3 regions of the CD70 antibody includes polypeptide regions have the amino acid sequences set forth in SEQ ID NO:6, SEQ ID NO:8, SEQ ID NO:10; SEQ ID NO:16, SEQ ID NO:18, and SEQ ID NO:20, respectively.

In additional embodiments, the H1, H2, and H3 regions correspond to (a), (b), and (c) (supra) and the L1, L2, and L3 regions correspond to (d), (e), and (f) (supra), respectively; or the H1, H2, and H3 regions correspond to (g), (h), and (i) (supra) and the L1, L2, and L3 regions correspond to (j), (k), and (l) (supra), respectively. In further embodiments, the CD70 antibody comprises a heavy chain variable region having at least 80% sequence identity to the amino acid sequence set forth in SEQ ID NO:2 or SEQ ID NO 22. The CD70 heavy chain variable region also can have the amino acid sequence set forth in SEQ ID NO:2 or SEQ ID NO:22.

In yet other embodiments, the heavy chain variable region has at least 80% sequence identity to SEQ ID NO:2 or SEQ ID NO:22, and the light chain variable region has at least 80% sequence identity to the amino acid sequence set forth in SEQ ID NO:12 or SEQ ID NO:32. The light chain variable region also can have the amino acid sequence set forth in SEQ ID NO:12 or SEQ ID NO:32.

In exemplary embodiments, the antibody-drug conjugate is 1F6-val-cit-AFP, 1F6-val-cit-MMAF, 1F6-val-cit-MMAE, 2F2-val-cit-AFP, 2F2-val-cit-MMAF, and 2F2-val-cit-MMAE.

The CD70 antibody can be, for example, a chimeric, humanized, or human antibody. In certain embodiments, the CD70 antibody is a chimeric antibody having a human constant region. The CD70 antibody can be monovalent or polyvalent.

Suitable cytotoxic agents can be, for example, an auristatin, a DNA minor groove binding agent, a DNA minor groove alkylating agent, an enediyne, a lexitropsin, a duocarmycin, a taxane, a puromycin, a dolastatin, a maytansinoid, and a vinca alkaloid. In specific embodiments, the drug is cytotoxic agent is AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, or netropsin. Other suitable cytotoxic agents include anti-tubulin agents, such as an auristatin, a vinca alkaloid, a podophyllotoxin, a taxane, a baccatin derivative, a cryptophysin, a maytansinoid, a combretastatin, or a dolastatin. In specific embodiments, the antitubulin agent is AFP, MMAF, MMAE, AEB, AEVB, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM-1, or eleutherobin.

Suitable immunosuppressive agents include, for example, gancyclovir, etanercept, cyclosporine, tacrolimus, rapamycin, cyclophosphamide, azathioprine, mycophenolate mofetil, methotrexate, cortisol, aldosterone, dexamethasone, a cyclooxygenase inhibitor, a 5-lipoxygenase inhibitor, or a leukotriene receptor antagonist.

In antibody drug conjugates, the antibody can be conjugated directly to the cytotoxic agent or immunosuppressive agent, or via a linker. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as a lysosomal protease or an endosomal protease.

Antibody drug conjugates can be targeted to CD70-expressing cancer cells, such as for example, Hodgkin's disease (e.g., Reed-Sternberg cells); cancers of the B-cell lineage, including, e.g., diffuse large B-cell lymphomas, follicular lymphomas, Burkitt's lymphoma, mantle cell lymphomas, B-cell lymphocytic leukemias (e.g., acute lymphocytic leukemia, chronic lymphocytic leukemia); Epstein Barr Virus positive B cell lymphomas; gliomas; glioblastomas; neuroblastomas; astrocytomas; meningiomas; Waldenstrom macroglobulinemia; multiple myelomas; and colon, stomach, and rectal carcinomas. The antibody-drug conjugate also can be targeted to CD70-expressing immune cells, such as an activated T cell, an activated B cell, or a mature dendritic cell.

In yet additional aspects, pharmaceutical compositions are provided for the treatment of a CD70-expressing cancer or an immunological disorder. The pharmaceutical compositions include an antibody-drug conjugate and at least one pharmaceutically compatible ingredient. In a related aspect, pharmaceutical kits are provided. The kits include a container containing an antibody-drug conjugate. The antibody-drug conjugate is typically lyophilized. The kits can further include a second container containing a pharmaceutically acceptable diluent The present invention may be more fully understood by reference to the following detailed description of the invention, non-limiting examples of specific embodiments of the invention and the appended figures.

BRIEF DESCRIPTION OF THE DRAWINGS

FIG. 1: The 1F6 $V_L$ and $V_H$ cDNA (SEQ ID NO:57 and SEQ ID NO:58, respectively, including signal sequence) and amino acid sequences (SEQ ID NO:51 and SEQ ID NO:50, respectively). The coding and amino acid sequences for the light ($V_L$, upper 2 panels;) and heavy chain ($V_H$, lower 2 panels) variable regions of 1 F6 were determined. The complementarity determining regions (CDRs) for the $V_L$ and $V_H$ were identified according to criteria described in Kabat et al., 1991, Sequences of Proteins of Immunogical Interest, Washington, DC, US Department of Health and Public Services; Chothia and Lesk, 1987, J Mol Biol 196: 901-917. Amino acid residues corresponding to the CDRs are underlined. The signal peptide for the $V_L$ and $V_H$ are identified to be amino residues -20 to 0 and -19 to 0, respectively (SEQ ID NO:14 and SEQ ID NO:4, respectively).

FIG. 2: The 2F2 $V_L$ and $V_H$ cDNA (SEQ ID NO:59 and SEQ ID NO:60, respectively, including signal sequence) and amino acid sequences (SEQ ID NO:53 and SEQ ID NO:52, respectively). The coding and amino acid sequences for the light ($V_L$, upper 2 panels) and heavy chain ($V_H$, lower 2 panels) variable regions of 2F2 were determined. The complementarity determining regions (CDRs) for the $V_L$ and $V_H$ were identified according to criteria described in Kabat et al., 1991, *Sequences of Proteins of Immunogical Interest*, Washington, DC, US Department of Health and Public Services; Chothia and Lesk, 1987, J. Mol. Biol. 196:901-917. Amino acid residues corresponding to the CDRs are underlined. The signal peptides for the $V_L$ and $V_H$ were identified to be amino residues -20 to 0 and -19 to 0, respectively (SEQ ID NO:34 and SEQ ID NO:24, respectively).

FIG. 3: Amino acid sequence comparison between the 1F6 and 2F2 CDRs. The amino acid sequences of 1F6 and 2F2 CDRs are aligned. The 1F6 CDRs as indicated on FIG. 3 are H1 (SEQ ID NO:6), H2 (SEQ ID NO:8), H3 (SEQ ID NO:10); L1 (SEQ ID NO:16), L2 (SEQ ID NO:18) L3 (SEQ ID NO:20). The 2F2CDRs as indicated on FIG. 3 are H1 (SEQ ID NO:26), H2 (SEQ ID NO:28), H3 (SEQ ID NO:30); L1 (SEQ ID NO:36), L2 (SEQ ID NO:38), L3 (SEQ ID NO:40). Underlined residues represent conservative substitutions and boxed and italic residues represent divergent substitutions.

FIG. 4: Expression of CD70 on hematologic cell lines. CD70 expression on the surface of a panel of hematologic cell lines of different tissue origins and sources was determined by flow cytometry. CD70 expression was expressed as binding ratios between the anti-CD70 mAb and control IgG.

FIG. 7: Over-expression of CD70 transcripts in renal cell carcinoma (RCC) detected by quantitative PCR. CD70 expression in RCC cDNA samples was compared to that detected in a pool of 4 normal kidneys by quantitative PCR using an ABI PRISM 7000 Sequence Detection System and the ΔCt method. Numbers represent the fold of CD70 transcript expression in RCC compared to that in normal kidneys.

FIGS. 8A and B: CD70 protein expression in frozen tumor sections of RCC. (A) Binding of the anti-CD70 mAb 2F2 (right column) and a control IgG (left column) to serial frozen tumor sections derived two RCC donors was determined by immunohistochemistry staining. Photomicrographs were taken under 40× magnification. (B) The same pair of antibodies was used to stain serial frozen normal tissue sections adjacent to the tumor obtained from the same RCC donors used in (A).

FIG. 11: Effects of anti-CD70 ADCs on the proliferation of RCC cell lines. Dose-response curves on growth inhibitory or cytotoxicity of 1F6 ADCs were determined as described in FIG. 10 to obtain $IC_{50}$ values. The $IC_{50}$s of 1F6-vcMMAE, 1F6-vcMMAF, 1F6-vcAFP, or two control non-binding IgG (IgG) ADCs on the proliferation of CD70+ RCC lines (Caki-1, Caki-2, 786-O, 769-P, SK-RC-6, SK-RC-7, ACHN, CAL54, and A498), a CD70− RCC line (Hs 835.T), and normal kidney tubule epithelial cell lines (RPTEC and HRCE) are summarized. Effects of 1F6-vcMMAF and 1F6-vcAFP on the viability of a subset of the cell lines are also summarized.

FIG. 18: Specific deletion of antigen-specific CD8$^+$/Vβ17$^+$ T cells by anti-CD70 ADCs. PBMCs from a normal HLA-A0201donor were stimulated with the M1 peptide for 5 days. 1F6 ADCs or control non-binding IgG (cIgG) ADCs were added to cells to a final concentration of 1 μg/ml. Total viable cell counts were conducted at 24, 48, and 76 hours post drug addition. The percentage of CD8$^+$/Vβ17$^+$ in each culture condition was determined by flow cytometry as shown in FIG. 17. Total numbers of CD8$^+$/Vβ17$^+$ for each culture condition are calculated (upper panel). The numbers of CD8$^+$/Vβ17$^+$ and CD8$^+$/Vβ17$^-$ cells in the 1F6-ADC treated cultures are expressed as percentages of the untreated control cultures (lower panel).

DETAILED DESCRIPTION OF THE INVENTION

Figure 5:
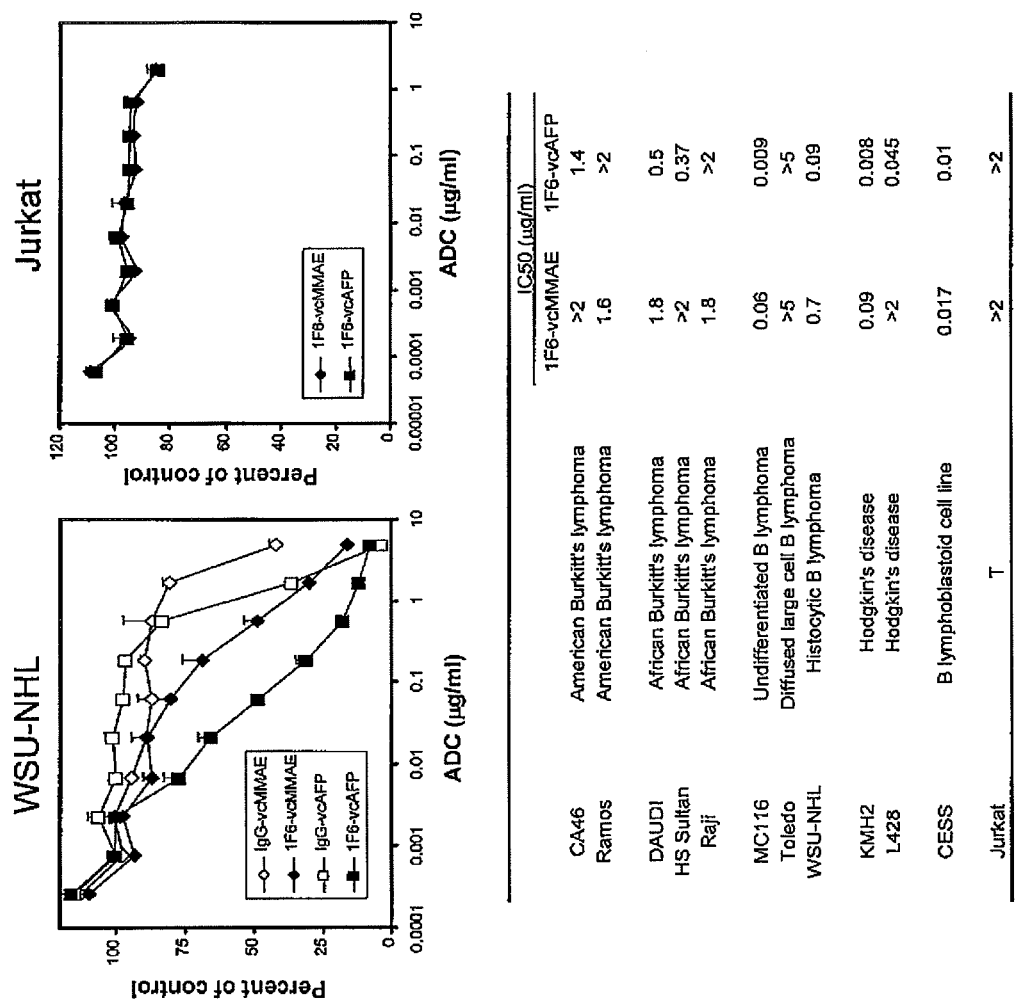
FIG. 5: Effects of anti-CD70 ADCs on the proliferation of transformed hematologic cell lines. A subset of the CD70+ cell lines shown in FIG. 4 and the CD70− Jurkat cell line were tested for their sensitivity toward 1F6 ADCs. Graded doses of the 1F6-vcMMAE, 1F6-vcAFP, or the corresponding non-binding control IgG (IgG) ADCs were added to cells at the initiation of culture. Cells were exposed to the ADCs continuously for a total of 96 hours. Proliferation was determined by pulsing with $^3$H-TdR during the last 16 hours of incubation. The upper panels show the response of the WSU-NHL and Jurkat lines. The lower panel summaries the responses by the tested cell lines to 1F6-vcMMAE and 1F6-vcAFP in form of $IC_{50}$s.

Provided are methods and compositions relating to the use of antibody-drug conjugates (ADCs) and ADC derivatives that bind to CD70. A drug conjugated to the antibody exerts a cytotoxic, cytostatic, or immunosuppressive effect on CD70-expressing cells to treat or immunological disorders or CD70-expressing cancers. In one aspect, the methods and compositions relate to antibodies and derivatives thereof that compete with monoclonal antibody 1F6 or 2F2 for binding to CD70 and that, when conjugated to a cytotoxic agent, exert a cytotoxic or cytostatic effect to deplete or inhibit the proliferation of CD70-expressing cells. Antibodies to CD70 which can be used in accordance with the methods and compositions described herein include monoclonal antibodies as well as chimeric, humanized, or human antibodies (e.g., a humanized or chimeric form of 1F6 or 2F2), and such antibodies conjugated to cytotoxic or immunosuppressive agents such as, for example, chemotherapeutic drugs.

For clarity of disclosure, and not by way of limitation, the detailed description of the invention is divided into the subsections which follow.

I. Definitions and Abbreviations

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The term "inhibit" or "inhibition" of as used herein means to a reduce by a measurable amount, or to prevent entirely.

The term "agent" as used herein means an element, compound, or molecular entity, including, e.g., a pharmaceutical, therapeutic, or pharmacologic compound. Agents can be natural or synthetic or a combination thereof. A "therapeutic agent" is an agent that exerts a therapeutic (e.g., beneficial) effect on cancer cells or activated immune cells, either alone or in combination with another agent (e.g., a prodrug converting enzyme in combination with a prodrug). Typically, therapeutic agents useful in accordance with the methods and compositions described herein are those that exert a cytotoxic, cytostatic, or immunosuppressive effect.

"Cytotoxic effect," in reference to the effect of an agent on a cell, means killing of the cell. "Cytostatic effect" means an inhibition of cell proliferation. A "cytotoxic agent" means an agent that has a cytotoxic or cytostatic effect on a cell, thereby depleting or inhibiting the growth of, respectively, cells within a cell population.

The term "deplete," in the context of the effect of a CD70-targeting moiety-drug conjugate on CD70-expressing cells, refers to a reduction or elimination of the CD70-expressing cells.

The term "immunosuppressive agent" as used herein means an agent that inhibits the development or maintenance of an immunologic response. Such inhibition by an immunosuppressive agent can be effected by, for example, elimination of immune cells (e.g., T or B lymphocytes); induction or generation of immune cells that can modulate (e.g., downregulate) the functional capacity of other cells; induction of an unresponsive, state in immune cells (e.g., anergy); or increasing, decreasing or changing the activity or function of immune cells, including, for example, altering the pattern of proteins expressed by these cells (e.g., altered production and/or secretion of certain classes of molecules such as cytokines, chemokines, growth factors, transcription factors, kinases, costimulatory molecules or other cell surface receptors, and the like). In typical embodiments, an immunosuppressive agent has a cytotoxic or cytostatic effect on an immune cell that promotes an immune response.

"Immune cell" as used herein means any cell of hematopoietic lineage involved in regulating an immune response against an antigen (e.g., an autoantigen). In typical embodiments, an immune cell is a T lymphocyte, a B lymphocyte, or a dendritic cell.

The term "polypeptide" refers to a polymer of amino acids and its equivalent and does not refer to a specific length of a product; thus, "peptides" and "proteins" are included within the definition of a polypeptide. Also included within the definition of polypeptides are "antibodies" as defined herein. A "polypeptide region" refers to a segment of a polypeptide, which segment may contain, for example, one or more domains or motifs (e.g., a polypeptide region of an antibody can contain, for example, one or more CDRs). The term "fragment" refers to a portion of a polypeptide typically having at least 20 contiguous or at least 50 contiguous amino acids of the polypeptide. A "derivative" includes a polypeptide or fragment thereof having conservative amino acid substitutions relative to a second polypeptide; or a polypeptide or fragment thereof that is modified by covalent attachment of a second molecule such as, e.g., by attachment of a heterologous polypeptide, or by glycosylation, acetylation, phosphorylation, and the like. Further included within the definition of "polypeptide" are, for example, polypeptides containing one or more analogs of an amino acid (e.g., unnatural amino acids and the like), polypeptides with unsubstituted linkages, as well as other modifications known in the art, both naturally and non-naturally occurring.

The term "antibody" as used herein refers to (a) immunoglobulin polypeptides and immunologically active portions of immunoglobulin polypeptides, i.e., polypeptides of the immunoglobulin family, or fragments thereof, that contain an antigen binding site that immunospecifically binds to a specific antigen (e.g., CD70), or (b) conservatively substituted derivatives of such immunoglobulin polypeptides or fragments that immunospecifically bind to the antigen (e.g., CD70). Antibodies are generally described in, for example, Harlow & Lane, *Antibodies: A Laboratory Manual* (Cold Spring Harbor Laboratory Press, 1988).

In the context of immunoglobulin polypeptides or fragments thereof as defined above, "conservative substitution" means one or more amino acid substiutions that do not substantially reduce specific binding (e.g., as measured by the $K_D$) of the immunoglobulin polypeptide or fragment thereof to an antigen (i.e., substitutions that increase binding, that do not significantly alter binding, or that reduce binding by no more than about 40%, typically no more than about 30%, more typically no more than about 20%, even more typically no more than about 10%, or most typically no more than about 5%, as determined by standard binding assays such as, e.g., ELISA).

An "antibody derivative" as used herein means an antibody, as defined above, that is modified by covalent attachment of a heterologous molecule such as, e.g., by attachment of a heterologous polypeptide, or by glycosylation, acetylation or phosphorylation not normally associated with the antibody, and the like.

The term "monoclonal antibody" refers to an antibody that is derived from a single cell clone, including any eukaryotic or prokaryotic cell clone, or a phage clone, and not the method by which it is produced. Thus, the term "monoclonal antibody" as used herein is not limited to antibodies produced through hybridoma technology.

The term "heterologous," in the context of a polypeptide, means from a different source (e.g., a cell, tissue, organism, or species) as compared with another polypeptide, so that the two polypeptides are different. Typically, a heterologous polypeptide is from a different species.

As used herein, the term "functional," in the context of an anti-CD70 antibody or derivative thereof to be used in accordance with the methods described herein, indicates that the antibody or derivative thereof is (1) capable of binding to CD70 and (2) depletes or inhibits the proliferation of CD70-expressing cells when conjugated to a cytotoxic agent, or has an immunosuppressive effect on an immune cell when conjugated to an immunosuppressive agent.

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In certain embodiments, the two sequences are the same length.

The term "substantially identical," in the context of two nucleic acids or polypeptides, refers to two or more sequences or subsequences that have at least 50%, at least 55%, at least 60%, or at least 65% identity; typically at least 70% or at least 75% identity; more typically at least 80% or at least 85% identity; and even more typically at least 90%, at least 95%, or at least 98% identity (as determined using one of the methods set forth infra).

"Similarity" or "percent similarity" in the context of two or more polypeptide sequences, refer to two or more sequences or subsequences that have a specified percentage of amino acid residues that are the same or conservatively substituted when compared and aligned for maximum correspondence, as measured using one of the methods set forth infra. By way of example, a first amino acid sequence can be considered similar to a second amino acid sequence when the first amino acid sequence is at least 50%, 60%, 70%, 75%, 80%, 90%, or even 95% identical, or conservatively substituted, to the second amino acid sequence when compared to an equal number of amino acids as the number contained in the first sequence, or when compared to an alignment of polypeptides that has been aligned by a computer similarity program known in the art (see infra).

The terms "substantial similarity" or "substantial similarity," in the context of polypeptide sequences, indicates that a polypeptide region has a sequence with at least 70%, typically at least 80%, more typically at least 85%, and even more typically at least 90% or at least 95% sequence similarity to a reference sequence. For example, a polypeptide is substantially similar to a second polypeptide, for example, where the two peptides differ by one or more conservative substitutions.

In the context of anti-CD70 antibodies or derivatives thereof, a protein that has one or more polypeptide regions substantially identical or substantially similar to one or more antigen-binding regions (e.g., a heavy or light chain variable region, or a heavy or light chain CDR) of an anti-CD70 antibody retains specific binding to an epitope of CD70 recognized by the anti-CD70 antibody, as determined using any of various standard immunoassays known in the art or as referred to herein.

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, *Proc. Natl. Acad. Sci. USA* 87:2264-2268, modified as in Karlin and Altschul, 1993, *Proc. Natl. Acad. Sci. USA* 90:5873-5877. Such an algorithm is incorporated into the NBLAST and XBLAST programs of Altschul, et al., 1990, *J. Mol. Biol.* 215:403-410. BLAST nucleotide searches can be performed with the NBLAST program, score=100, wordlength=12 to obtain nucleotide sequences homologous to a nucleic acid encoding a protein of interest. BLAST protein searches can be performed with the XBLAST program, score=50, wordlength=3 to obtain amino acid sequences homologous to protein of interest. To obtain gapped alignments for comparison purposes, Gapped BLAST can be utilized as described in Altschul et al., 1997, *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g.,) XBLAST and NBLAST) can be used. (See, e.g., the NCBI internet web site.) Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, *Comput. Appl. Biosci.* 10:3-5; and FASTA described in Pearson and Lipman, 1988, *Proc. Natl. Acad. Sci.* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. For a further description of FASTA parameters, see, e.g., the documentation at the Pasteur Institute web site, the contents of which are incorporated herein by reference.

Alternatively, protein sequence alignment may be carried out using the CLUSTAL W algorithm, as described by Higgins et al., 1996, *Methods Enzymol.* 266:383-402.

As used herein, the terms "prevention" and "prevent" refer to administration of an anti-CD70 antibody-drug conjugate (ADC) or ADC derivative to a subject before the onset of a clinical or diagnostic symptom of a CD70-expressing cancer or immunological disorder (e.g., administration to an individual with a predisposition or at a high risk of acquiring the CD70-expressing cancer or immunological disorder) to (a) block the occurrence or onset of the CD70-expressing cancer or immunological disorder, or one or more of clinical or diagnostic symptoms thereof, (b) inhibit the severity of onset of the CD70-expressing cancer or immunological disorder, or (c) to lessen the likelihood of the onset of the CD70-expressing cancer or immunological disorder.

As used herein, the terms "treatment" or "treat" refer to slowing, stopping, or reversing the progression of a CD70- expressing cancer or immunological disorder in a subject, as evidenced by a decrease or elimination of a clinical or diagnostic symptom of the disease, by administration of an anti-CD70 ADC or ADC derivative to the subject after the onset of the clinical or diagnostic symptom of the CD70-expressing cancer or immunological disorder at any clinical stage. Treatment can include, for example, a decrease in the severity of a symptom, the number of symptoms, or frequency of relapse.

The term "pharmaceutically acceptable" as used herein means approved by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which a CD70-targeting moiety-drug conjugate is administered.

The term "effective amount," in the context of the administration of an anti-CD70 ADC or ADC derivative, refers to the amount of the ADC or ADC derivative that is sufficient to inhibit the occurrence or ameliorate one or more clinical or diagnostic symptoms of a CD70-expressing cancer or immunological disorder in a subject. An effective amount of an agent is administered according to the methods described herein in an "effective regime." The term "effective regime" refers to a combination of amount of the agent and dosage frequency adequate to accomplish treatment or prevention of a CD70-expressing cancer or immunological disorder.

The abbreviation "AFP" refers to dimethylvaline-valine-dolaisoleuine-dolaproine-phenylalanine-p-phenylenediamine (see Formula XVI infra).

The abbreviation "MMAE" refers to monomethyl auristatin E (see Formula XI infra).

The abbreviation "AEB" refers to an ester produced by reacting auristatin E with paraacetyl benzoic acid (see Formula XX infra)

The abbreviation "AEVB" refers to an ester produced by reacting auristatin E with benzoylvaleric acid (see Formula XXI infra).

The abbreviation "MMAF" refers to dovaline-valine-dolaisoleuine-dolaproine-phenylalanine (see Formula IVIV infra).

The abbreviations "fk" and "phe-lys" refer to the linker phenylalanine-lysine.

The abbreviations "vc" and "val-cit" refer to the linker valine-citrulline.

II. Anti-CD70 Antibodies and Derivatives Thereof

The methods and compositions described herein encompass the use of antibodies, or a derivative thereof, as ADCs that (a) specifically bind to CD70 and (b) when conjugated to a therapeutic agent, the therapeutic agent exerts a cytotoxic, cytostatic or immunosuppressive effect on CD70-expressing cancer cells or activated immune cells. As used herein, the term "derivative," in the context of an anti-CD70 antibody, refers to a molecule that (i) has an antigen-binding region of an anti-CD70 antibody, or a region derived therefrom (e.g., by conservative substitution), and at least one polypeptide region or other moiety heterologous to the anti-CD70 antibody, and (ii) specifically binds to CD70 via the antigen-binding region or region derived therefrom. In specific embodiments, the anti-CD70 antibody is mAb 1F6 or 2F2 or a derivative thereof. In certain aspects, the anti-CD70 antibody or derivative thereof competes with monoclonal antibody 1F6 or 2F2 for binding to CD70.

In typical embodiments, the anti-CD70 antibody or derivative thereof, when conjugated to a cytotoxic agent, exerts a cytotoxic or cytostatic effect on CD70-expressing cancer cells, or, when conjugated to a cytotoxic or immunosuppressive agent, exerts a cytotoxic, cytostatic, or immunosuppressive effect on activated lymphocytes or dendritic cells, for the treatment of a CD70-expressing cancer or an immunological disorder, respectively, in a subject (e.g., the extracellular domain of human CD70).

Anti-CD70 antibodies suitable for use in accordance with the present compositions and methods are typically monoclonal and can include, for example, chimeric (e.g., having a human constant region and mouse variable region), humanized, or human antibodies; single chain antibodies; or the like. The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule.

In certain embodiments, the antibody is an antigen-binding antibody fragment such as, for example, a Fab, a F(ab'), a F(ab')$_2$, a Fd chain, a single-chain Fv (scFv), a single-chain antibody, a disulfide-linked Fv (sdFv), a fragment comprising either a $V_L$ or $V_H$ domain, or fragments produced by a Fab expression library, or a CD70-binding fragments of any of the above antibodies described supra. Antigen-binding antibody fragments, including single-chain antibodies, can comprise the variable region(s) alone or in combination with the entirety or a portion of the following: hinge region, $C_H1$, $C_H2$, $C_H3$ and $C_L$ domains. Also, antigen-binding fragments can comprise any combination of variable region(s) with a hinge region, $C_H1$, $C_H2$, $C_H3$ and $C_L$ domains. Typically, the antibodies are human, rodent (e.g., mouse and rat), donkey, sheep, rabbit, goat, guinea pig, camelid, horse, or chicken. As used herein, "human" antibodies include antibodies having the amino acid sequence of a human immunoglobulin and include antibodies isolated from human immunoglobulin libraries, from human B cells, or from animals transgenic for one or more human immunoglobulin, as described infra and, for example in U.S. Pat. Nos. 5,939,598 and 6,111,166.

The antibodies may be monospecific, bispecific, trispecific, or of greater multispecificity. Multispecific antibodies may be specific for different epitopes of CD70 or may be specific for both CD70 as well as for a heterologous protein. (See, e.g., PCT publications WO 93/17715; WO 92/08802; WO 91/00360; and WO 92/05793; Tutt et al., 1991, J Immunol 147:60-69; U.S. Pat. Nos. 4,474,893; 4,714,681; 4,925, 648; 5,573,920; and 5,601,819; Kostelny et al., 1992, J Immunol 148:1547-1553.) Multispecific antibodies, including bispecific and trispecific antibodies, useful for practicing the methods described herein are antibodies that immunospecifically bind to both CD70 (including but not limited to antibodies that have the CDRs and/or heavy chains of the monoclonal antibodies 2F2 and 1F6) and a second cell surface receptor or receptor complex, such as an immunoglobulin gene superfamily member, a TNF receptor superfamily member, an integrin, a cytokine receptor, a chemokine receptor, a major histocompatibility protein, a lectin (C-type, S-type, or I-type), or a complement control protein. In a typical embodiment, the binding of the portion of the multispecific antibody to the second cell surface molecule or receptor complex enhances the cytotoxic or cytostatic effect of an anti-CD70 antibody-drug conjugate.

In certain specific embodiments, the anti-CD70 antibody is agonistic, non-agonistic or antagonistic with respective to CD70. In another specific embodiment, the anti-CD70 antibody does not block binding of CD70 ligand to CD70. In yet another embodiment, the anti-CD70 antibody or derivative thereof is a blocking antibody (i.e., an antibody that blocks the binding of CD27 to CD70).

In one aspect, an anti-CD70 antibody comprises one or more complementarity determining regions (CDRs) substantially identical or substantially similar to one or more CDR(s) of monoclonal antibody 1F6 (see Table 1). For example, the antibody can include a heavy chain CDR and/or a light chain CDR that is substantially identical or substantially similar to a corresponding heavy chain CDR (H1, H2, or H3 regions) or corresponding light chain CDR (L1, L2, or L3 regions) of mAb 1F6 (SEQ ID NO:6; SEQ ID NO:8; SEQ ID NO:10; SEQ ID NO:16; SEQ ID NO:18; or SEQ ID NO:20, respectively). In typical embodiments, the anti-CD70 antibody has two or three heavy chain CDRs and/or two or three light chain CDRs that are substantially identical or substantially similar to corresponding heavy and/or light chain CDRs of mAb 1F6 . In specific embodiments, a CDR substantially identical or substantially similar to a heavy or light chain CDR of 1F6 has the amino acid sequence set forth in SEQ ID NO:6, SEQ ID NO:8, SEQ ID NO:10, SEQ ID NO:16, SEQ ID NO:18, or SEQ ID NO:20.

For example, in certain embodiments, where an anti-CD70 antibody has at least one heavy chain CDR substantially identical or substantially similar to a heavy chain CDR of mAb 1F6, the antibody or derivative thereof further includes at least one light chain CDR that is substantially identical or substantially similar to a light chain CDR of mAb 1F6.

In certain typical embodiments, an anti-CD70 antibody includes a heavy or light chain variable domain, the variable domain having (a) a set of three CDRs substantially identical or substantially similar to corresponding CDRs of mAb 1F6, and (b) a set of four framework regions. For example, an anti-CD70 antibody can include a heavy or light chain variable domain, the variable domain having (a) a set of three CDRs, in which the set of CDRs are from monoclonal antibody 1F6, and (b) a set of four framework regions, in which the set of framework regions are identical to or different from the set of framework regions in mAb 1F6.

In a specific embodiment, the anti-CD70 antibody includes a heavy chain variable region that is substantially identical or substantially similar to the heavy chain variable region of mAb 1F6 (i.e., substantially identical or substantially similar to the amino acid sequences set forth in SEQ ID NO:2, see Table 1) and/or a light chain variable region that is substantially identical or substantially similar to the light chain variable regions of mAb 1F6 (i.e., substantially identical or substantially similar to the amino acid sequences set forth in SEQ ID NO:12, see Table 1). For example, the antibody can include a heavy chain variable region having the amino acid sequence set forth in SEQ ID NO:2 and, optionally, can further include a light chain variable region having the amino acid sequence set forth in SEQ ID NO:12 . In one exemplary embodiment, the anti-CD70 antibody is mAb 1F6.

In another aspect, an anti-CD70 antibody comprises one or more CDRs substantially identical or substantially similar to one or more CDR(s) of monoclonal antibody 2F2 (see Table 1). For example, the antibody can include a heavy chain CDR and/or a light chain CDR that is substantially identical or substantially similar to a corresponding heavy chain CDR (H1, H2, or H3 regions) or corresponding light chain CDR (L1, L2, or L3 regions) of mAb 2F2 (SEQ ID NO:26, SEQ ID NO:28; SEQ ID NO:30; SEQ ID NO:36, SEQ ID NO:38 or SEQ ID NO:40). In typical embodiments, the anti-CD70 antibody has two or three heavy chain CDRs and/or two or three light chain CDRs that are substantially identical or substantially similar to corresponding heavy and/or light chain CDRs of mAb 2F2 . In specific embodiments, a CDR substantially identical or substantially similar to a heavy or light chain CDR of 2F2 has the amino acid sequence set forth in SEQ ID NO:26, SEQ ID NO:28, SEQ ID NO:30; SEQ ID NO:36, SEQ ID NO:38, or SEQ ID NO:40.

For example, in certain embodiments, where an anti-CD70 antibody has at least one heavy chain CDR substantially identical or substantially similar to a heavy chain CDR of mAb 2F2, the antibody or derivative thereof further includes at least one light chain CDR that is substantially identical or substantially similar to a light chain CDR of mAb 2F2.

In certain typical embodiments, an anti-CD70 antibody includes a heavy or light chain variable domain, the variable domain having (a) a set of three CDRs substantially identical or substantially similar to corresponding CDRs of mAb 2F2, and (b) a set of four framework regions. For example, an anti-CD70 antibody can include a heavy or light chain variable domain, the variable domain having (a) a set of three CDRs, in which the set of CDRs are from monoclonal antibody 2F2, and (b) a set of four framework regions, in which the set of framework regions is identical to or different from the set of framework regions in mAb 2F2.

In a specific embodiment, the anti-CD70 antibody includes a heavy chain variable region that is substantially identical or substantially similar to the heavy chain variable region of mAb 2F2 (i.e., substantially identical or substantially similar to the amino acid sequences set forth in SEQ ID NO:22, see Table 1) and/or a light chain variable region that is substantially identical or substantially similar to the light chain variable regions of mAb 2F2 (i.e., substantially identical or substantially similar to the amino acid sequences set forth in SEQ ID NO:32, see Table 1). For example, the antibody can include a heavy chain variable region having the amino acid sequence set forth in SEQ ID NO:22 and, optionally, can further include a light chain variable region having the amino acid sequence set forth in SEQ ID NO:32 . In one exemplary embodiment, the anti-CD70 antibody is mAb 2F2.

A table indicating the region of 1F6 or 2F2 to which each SEQ ID NO. corresponds is provided below:

TABLE 1

| MOLECULE | NUCLEOTIDE OR AMINO ACID | SEQ ID NO |
|---|---|---|
| 1F6 Heavy Chain Variable Region | Nucleotide | 1 |
| 1F6 Heavy Chain Variable Region | Amino Acid | 2 |
| 1F6 Heavy Chain Signal Peptide | Nucleotide | 3 |
| 1F6 Heavy Chain Signal Peptide | Amino Acid | 4 |
| 1F6 Heavy Chain-CDR1(H1) | Nucleotide | 5 |
| 1F6 Heavy Chain-CDR1(H1) | Amino Acid | 6 |
| 1F6 Heavy Chain-CDR2(H2) | Nucleotide | 7 |
| 1F6 Heavy Chain-CDR2(H2) | Amino Acid | 8 |
| 1F6 Heavy Chain-CDR3(H3) | Nucleotide | 9 |
| 1F6 Heavy Chain-CDR3(H3) | Amino Acid | 10 |
| 1F6 Light Chain Variable Region | Nucleotide | 11 |
| 1F6 Light Chain Variable Region | Amino Acid | 12 |
| 1F6 Light Chain Signal Peptide | Nucleotide | 13 |
| 1F6 Light Chain Signal Peptide | Amino Acid | 14 |
| 1F6 Light Chain-CDR1(L1) | Nucleotide | 15 |
| 1F6 Light Chain-CDR1(L1) | Amino Acid | 16 |
| 1F6 Light Chain-CDR2(L2) | Nucleotide | 17 |
| 1F6 Light Chain-CDR2(L2) | Amino Acid | 18 |
| 1F6 Light Chain-CDR3(L3) | Nucleotide | 19 |
| 1F6 Light Chain-CDR3(L3) | Amino Acid | 20 |
| 2F2 Heavy Chain Variable Region | Nucleotide | 21 |
| 2F2 Heavy Chain Variable Region | Amino Acid | 22 |
| 2F2 Heavy Chain Signal Peptide | Nucleotide | 23 |
| 2F2 Heavy Chain Signal Peptide | Amino Acid | 24 |
| 2F2 Heavy Chain-CDR1(H1) | Nucleotide | 25 |
| 2F2 Heavy Chain-CDR1(H1) | Amino Acid | 26 |
| 2F2 Heavy Chain-CDR2(H2) | Nucleotide | 27 |
| 2F2 Heavy Chain-CDR2(H2) | Amino Acid | 28 |
| 2F2 Heavy Chain-CDR3(H3) | Nucleotide | 29 |
| 2F2 Heavy Chain-CDR3(H3) | Amino Acid | 30 |
| 2F2 Light Chain Variable Region | Nucleotide | 31 |
| 2F2 Light Chain Variable Region | Amino Acid | 32 |
| 2F2 Light Chain Signal Peptide | Nucleotide | 33 |

TABLE 1-continued

| MOLECULE | NUCLEOTIDE OR AMINO ACID | SEQ ID NO |
|---|---|---|
| 2F2 Light Chain Signal Peptide | Amino Acid | 34 |
| 2F2 Light Chain-CDR1(L1) | Nucleotide | 35 |
| 2F2 Light Chain-CDR1(L1) | Amino Acid | 36 |
| 2F2 Light Chain-CDR2(L2) | Nucleotide | 37 |
| 2F2 Light Chain-CDR2(L2) | Amino Acid | 38 |
| 2F2 Light Chain-CDR3(L3) | Nucleotide | 39 |
| 2F2 Light Chain-CDR3(L3) | Amino Acid | 40 |

Anti-CD70 antibodies useful in the methods set forth herein may also be described or specified in terms of their binding affinity to CD70. Typical binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times^{-13}$ M, $10^{-13}$ M, $5\times10^{-14}$ M, $10^{-14}$ M, $5\times10^{-15}$ M, or $10^{-15}$ M.

The antibodies that may be used in the treatment of immunological disorders or CD70-expressing cancers can be generated by any suitable method known in the art. For example, monoclonal antibodies can be prepared using a wide variety of techniques including, e.g., the use of hybridoma, recombinant, and phage display technologies, or a combination thereof. Hybridoma techniques are generally discussed in, for example, Harlow et al., *Antibodies: A Laboratory Manual*, (Cold Spring Harbor Laboratory Press, 2nd ed., 1988); and Hammerling, et al., *In Monoclonal Antibodies and T-Cell Hybridomas*, pp. 563-681 (Elsevier, N.Y., 1981). Examples of phage display methods that can be used to make the anti-CD70 antibodies include, e.g., those disclosed in Brinkman et al., 1995, *J Immunol Methods* 182:41-50; Ames et al., 1995, *J Immunol Methods* 184:177-186; Kettleborough et al., 1994, *Eur J Immunol* 24:952-958; Persic et al., 1997, *Gene* 187:9-18; Burton et al., 1994, *Advances in Immunology* 57:191-280; PCT Application No. PCT/GB91/01 134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108 (the disclosures of which are incorporated by reference herein).

Techniques for generating antibody fragments that recognize specific epitopes are also generally known in the art. For example, Fab and F(ab')$_2$ fragments can be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the $C_H1$ domain of the heavy chain. Techniques to recombinantly produce Fab, Fab' and F(ab')$_2$ fragments can also be employed using, e.g., methods disclosed in PCT publication WO 92/22324; Mullinax et al., 1992, *BioTechniques* 12(6):864-869; and Sawai et al., 1995, AJRI 34:26-34; and Better et al., 1988, *Science* 240:1041-1043 (the disclosures of which are incorporated by reference herein).

Examples of techniques that can be used to produce single-chain Fvs and antibodies include those described in U.S. Pat. Nos. 4,946,778 and 5,258,498; Huston et al., 1991, *Methods in Enzymology* 203:46-88; Shu et al., 1993, *Proc Natl Acad Sci USA* 90:7995-7999; and Skerra et al., 1988, *Science* 240: 1038-1040.

In certain embodiments, the anti-CD70 antibody is a chimeric antibody. A chimeric antibody is a molecule in which different portions of the antibody are derived from different animal species, such as for example antibodies having a variable region derived from a murine monoclonal antibody and a human immunoglobulin constant region. Methods for producing chimeric antibodies are known in the art. (See e.g., Morrison, *Science*, 1985, 229:1202; Oi et al., 1986, *BioTechniques* 4:214; Gullies et al., 1989, *J. Immunol. Methods* 125: 191-202; U.S. Pat. Nos. 5,807,715; 4,816,567; and 4,816, 397.)

An anti-CD70 antibody can also be a humanized antibody. Humanized antibodies are antibody molecules that bind the desired antigen and have one or more CDRs from a non-human species, and framework and constant regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., 1988, *Nature* 332:323). Antibodies can be humanized using a variety of techniques known in the art including, for example, CDR-grafting (EP 0 239 400; PCT publication WO 91/09967; U.S. Pat. Nos. 5,225,539; 5,530,101; and 5,585,089), veneering or resurfacing (EP 0 592 106; EP 0 519 596; Padlan, *Molecular Immunology*, 1991, 28(4/5):489-498; Studnicka et al., 1994, *Protein Engineering* 7(6):805-814; Roguska et al., 1994, *Proc. Natl. Acad. Sci.* 91:969-973), and chain shuffling (U.S. Pat. No. 5,565,332) (all of these references are incorporated by reference herein).

In some embodiments, the antibody is a humanized 1F6 or 2F2 antibody, as disclosed in U.S. Provisional Patent Application No. 60/673,070, filed Apr. 19, 2005; and in PCT International Publication No. WO 2006/113909; the disclosures of which are incorporated by reference herein.

In yet other embodiments, the anti-CD70 antibody is a human antibody. Human antibodies can be made by a variety of methods known in the art including, e.g., phage display methods (see supra) using antibody libraries derived from human immunoglobulin sequences. See also, e.g., U.S. Pat. Nos. 4,444,887 and 4,716,111; and PCT publications WO 98/46645, WO 98/50433, WO 98/24893, WO 98/16654, WO 96/34096, WO 96/33735, and WO 91/10741. In addition, a human antibody recognizing a selected epitope can be generated using a technique referred to as "guided selection," in which a selected non-human monoclonal antibody, e.g., a mouse antibody, is used to guide the selection of a completely human antibody recognizing the same epitope (see, e.g., Jespers et al., 1994, *Bio/technology* 12:899-903). Human antibodies can also be produced using transgenic mice that express human immunoglobulin genes. Monoclonal antibodies directed against the antigen can be obtained from the immunized, transgenic mice using conventional hybridoma technology. For an overview of this technology for producing human antibodies, see Lonberg and Huszar, 1995, *Int. Rev. Immunol.* 13:65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598, 877; U.S. Pat. Nos. 5,413,923; 5,625,126; 5,633,425; 5,569,825; 5,661,016; 5,545,806; 5,814,318; 5,885,793; 5,916,771; and 5,939,598. In addition, companies such as Abgenix, Inc. (now Amgen, Fremont, Calif.) and Medarex (Princeton, N.J.)

can be engaged to provide human antibodies directed against a selected antigen using technology similar to that described above.

As set forth supra, a derivative of an anti-CD70 antibody can also be used in the practice of present methods. Generally, an anti-CD70 antibody derivative comprises an anti-CD70 antibody (including, e.g., an antigen-binding fragment or conservatively substituted polypeptides) and at least one polypeptide region or other moiety heterologous to the anti-CD70 antibody. For example, an anti-CD70 antibody can be modified, e.g., by the covalent attachment of any type of molecule, such that covalent attachment does not prevent the antibody derivative from specifically binding to CD70 via the antigen-binding region or region derived therefrom, or the conjugated drug from exerting (a) a cytostatic or cytotoxic effect on CD70-expressing cancer cells, or (b) a cytostatic, cytotoxic, or immunosuppressive effect on activated lymphocytes. Typical modifications include, e.g., glycosylation, acetylation, pegylation, phosphorylation, amidation, derivatization by known protecting/blocking groups, proteolytic cleavage, linkage to a cellular ligand or other protein, and the like. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In certain embodiments, the antibody derivative is a multimer, such as, for example, a dimer, comprising one or more monomers, where each monomer includes (i) an antigen-binding region of an anti-CD70 antibody, or a polypeptide region derived therefrom (such as, e.g., by conservative substitution of one or more amino acids), and (ii) a multimerizing (e.g., dimerizing) polypeptide region, such that the antibody derivative forms multimers (e.g., homodimers) that specifically bind to CD70 . In typical embodiments, an antigen binding region of an anti-CD70 antibody, or a polypeptide region derived therefrom, is recombinantly or chemically fused with a heterologous protein, wherein the heterologous protein comprises a dimerization or multimerization domain. Prior to administration of the antibody derivative to a subject for the purpose of treating or preventing immunoglicial disorders or CD70-expressing cancers, the derivative is subjected to conditions that allow formation of a homodimer or heterodimer. A heterodimer, as used herein, may comprise identical dimerization domains but different CD70 antigen-binding regions, identical CD70 antigen-binding regions but different dimerization domains, or different CD70 antigen-binding regions and dimerization domains.

Typical dimerization domains are those that originate from transcription factors. In one embodiment, the dimerization domain is that of a basic region leucine zipper ("bZIP"). (See C. Vinson et al., 1989, Science 246:911-916). Useful leucine zipper domains include, for example, those of the yeast transcription factor GCN4, the mammalian transcription factor CCAAT/enhancer-binding protein C/EBP, and the nuclear transform in oncogene products, Fos and Jun. (See Landschultz et al., 1988, Science 240:1759-1764; Baxevanis and Vinson, 1993, Curr. Op. Gen. Devel. 3:278-285; O'Shea et al., 1989, Science 243:538-542.) In another embodiment, the dimerization domain is that of a basic-region helix-loop-helix ("bHLH") protein. (See Murre et al., 1989, Cell 56:777-783 . See also Davis et al., 1990, Cell 60:733-746; Voronova and Baltimore, 1990, Proc Natl Acad Sci USA 87:4722-4726.) Particularly useful hHLH proteins are myc, max, and mac.

In yet other embodiments, the dimerization domain is an immunoglobulin constant region such as, for example, a heavy chain constant region or a domain thereof (e.g., a $C_H 1$ domain, a $C_H 2$ domain, or a $C_H 3$ domain). (See, e.g., U.S. Pat. Nos. 5,155,027; 5,336,603; 5,359,046; and 5,349,053; EP 0 367 166; WO 96/04388.)

Heterodimers are known to form between Fos and Jun (Bohmann et al., 1987, Science 238:1386-1392), among members of the ATF/CREB family (Hai et al., 1989, Genes Dev. 3:2083-2090), among members of the C/EBP family (Cao et al., 1991, Genes Dev. 5:1538-1552; Williams et al., 1991, Genes Dev. 5:1553-1567; Roman et al., 1990, Genes Dev. 4:1404-1415), and between members of the ATF/CREB and Fos/Jun families Hai and Curran, 1991, Proc Natl Acad Sci USA 88:3720-3724). Therefore, when a CD70-binding protein-drug conjugate is administered to a subject as a heterodimer comprising different dimerization domains, any combination of the foregoing may be used.

In other embodiments, an anti-CD70 antibody derivative is an anti-CD70 antibody conjugated to a second antibody (an "antibody heteroconjugate") (see U.S. Pat. No. 4,676,980). Heteroconjugates useful for practicing the present methods comprise an antibody that binds to CD70 (e.g., an antibody that has the CDRs and/or heavy chains of the monoclonal antibodies 2F2 or 1F6) and an antibody that binds to a surface receptor or receptor complex, such as an immunoglobulin gene superfamily member, a TNF receptor superfamily member, an integrin, a cytokine receptor, a chemokine receptor, a major histocompatibility protein, a lectin (C-type, S-type, or I-type), or a complement control protein.

In certain embodiments, the anti-CD70 antibody or derivative thereof competitively inhibits binding of mAb 1F6 or 2F2 to CD70, as determined by any method known in the art for determining competitive binding (such as, e.g., the immunoassays described herein). In typical embodiments, the antibody competitively inhibits binding of 1F6 or 2F2 to CD70 by at least 50%, more typically at least 60%, yet more typically at least 70%, and most typically at least 75%. In other embodiments, the antibody competitively inhibits binding of 1F6 or 2F2 to CD70 by at least 80%, at least 85%, at least 90%, or at least 95%.

Antibodies can be assayed for specific binding to CD70 by any of various known methods. Immunoassays which can be used include, for example, competitive and non-competitive assay systems using techniques such as Western blots, radio-immunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well-known in the art. (See, e.g., Ausubel et al., eds., Short Protocols in Molecular Biology (John Wiley & Sons, Inc., New York, 4th ed. 1999); Harlow & Lane, Using Antibodies: A Laboratory Manual (Cold Spring Harbor Laboratory Press, Cold Spring Harbor, N.Y., 1999.)

Further, the binding affinity of an antibody to CD70 and the off-rate of an antibody CD70 interaction can be determined by competitive binding assays. One example of a competitive binding assay is a radioimmunoassay comprising the incubation of labeled CD70 (e.g., $^3$H or $^{125}$I) with the antibody of interest in the presence of increasing amounts of unlabeled CD70, and the detection of the antibody bound to the labeled CD70 . The affinity of the antibody for CD70 and the binding off-rates can then be determined from the data by Scatchard plot analysis. Competition with a second antibody (such as, e.g., mAb 1F6 or 2F2) can also be determined using radioimmunoassays. In this case, CD70 is incubated with the antibody of interest conjugated to a labeled compound (e.g., $^3$H or $^{125}$I) in the presence of increasing amounts of an unlabeled second antibody. Alternatively, the binding affinity of an antibody to CD70 and the on- and off-rates of an antibody-CD70 interaction can be determined by surface plasmon resonance.

In accordance with the methods described herein, anti-CD70 antibodies or derivatives thereof, when conjugated to a therapeutic agent, can be internalized and accumulate within a CD70-expressing cell, where the therapeutic agent exerts an effect (e.g., a cytotoxic, cytostatic, or immunosuppressive effect). In additional embodiments, anti-CD70 antibodies or derivatives thereof, when conjugated to a therapeutic agent, can be targeted to and accumulate on the membrane of a CD70-expressing cell, where the therapeutic agent exerts an effect (e.g., a cytotoxic, cytostatic, or immunosuppressive effect). In yet other embodiments, anti-CD70 antibodies or derivatives thereof, when conjugated to a therapeutic agent, can be targeted to a biological molecules in a cell (e.g., an inflammatory agent) and accumulate at or adjacent cells secreting or binding the biological molecule, where the therapeutic agent exerts an effect (e.g., a cytotoxic, cytostatic, or immunosuppressive effect).

Whether a given anti-CD70 antibody or derivative, when conjugated to a therapeutic agent, exerts a corresponding therapeutic effect upon binding a CD70-expressing cell can be readily determined, e.g., by (1) incubating CD70-expressing cells independently with the anti-CD70 antibody or derivative thereof, (2) incubating the cells with a secondary reagent that is conjugated to the therapeutic agent and that specifically binds to the antibody or derivative thereof, and (3) assaying the cells for the corresponding therapeutic effect. Multiple antibodies or antibody derivatives can be readily evaluated via such assays using a secondary reagent that specifically binds a polypeptide region shared by each antibody or derivative thereof (e.g., an anti-Ig antibody). For example, an anti-CD70 mAb that binds CD70 and exerts a cytotoxic effect when conjugated to a cytotoxic agent (e.g., an auristatin such as, for example, AFP, MMAF, or MMAE) can be identified by an indirect immunotoxicity assay such as, for example, described by Chun et al., 2003, *Supplement to Clinical Cancer Research*, Vol. 9. Briefly, the cytotoxic agent is conjugated to a secondary antibody (e.g., for murine mAbs, a polyclonal anti-mouse IgG); CD70-expressing cells are incubated with both the primary and cytotoxic agent-conjugated secondary antibody (e.g., in 96-well plates, using hybridoma supernatant for the primary antibody); and primary antibody-dependent cytotoxicity is assessed in a standard cytotoxicity assay (e.g., an MTT cell viability assay). (See id.)

The anti-CD70 antibodies and derivatives thereof that are useful in the present methods can be produced by any method known in the art for the synthesis of proteins, typically, e.g., by recombinant expression techniques. Recombinant expression of an antibody or derivative thereof that binds to CD70 and depletes or inhibits the proliferation of CD70-expressing cells requires construction of an expression vector containing a nucleic acid that encodes the antibody or derivative thereof. Once a nucleic acid encoding such a protein has been obtained, the vector for the production of the protein molecule may be produced by recombinant DNA technology using techniques well known in the art. Standard techniques such as, for example, those described in Sambrook and Russell, *Molecular Cloning: A Laboratory Manual* (Cold Spring Harbor Laboratory Press, Cold Spring Harbor, N.Y., 3rd ed., 2001); Sambrook et al., *Molecular Cloning: A Laboratory Manual* (Cold Spring Harbor Laboratory Press, Cold Spring Harbor, N.Y., 2nd ed., 1989); *Short Protocols in Molecular Biology* (Ausubel et al., John Wiley & Sons, New York, 4th ed., 1999); and Glick & Pasternak, *Molecular Biotechnology: Principles and Applications of Recombinant DNA* (ASM Press, Washington, D.C., 2nd ed., 1998) can be used for recombinant nucleic acid methods, nucleic acid synthesis, cell culture, transgene incorporation, and recombinant protein expression.

For example, for recombinant expression of an anti-CD70 antibody, an expression vector may encode a heavy or light chain thereof, or a heavy or light chain variable domain, operably linked to a promoter. An expression vector may include, for example, the nucleotide sequence encoding the constant region of the antibody molecule (see, e.g., PCT Publication WO 86/05807; PCT Publication WO 89/01036; and U.S. Pat. No. 5,122,464), and the variable domain of the antibody may be cloned into such a vector for expression of the entire heavy or light chain. The expression vector is transferred to a host cell by conventional techniques, and the transfected cells are then cultured by conventional techniques to produce the anti-CD70 antibody. In typical embodiments for the expression of double-chained antibodies, vectors encoding both the heavy and light chains can be co-expressed in the host cell for expression of the entire immunoglobulin molecule.

A variety of prokaryotic and eukaryotic host-expression vector systems can be utilized to express an anti-CD70 antibody or derivative thereof. Typically, eukaryotic cells, particularly for whole recombinant anti-CD70 antibody molecules, are used for the expression of the recombinant protein. For example, mammalian cells such as Chinese hamster ovary cells (CHO), in conjunction with a vector such as the major intermediate early gene promoter element from human cytomegalovirus, is an effective expression system for the production of anti-CD70 antibodies and derivatives thereof (see, e.g., Foecking et al., 1986, *Gene* 45:101; Cockett et al., 1990, *Bio/Technology* 8:2).

Other host-expression systems include, for example, plasmid-based expression systems in bacterial cells (see, e.g., Ruther et al., 1983, *EMBO* 1,2:1791; Inouye & Inouye, 1985, *Nucleic Acids Res.* 13:3101-3109; Van Heeke & Schuster, 1989, *J. Biol. Chem.* 24:5503-5509); insect systems such as, e.g., the use of *Autographa californica* nuclear polyhedrosis virus (AcNPV) expression vector in *Spodoptera frugiperda* cells; and viral-based expression systems in mammalian cells, such as, e.g., adenoviral-based systems (see, e.g., Logan & Shenk, 1984, *Proc. Natl. Acad. Sci. USA* 81:355-359; Bittner et al., 1987, *Methods in Enzymol.* 153:51-544).

In addition, a host cell strain can be chosen that modulates the expression of the inserted sequences, or modifies and processes the gene product in the specific fashion desired. Appropriate cell lines or host systems can be chosen to ensure the correct modification and processing (e.g., glycosylation, phosphorylation, and cleavage) of the foreign protein expressed. To this end, eukaryotic host cells which possess the cellular machinery for proper processing of the primary transcript and gene product can be used. Such mammalian host cells include, for example, CHO, VERO, BHK, HeLa, COS, MDCK, 293, 3T3, and W138.

A stable expression system is typically used for long-term, high-yield production of recombinant anti-CD70 antibody or derivative thereof. For example, cell lines that stably express the anti-CD70 antibody or derivative thereof can be engineered by transformation of host cells with DNA controlled by appropriate expression control elements (e.g., promoter, enhancer, sequences, transcription terminators, polyadenylation sites) and a selectable marker, followed by growth of the transformed cells in a selective media. The selectable marker confers resistance to the selection and allows cells to stably integrate the DNA into their chromosomes and grow to form foci which in turn can be cloned and expanded into cell lines.

A number of selection systems can be used, including, for example, the herpes simplex virus thymidine kinase, hypoxanthineguanine phosphoribosyltransferase, and adenine phosphoribosyltransferase genes, which can be employed in tk⁻, hgprt⁻ or aprt⁻ cells, respectively. Also, antimetabolite resistance can be used as the basis of selection for the following genes: dhfr, which confers resistance to methotrexate; gpt, which confers resistance to mycophenolic acid; neo, which confers resistance to the aminoglycoside G-418; and hygro, which confers resistance to hygromycin. Methods commonly known in the art of recombinant DNA technology can be routinely applied to select the desired recombinant clone, and such methods are described, for example, in *Current Protocols in Molecular Biology* (Ausubel et al. eds., John Wiley & Sons, N.Y., 1993); Kriegler, *Gene Transfer and Expression, A Laboratory Manual* (Stockton Press, N.Y., 1990); *Current Protocols in Human Genetics* (Dracopoli et al. eds., John Wiley & Sons, N.Y., 1994, Chapters 12 and 13); and Colberre-Garapin et al., 1981, *J. Mol. Biol.* 150:1.

The expression levels of an antibody or derivative can be increased by vector amplification. (See generally, e.g., Bebbington & Hentschel, *The Use of Vectors Based on Gene Amplification for the Expression of Cloned Genes in Mammalian Cells in DNA Cloning*, Vol. 3 (Academic Press, New York, 1987).) When a marker in the vector system expressing an anti-CD70 antibody or derivative thereof is amplifiable, an increase in the level of inhibitor present in host cell culture media will select host cells that have increased copy number of a marker gene conferring resistance to the inhibitor. The copy number of an associated antibody gene will also be increased, thereby increasing expression of the antibody or derivative thereof (see Crouse et al., 1983, *Mol. Cell. Biol.* 3:257). Expression levels can also be increased by optimizating the vector, and in particular the nucleic acids encoding the antibody or derivative, for the host organism (e.g., by modifying the codon usage, CpG content, and the like).

Where the anti-CD70 antibody comprises both a heavy and a light chain or derivatives thereof, the host cell may be co-transfected with two expression vectors, the first vector encoding the heavy chain protein and the second vector encoding the light chain protein. The two vectors may contain identical selectable markers which enable equal expression of heavy and light chain proteins. Alternatively, a single vector may be used which encodes, and is capable of expressing, both heavy and light chain proteins. In such situations, the light chain is typically placed before the heavy chain to avoid an excess of toxic free heavy chain (see Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once an anti-CD70 antibody or derivative thereof has has been produced (e.g., by an animal, chemical synthesis, or recombinant expression), it can be purified by any suitable method for purification of proteins, including, for example, by chromatography (e.g., ion exchange or affinity chromatography (such as, for example, Protein A chromatography for purification of antibodies having an intact Fc region)), centrifugation, differential solubility, or by any other standard technique for the purification of proteins. An anti-CD70 antibody or derivative thereof can, for example, be fused to a marker sequence, such as a peptide, to facilitate purification by affinity chromatography. Suitable marker amino acid sequences include, e.g., a hexa-histidine peptide, such as the tag provided in a pQE vector (QIAGEN, Inc., 9259 Eton Avenue, Chatsworth, Calif., 91311), and the "HA" tag, which corresponds to an epitope derived from the influenza hemagglutinin protein (Wilson et al., 1984, *Cell* 37:767), and the "flag" tag.

Once an anti-CD70 antibody or derivative thereof is produced, its ability to exert a cytostatic or cytotoxic effect on CD70-expressing cancer cells (when conjugated to a cytotoxic agent) or an immunosuppressive effect on a CD70-expressing immune cell (when conjugated to an immunosuppressive agent) is determined by the methods described infra or as known in the art.

III. Anti-CD70 Antibody-Drug Conjugates

Compositions useful in the treatment of a CD70-expressing cancer or an immunological disorder comprise anti-CD70 antibody-drug conjugates (ADCs) or anti-CD70 ADC derivatives. An "anti-CD70 ADC" as used herein refers to an anti-CD70 antibody (as described in Section II, supra) conjugated to a therapeutic agent. An "anti-CD70 derivative" as used herein refers to a derivative of an anti-CD70 antibody (as described in Section II, supra) conjugated to a therapeutic agent. In certain embodiments, the ADC comprises an anti-CD70 antibody (e.g., mAb 1F6 or 2F2 or a fragment or derivative thereof, including, for example, a chimeric or humanized form thereof). The ADCs or ADC derivatives as described herein produce clinically beneficial effects on CD70-expressing cells when administered to a subject with a CD70-expressing cancer or an immunological disorder, typically when administered alone but also in combination with other therapeutic agents.

In typical embodiments, the anti-CD70 antibody or derivative thereof is conjugated to a cytotoxic or immunosuppressive agent, such that the resulting ADC or ADC derivative exerts a cytotoxic or cytostatic effect on a CD70-expressing cancer cell, or a cytotoxic, cytostatic, or immunosuppressive effect on an immune cell (e.g., an activated lymphocyte or dendritic cell) when taken up or internalized by the cell. Particularly suitable moieties for conjugation to antibodies or antibody derivatives are chemotherapeutic agents, prodrug converting enzymes, radioactive isotopes or compounds, or toxins. For example, an anti-CD70 antibody or derivative thereof can be conjugated to a cytotoxic agent such as a chemotherapeutic agent (see infra), or a toxin (e.g., a cytostatic or cytocidal agent such as, e.g., abrin, ricin A, pseudomonas exotoxin, or diphtheria toxin). Examples of additional agents that are useful for conjugation to the anti-CD70 molecules are provided infra.

In other embodiments, the anti-CD70 antibody or derivative thereof is conjugated to a pro-drug converting enzyme. The pro-drug converting enzyme can be recombinantly fused to the antibody or derivative thereof or chemically conjugated thereto using known methods. Exemplary pro-drug converting enzymes are carboxypeptidase G2, beta-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Arnon et al., "Monoclonal Antibodies For Immunotargeting Of Drugs In Cancer Therapy," in *Monoclonal Antibodies And Cancer Therapy* (Reisfeld et al. eds., Alan R. Liss, Inc., 1985); Hellstrom et al., "Antibodies For Drug Delivery," in *Controlled Drug Delivery* (Robinson et al. eds., Marcel Dekker, Inc., 2nd ed. 1987); Thorpe, "Antibody Carriers Of Cytotoxic Agents In Cancer Therapy: A Review," in *Monoclonal Antibodies '84: Biological And Clinical Applications* (Pinchera et al. eds., 1985); "Analysis, Results, and Future Prospective of the Therapeutic Use of Radiolabeled Antibody In Cancer Therapy," in *Monoclonal Antibodies For Cancer Detection And Therapy* (Baldwin et al. eds., Academic Press, 1985); and Thorpe et al., 1982, *Immunol. Rev.* 62:119-58 . See also, e.g., PCT publication WO 89/12624.)

In accordance with the methods described herein, the anti-CD70 ADC or ADC derivative is internalized and accumulates within a CD70-expressing cell, where the ADC or ADC derivative exerts a therapeutic effect (e.g., a cytotoxic, cytostatic, or immunosuppressive effect). Methods for determining accumulation and rates of accumulation are found in U.S. Provisional Application Ser. No. 60/400,404, filed Jul. 31, 2002; the disclosure of which is incorporated by reference herein.

Typically, when using an anti-CD70 antibody or derivative thereof conjugated to a therapeutic agent (e.g., a drug or a prodrug converting enzyme), the agent is preferentially active when internalized by cells of the cancer to be treated or by activated immune cells (e.g., activated lymphocytes or dendritic cells). In other embodiments, the anti-CD70 ADC or ADC derivative is not internalized, and the drug is effective to deplete or inhibit CD70-expressing cells by binding to the cell membrane. In yet other embodiments, anti-CD70 antibodies ADC or ADC derivatives thereof can be targeted to a biological molecules in a cell (e g., an inflammatory agent) and accumulate at or adjacent cells secreting or binding the biological molecule, where the therapeutic agent exerts an effect (e.g., a cytotoxic, cytostatic, or immunosuppressive effect).

To minimize activity of the therapeutic agent outside the activated immune cells or CD70-expressing cancer cells, an antibody that specifically binds to cell membrane-bound CD70, but not to soluble CD70, can be used, so that the therapeutic agent is concentrated at the cell surface of the activated immune cell or CD70-expressing cancer cell. Alternatively, in a more typical embodiment, the therapeutic agent is conjugated in a manner that reduces its activity unless it is cleaved off the antibody (e.g., by hydrolysis or by a cleaving agent). In such embodiments, the therapeutic agent is attached to the antibody or derivative thereof with a cleavable linker that is sensitive to cleavage in the intracellular environment of the activated immune cell or CD70-expressing cancer cell but is not substantially sensitive to the extracellular environment, such that the conjugate is cleaved from the antibody or derivative thereof when it is internalized by the activated immune cell or CD70-expressing cancer cell (e.g., in the endosomal or, for example by virtue of pH sensitivity or protease sensitivity, in the lysosomal environment or in a caveolea). (See Section III(A), infra.)

Further, in certain embodiments, the ADC or ADC derivative comprises a therapeutic agent that is charged relative to the plasma membrane, thereby further minimizing the ability of the agent to cross the plasma membrane once internalized by a cell. As used herein, a "charged agent" means an agent that (a) is polarized, such that one region of the agent has a charge relative to the plasma membrane, or (b) has a net charge relative to the plasma membrane.

Typically, the anti-CD70 antibody-drug conjugate (ADC) or ADC derivative is substantially purified (e.g., substantially free from substances that limit its effect or produce undesired side-effects). In certain specific embodiments, the anti-CD70 ADC or ADC derivative is 40% pure, more typically about 50% pure, and most typically about 60% pure. In other specific embodiments, the anti-CD70 ADC or ADC derivative is at least approximately 60-65%, 65-70%, 70-75%, 75-80%, 80-85%, 85-90%, 90-95%, or 95-98% pure. In another specific embodiment, the anti-CD70 ADC or ADC derivative is approximately 99% pure.

A. Linkers

Typically, the ADC or ADC derivative comprises a linker region between the therapeutic agent and the anti-CD70 antibody or derivative thereof. As noted supra, in typical embodiments, the linker is cleavable under intracellular conditions, such that cleavage of the linker releases the therapeutic agent from the antibody in the intracellular environment.

For example, in some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, *Pharm. Therapeutics* 83:67-123). Most typical are peptidyl linkers that are cleavable by enzymes that are present in CD70-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). Other such linkers are described, e.g., in U.S. Pat. No. 6,214,345 . In specific embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT (See, e.g., Thorpe et al., 1987, *Cancer Res.* 47:5924-5931; Wawrzynczak et al., In *Immunoconjugates: Antibody Conjugates in Radioimagery and Therapy of Cancer* (C. W. Vogel ed., Oxford U. Press, 1987 . See also U.S. Pat. No. 4,880,935.)

In yet other specific embodiments, the linker is a malonate linker (Johnson et al., 1995, *Anticancer Res.* 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10):1305-12).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of ADC or ADC derivative, are cleaved when the ADC or ADC derivative present in an extracellular environment (e.g., in plasma). Whether a linker is not substantially sensitive to the extracellular environment can be determined, for example, by incubating independently with plasma both (a) the ADC or ADC derivative (the "ADC sample") and (b) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the ADC sample with that present in control sample, as measured, for example, by high performance liquid chromatography.

In other, non-mutually exclusive embodiments, the linker promotes cellular internalization. In certain embodiments, the linker promotes cellular internalization when conjugated to the therapeutic agent (i.e., in the milieu of the linker-therapeutic agent moiety of the ADC or ADC derivate as described herein). In yet other embodiments, the linker promotes cellular internalization when conjugated to both the therapeutic agent and the anti-CD70 antibody or derivative thereof (i.e., in the milieu of the ADC or ADC derivative as described herein).

A variety of linkers that can be used with the present compositions and methods are described in WO 2004010957 entitled "Drug Conjugates and Their Use for Treating Cancer, An Autoimmune Disease or an Tnfectious Disease" filed Jul. 31, 2003, and U.S. Provisional Application No. 60/400,403, entitled "Drug Conjugates and their use for treating cancer, an autoimmune disease or an infectious disease", filed Jul. 31, 2002 (the disclosure of which is incorporated by reference herein).

In certain embodiments, the linker unit has the following general formula:

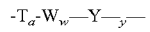

wherein:
-T- is a stretcher unit;
a is 0 or 1;
each —W— is independently an amino acid unit;
w is independently an integer ranging from 2 to 12;
—Y— is a spacer unit; and
y is 0, 1 or 2.

1. The Stretcher Unit

The stretcher unit (-T-), when present, links the anti-CD70 antibody unit to an amino acid unit (—W—). Useful functional groups that can be present on an anti-CD70 antibody, either naturally or via chemical manipulation include, but are not limited to, sulfhydryl, amino, hydroxyl, the anomeric hydroxyl group of a carbohydrate, and carboxyl. Suitable functional groups are sulfhydryl and amino. Sulfhydryl groups can be generated by reduction of the intramolecular disulfide bonds of an anti-CD70 antibody. Alternatively, sulfhydryl groups can be generated by reaction of an amino group of a lysine moiety of an anti-CD70 antibody with 2-iminothiolane (Traut's reagent) or other sulfhydryl generating reagents. In specific embodiments, the anti-CD70 antibody is a recombinant antibody and is engineered to carry one or more lysines. In other embodiments, the recombinant anti-CD70 antibody is engineered to carry additional sulfhydryl groups, e.g., additional cysteines.

In certain specific embodiments, the stretcher unit forms a bond with a sulfur atom of the anti-CD70 antibody unit. The sulfur atom can be derived from a sulfhydryl (—SH) group of a reduced anti-CD70 antibody (A). Representative stretcher units of these embodiments are depicted within the square brackets of Formulas (Ia) and (Ib; see infra), wherein A-, —W—, —Y—, -D, w and y are as defined above and $R^1$ is selected from —$C_1$-$C_{10}$ alkylene-, —$C_3$-$C_8$ carbocyclo-, —O—($C_1$-$C_8$ alkyl)-, -arylene-, —C1-C10 alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O)_r$—, and —($CH_2CH_2O)_r$—$CH_2$—; and r is an integer ranging from 1-10.

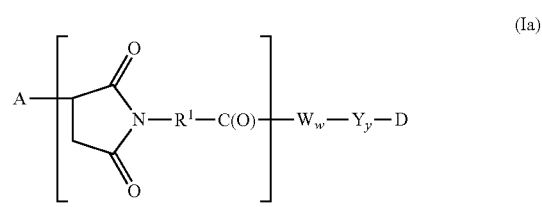

An illustrative stretcher unit is that of formula (Ia) where $R^1$ is —$(CH_2)_5$—:

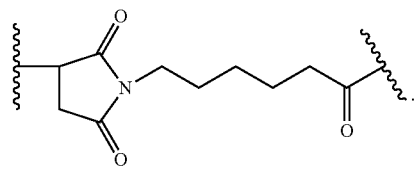 [SMILES: *C(=O)CCCCCN1C(=O)CC(*)C1=O]

Another illustrative stretcher unit is that of formula (Ia) where $R^1$ is —$(CH_2CH_2O)_r$—$CH_2$— and r is 2:

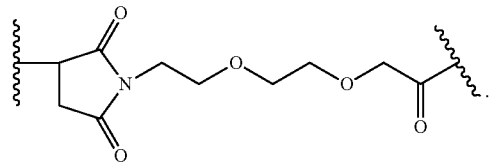 [SMILES: *C(=O)COCCOCCN1C(=O)CC(*)C1=O]

Still another illustrative stretcher unit is that of formula (Ib) where $R^1$ is —$(CH_2)_5$—:

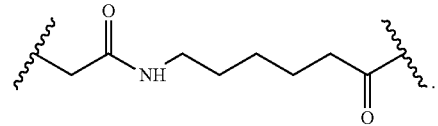 [SMILES: *CC(=O)NCCCCCC(*)=O]

In certain other specific embodiments, the stretcher unit is linked to the anti-CD70 antibody unit (A) via a disulfide bond between a sulfur atom of the anti-CD70 antibody unit and a sulfur atom of the stretcher unit. A representative stretcher unit of this embodiment is depicted within the square brackets of Formula (II), wherein $R^1$, A-, —W—, —Y—, -D, w and y are as defined above.

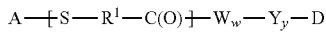 (II)

In other specific embodiments, the reactive group of the stretcher contains a reactive site that can be reactive to an amino group of an anti-CD70 antibody. The amino group can be that of an arginine or a lysine. Suitable amine reactive sites include, but are not limited to, activated esters such as succinimide esters, 4-nitrophenyl esters, pentafluorophenyl esters, anhydrides, acid chlorides, sulfonyl chlorides, isocyanates and isothiocyanates. Representative stretcher units of these embodiments are depicted within the square brackets of Formulas (IIIa) and (IIIb), wherein $R^1$, A-, —W—, —Y—, -D, w and y are as defined above;

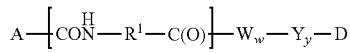 (IIIa)

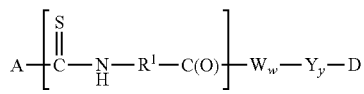 (IIIb)

In yet another aspect, the reactive function of the stretcher contains a reactive site that is reactive to a modified carbohydrate group that can be present on an anti-CD70 antibody. In a specific embodiment, the anti-CD70 antibody is glycosylated enzymatically to provide a carbohydrate moiety. The carbohydrate may be mildly oxidized with a reagent such as sodium periodate and the resulting carbonyl unit of the oxidized carbohydrate can be condensed with a stretcher that contains a functionality such as a hydrazide, an oxime, a reactive amine, a hydrazine, a thiosemicarbazide, a hydrazine carboxylate, or an arylhydrazide such as those described by Kaneko et al., 1991, *Bioconjugate Chem* 2:133-41. Representative stretcher units of this embodiment are depicted within the square brackets of Formulas (IVa)-(IVc), wherein $R^1$, A-, —W—, —Y—, -D, w and y are as defined above.

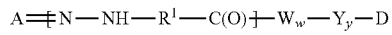 (IVa)

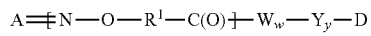 (IVb)

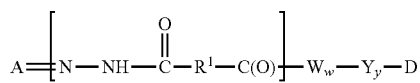 (IVc)

2. The Amino Acid Unit

The amino acid unit (—W—) links the stretcher unit (-T-) to the Spacer unit (—Y—) if the Spacer unit is present, and links the stretcher unit to the cytotoxic or cytostatic agent (Drug unit; D) if the spacer unit is absent.

—$W_w$— is a dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from 2 to 12:

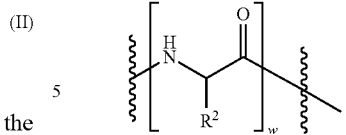

wherein $R^2$ is hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

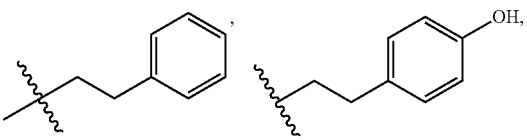

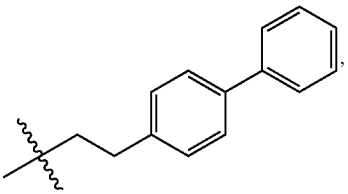

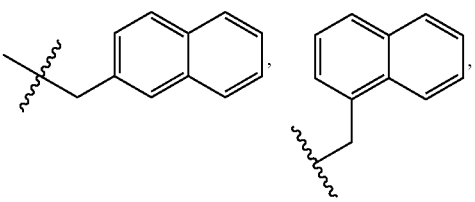

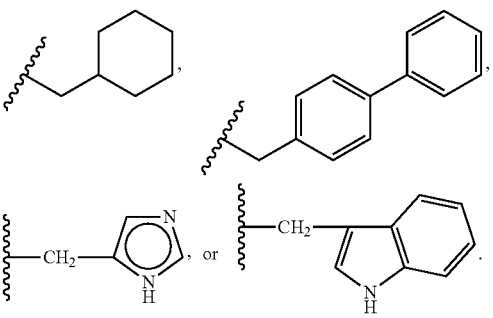

The amino acid unit of the linker unit can be enzymatically cleaved by an enzyme including, but not limited to, a tumor-associated protease to liberate the drug unit (-D) which is protonated in vivo upon release to provide a cytotoxic drug (D).

Illustrative $W_w$ units are represented by formulas (V)-(VII):

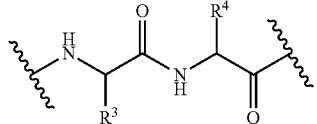
(V)

wherein $R^3$ and $R^4$ are as follows:

| $R^3$ | $R^4$ |
|---|---|
| Benzyl | $(CH_2)_4NH_2$; |
| Methyl | $(CH_2)_4NH_2$; |
| Isopropyl | $(CH_2)_4NH_2$; |
| Isopropyl | $(CH_2)_3NHCONH_2$; |
| Benzyl | $(CH_2)_3NHCONH_2$; |
| Isobutyl | $(CH_2)_3NHCONH_2$; |
| sec-butyl | $(CH_2)_3NHCONH_2$; |
| [indole-CH$_2$] | $(CH_2)_3NHCONH_2$; |
| Benzyl | methyl; and |
| Benzyl | $(CH_2)_3NHC(=NH)NH_2$; |

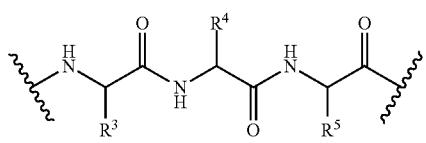
(VI)

wherein $R^3$, $R^4$ and $R^5$ are as follows:

| $R^3$ | $R^4$ | $R^5$ |
|---|---|---|
| Benzyl | benzyl | $(CH_2)_4NH_2$; |
| Isopropyl | benzyl | $(CH_2)_4NH_2$; and |
| H | benzyl | $(CH_2)_4NH_2$; | or

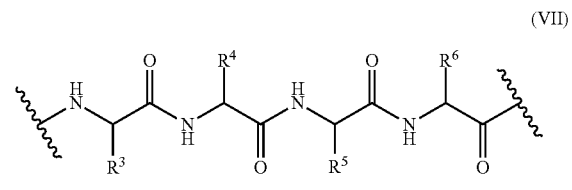
(VII)

wherein $R^3$, $R^4$, $R^5$ and $R^6$ are as follows:

| $R^3$ | $R^4$ | $R^5$ | $R^6$ |
|---|---|---|---|
| H | Benzyl | isobutyl | H; and |
| methyl | Isobutyl | methyl | isobutyl. |

Suitable amino acid units include, but are not limited to, units of formula (V) where: $R^3$ is benzyl and $R^4$ is —$(CH_2)_4NH_2$; $R^3$ is isopropyl and $R^4$ is —$(CH_2)_4NH_2$; $R^3$ is isopropyl and $R^4$ is —$(CH_2)_3NHCONH_2$. Another suitable amino acid unit is a unit of formula (VI), where: $R^3$ is benzyl, $R^4$ is benzyl, and $R^5$ is —$(CH_2)_4NH_2$.

—$W_w$— units can be designed and optimized in their selectivity for enzymatic cleavage by a particular tumor-associated protease. The suitable —Ww- units are those whose cleavage is catalyzed by the proteases, cathepsin B, C and D, and plasmin.

In one embodiment, —$W_w$— is a dipeptide, tripeptide or tetrapeptide unit.

Where $R^2$, $R^3$, $R^4$, $R^5$ or $R^6$ is other than hydrogen, the carbon atom to which $R^2$, $R^3$, $R^4$, $R^5$ or $R^6$ is attached is chiral.

Each carbon atom to which $R^2$, $R^3$, $R^4$, $R^5$ or $R^6$ is attached is independently in the (S) or (R) configuration.

In a certain embodiment, the amino acid unit is a phenylalanine-lysine dipeptide (Phe-Lys or FK linker). In another embodiment, the amino acid unit is a valine-citrulline dipeptide (Val-Cit or VC linker).

3. The Spacer Unit

The spacer unit (—Y—), when present, links an amino acid unit to the drug unit. Spacer units are of two general types: self-immolative and non self-immolative. A non self-immolative spacer unit is one in which part or all of the spacer unit remains bound to the drug unit after enzymatic cleavage of an amino acid unit from the anti-CD70 antibody-linker-drug conjugate or the drug-linker compound. Examples of a non self-immolative spacer unit include, but are not limited to a (glycine-glycine) spacer unit and a glycine spacer unit (both depicted in Scheme 1). When an anti-CD70 antibody-linker-drug conjugate containing a glycine-glycine spacer unit or a glycine spacer unit undergoes enzymatic cleavage via a tumor-cell associated-protease, a cancer-cell-associated protease or a lymphocyte-associated protease, a glycine-glycine-drug moiety or a glycine-drug moiety is cleaved from A-T-$W_w$—. To liberate the drug, an independent hydrolysis reaction should take place within the target cell to cleave the glycine-drug unit bond.

In a typical embodiment, —$Y_y$— is a p-aminobenzyl ether which can be substituted with $Q_m$ where Q is is —$C_1$-$C_8$ alkyl, —$C_1$-$C_8$ alkoxy, -halogen, -nitro or -cyano; and m is an integer ranging from 0-4.

Scheme 1

In one embodiment, a non self-immolative spacer unit ( —Y— ) is -Gly-Gly.

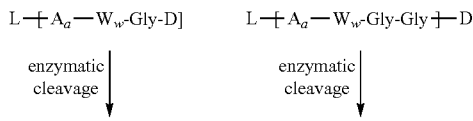

-continued

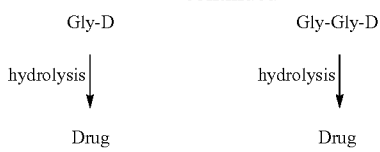

In another embodiment, a non self-immolative the spacer unit (—Y—) is -Gly-.

In one embodiment, the drug-linker compound or an anti-CD70 antibody-linker-drug conjugate lacks a spacer unit (y=0).

Alternatively, an anti-CD70 antibody-linker-drug conjugate containing a self-immolative spacer unit can release the drug (D) without the need for a separate hydrolysis step. In these embodiments, —Y— is a p-aminobenzyl alcohol (PAB) unit that is linked to —$W_w$— via the nitrogen atom of the PAB group, and connected directly to -D via a carbonate, carbamate or ether group (Scheme 2 and Scheme 3).

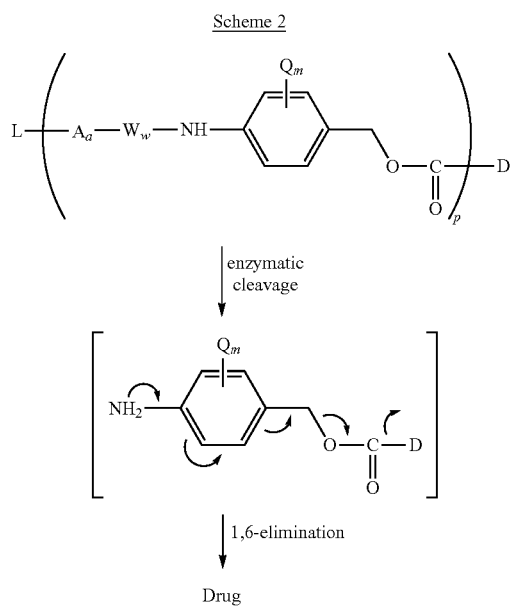

where Q is —$C_1$-$C_8$ alkyl, —$C_1$-$C_8$ alkoxy, -halogen, -nitro or -cyano; m is an integer ranging from 0-4; and p is an integer ranging from 1-20.

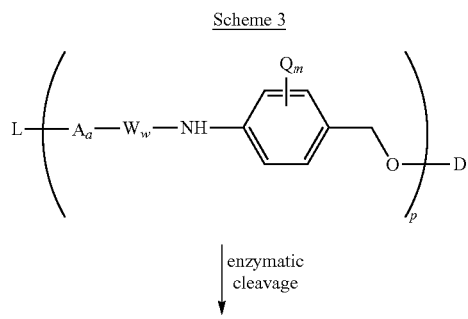

-continued

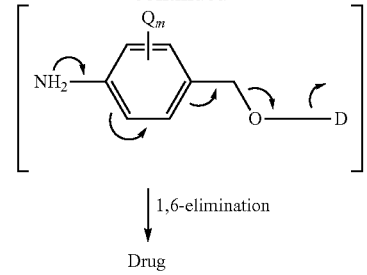

where Q is —$C_1$-$C_8$ alkyl, —$C_1$-$C_8$ alkoxy, -halogen, -nitro or -cyano; m is an integer ranging from 0-4; and p is an integer ranging from 1-20.

Other examples of self-immolative spacers include, but are not limited to, aromatic compounds that are electronically equivalent to the PAB group such as 2-aminoimidazol-5-methanol derivatives (see Hay et al., 1999, *Bioorg. Med. Chem. Lett.* 9:2237 for examples) and ortho or para-aminobenzylacetals. Spacers can be used that undergo facile cyclization upon amide bond hydrolysis, such as substituted and unsubstituted 4-aminobutyric acid amides (Rodrigues et al., 1995, *Chemistry Biology* 2:223), appropriately substituted bicyclo[2.2.1] and bicyclo[2.2.2] ring systems (Storm et al., 1972, *J. Amer. Chem. Soc.* 94:5815) and 2-aminophenyl-propionic acid amides (Amsberry et al., 1990, *J. Org. Chem.* 55:5867). Elimination of amine-containing drugs that are substituted at the α-position of glycine (Kingsbury et al., 1984, *J. Med. Chem.* 27:1447) are also examples of self-immolative spacer strategies that can be applied to the anti-CD70 antibody-linker-drug conjugates.

In an alternate embodiment, the spacer unit is a branched bis(hydroxymethyl)styrene (BHMS) unit (Scheme 4), which can be used to incorporate additional drugs.

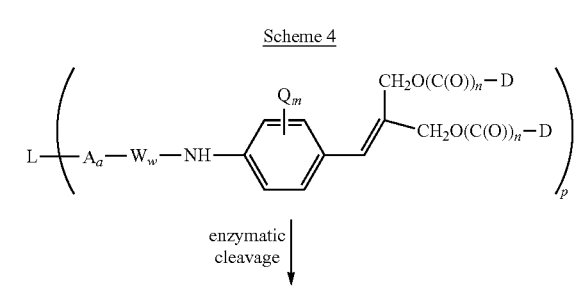

where Q is —$C_1$-$C_8$ alkyl, —$C_1$-$C_8$ alkoxy, -halogen, -nitro or -cyano; m is an integer ranging from 0-4; n is 0 or 1; and p is an integer raging from 1-20.

In one embodiment, the two -D moieties are the same.

In another embodiment, the two -D moieties are different.

Typical spacer units (—$Y_y$—) are represented by Formulas (VIII)-(X):

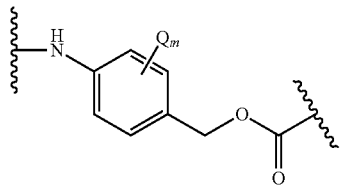

(VIII)

where Q is $C_1$-$C_8$ alkyl, $C_1$-$C_8$ alkoxy, halogen, nitro or cyano; and m is an integer ranging from 0-4;

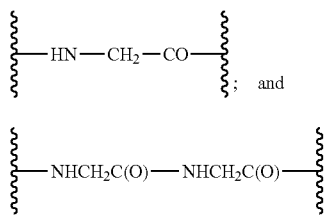

B. Therapeutic Agents

In accordance with the methods described herein, any agent that exerts a therapeutic effect on cancer cells or activated immune cells can be used as the therapeutic agent for conjugation to an anti-CD70 antibody or derivative thereof. (See, e.g., WO 2004/010957, "Drug Conjugates and Their Use for Treating Cancer, An Autoimmune. Disease or an Infectious Disease" (supra) and U.S. Provisional Application No. 60/400,403 (supra)). Typically, the therapeutic agent is a cytotoxic or immunosuppresinve agent. In some embodiments, an anti-CD70 drug conjugate or derivative conjugate comprises from about 1 to about 20 therapeutic agents per conjugate. In some embodiments, an anti-CD70 drug conjugate or derivative conjugate comprises from about 2 to about 10, from about 2 to about 8, about 4 or about 6 therapeutic agents per conjugate.

Useful classes of cytotoxic or immunosuppressive agents include, for example, antitubulin agents, auristatins, DNA minor groove binders, DNA replication inhibitors, alkylating agents (e.g., platinum complexes such as cis-platin, mono (platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic or immunosuppressive agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

In some typical embodiments, the therapeutic agent is a cytotoxic agent. Suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In certain embodiments, the cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to the anti-CD70 antibodies or derivatives thereof.

In specific embodiments, the cytotoxic or cytostatic agent is auristatin E (a derivative of dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin E and its derivatives are described in U.S. patent application Ser. Nos. 09/845,786 (U.S. Patent Application Publication No. 2003-0083263) and 10/001,191 (U.S. Patent Application Publication No. 2005-0009751); International Patent Application No. PCT/US03/24209, International Patent Application No. PCT/US02/13435, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In specific embodiments, the cytotoxic agent is a DNA minor groove binding agent. (See, e.g., U.S. Pat. No. 6,130,237.) For example, in certain embodiments, the minor groove binding agent is a CBI compound. In other embodiments, the minor groove binding agent is an enediyne (e.g., calicheamicin).

In certain embodiments, the ADC or ADC derivative comprises an anti-tubulin. agent. Examples of anti-tubulin agents include, but are not limited to, taxanes (e.g., Taxol® (paclitaxel), Taxotere® (docetaxel)), T67 (Tularik), vinca alkyloids (e.g., vincristine, vinblastine, vindesine, and vinorelbirte), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, Cancer Res. 52:127-131).

In certain embodiments, the therapeutic agent is not a radioisotope. In certain embodiments, the therapeutic agent is not a peptide toxin.

In certain embodiments, the cytotoxic or immunosuppressive agent is an antimetabolite. The antimetabolite can be, for example, a purine antagonist (e.g. azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the cytotoxic or immunosuppressive agent is tacrolimus, cyclosporine or rapamycin. In further embodiments, the cytoxic agent is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin, goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Rituximab, Sargramostim, streptozocin, tamoxifen, temozolomide, teniposide, testolactone, thioguanine, toremifene, Tositumomab, Trastuzumab, tretinoin, uracil mustard, valrubicin, vinblastine, vincristine, vinorelbine or zoledronate.

In additional embodiments, the drug is a humanized anti HER2 monoclonal antibody, RITUXAN (rituximab; Genentech; a chimeric anti CD20 monoclonal antibody); OVAREX (AltaRex Corporation, MA); PANOREX (Glaxo Wellcome, NC; a murine IgG2a antibody); Cetuximab Erbitux (Imclone Systems Inc., NY; an anti-EGFR IgG chimeric antibody); Vitaxin (MedImmune, Inc., MD; Campath UH (Leukosite, MA; a humanized IgG1 antibody); lintuzumab (Protein Design Labs, Inc. and Seattle Genetics, Inc.; a humanized anti-CD33 IgG antibody); LymphoCide™ (Immunomedics, Inc., NJ; a humanized anti-CD22 IgG antibody); Smart ID10 (Protein Design Labs, Inc., CA; a humanized anti-HLA-DR antibody); Oncolym™ (Techniclone, Inc., CA; a radiolabeled murine anti-HLA-Dr10 antibody); Allomune™ (BioTransplant, CA; a humanized anti-CD2 mAb); Avastin™ (Genentech, Inc., CA; an anti-VEGF humanized antibody); Epratuzumab (Immunomedics, Inc., NJ and Amgen, Calif.; an anti-CD22 antibody); CEAcide™ (Immunomedics, NJ; a humanized anti-CEA antibody), or an anti-CD40 antibody (e.g., as disclosed in U.S. Pat. No. 6,838,261).

Other suitable antibodies include, but are not limited to, antibodies against the following antigens: CA125, CA15-3, CA19-9, L6, Lewis Y, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti transferrin receptor, p97, MUC1-KLH, CEA, gp100, MART1, Prostate Specific Antigen, IL-2 receptor, CD20, CD52, CD33, CD22, human chorionic gonadotropin, CD38, CD40, mucin, P21, MPG, and Neu oncogene product.

In certain embodiments, the therapeutic agent is an immunosuppressive agent. The immunosuppressive agent can be, for example, gancyclovir, etanercept, tacrolimus, cyclosporine, rapamycin, cyclophosphamide, azathioprine, mycophenolate mofetil or methotrexate. Alternatively, the immunosuppressive agent can be, for example, a glucocorticoid (e.g., cortisol or aldosterone) or a glucocorticoid analogue (e.g., prednisone or dexamethasone).

In certain typical embodiments, the immunosuppressive agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, or leukotriene receptor antagonists.

Suitable cyclooxygenase inhibitors include meclofenamic acid, mefenamic acid, carprofen, diclofenac, diflunisal, fenbufen, fenoprofen, ibuprofen, indomethacin, ketoprofen, nabumetone, naproxen, sulindac, tenoxicam, tolmetin, and acetylsalicylic acid.

Suitable lipoxygenase inhibitors include redox inhibitors (e.g., catechol butane derivatives, nordihydroguaiaretic acid (NDGA), masoprocol, phenidone, Ianopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylallcanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatrayenoic acid (ETYA), hydroxyphenylretinamide, Ionapalen, esculin, diethylcarbamazine, phenantroline, baicalein, proxicromil, thioethers, diallyl sulfide and di-(1-propenyl)sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitomo SM 15178, American Home Products WAY 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG 14893, Rhone-Poulenc. Rorer RP 66364, Rhone-Poulenc Rorer RP 69698, Shionoogi S-2474, Searle SC-41930, Searle SC-50505, Searle SC-51146, Searle SC-52798, SmithKline Beecham SK&F-104493, Leo Denmark SR-2566, Tanabe T-757 and Teijin TEI-1338.

1. Dolastatin Drugs

In certain embodiments, the cytotoxic or cytostatic agent is a dolastatin. In more specific embodiments, the dolastatin is of the auristatin class. As used herein, the term dolastatin encompasses naturally occurring auristatins and non-naturally occurring derivatives, for example MMAE. Thus, in a specific embodiment, the cytotoxic or cytostatic agent is MMAE (Formula XI). In another specific embodiment, the cytotoxic or cytostatic agent is AFP (Formula XVI).

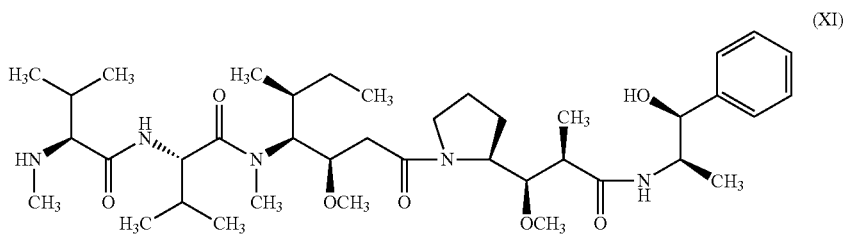 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]
(XI)
In certain embodiments, the cytotoxic or cytostatic agent is a dolastatin of formulas XII-XXI.
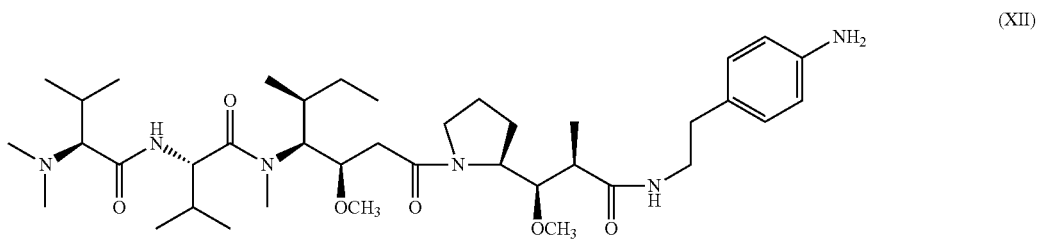
(XII)
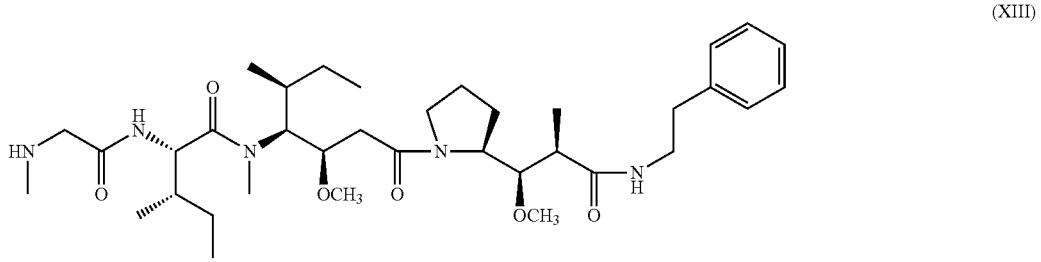
(XIII)
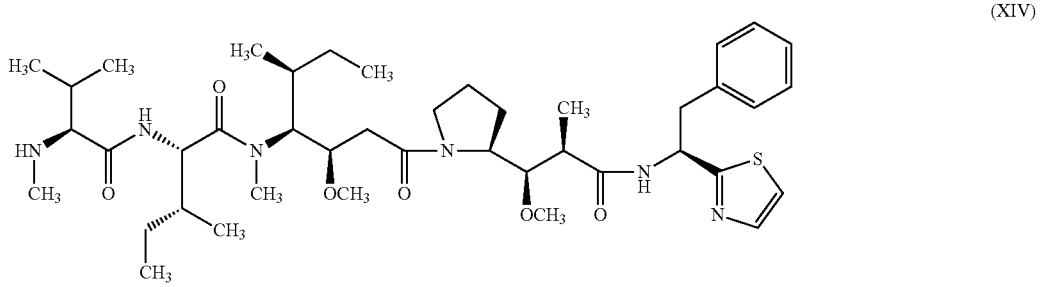
(XIV)
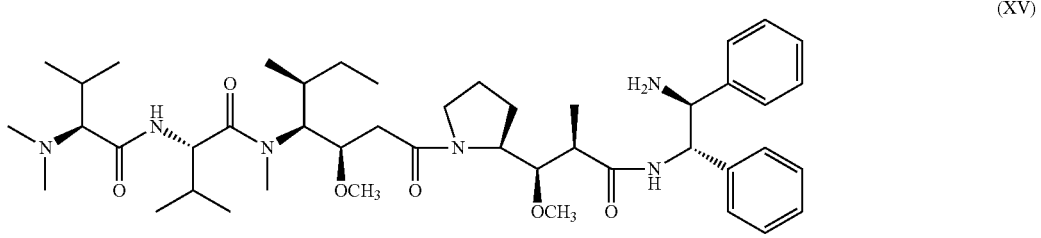
(XV)
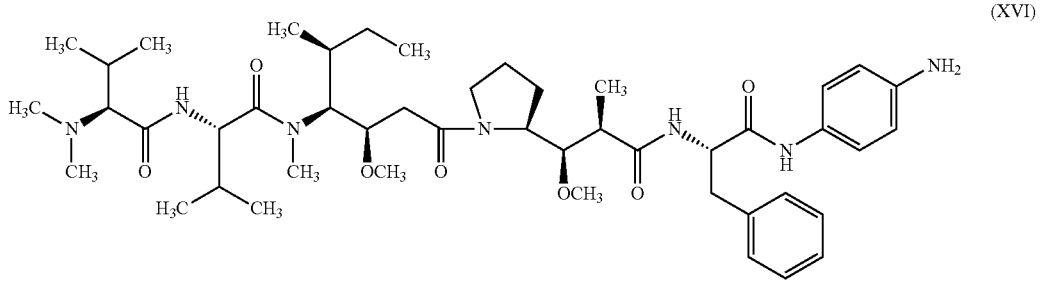
(XVI)

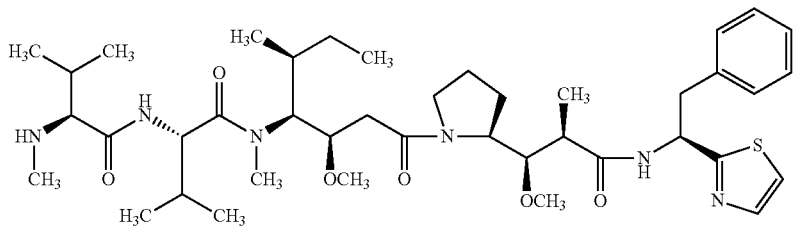

(XVII)

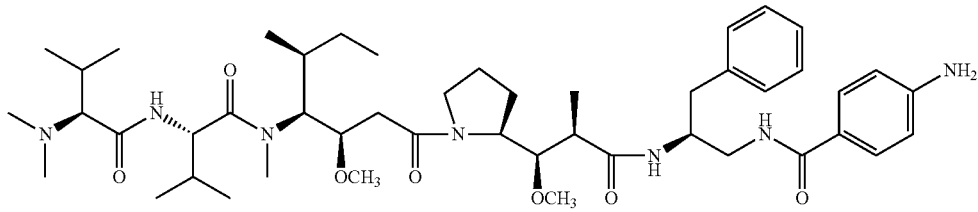

(XVIII)

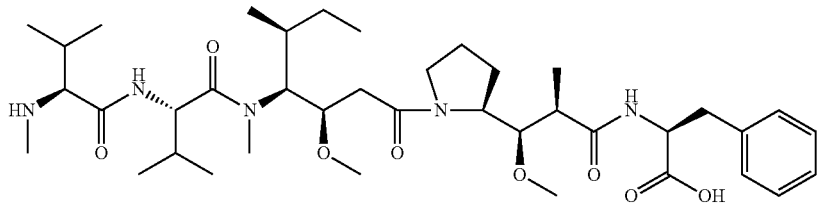

(XVIV)

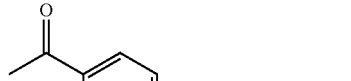

(XX)

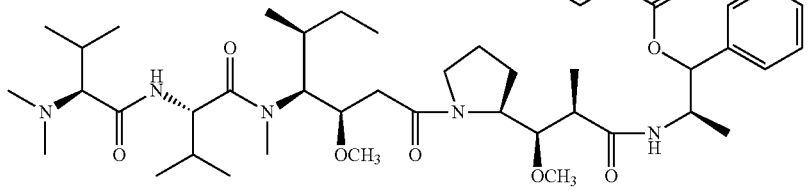

(XXI)

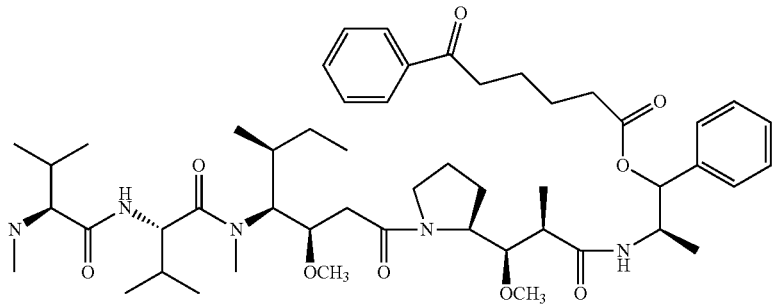

C. Formation of Anti-CD70 ADCs and ADC Derivatives

The generation of anti-CD70 ADCs and ADC derivatives can be accomplished by any technique known to the skilled artisan. Briefly, the anti-CD70 ADCs comprise an anti-CD70 antibody, a drug, and optionally a linker that joins the drug and the antibody. A number of different reactions are available for covalent attachment of drugs to antibodies. This is often accomplished by reaction of the amino acid residues of the antibody molecule, including the amine groups of lysine, the free carboxylic acid groups of glutamic and aspartic acid, the sulthydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of the antibody molecule. Also available for attachment of drugs to antibodies is the Schiff base reaction. This method involves the periodate oxidation of a drug that contains glycol or hydroxy groups, thus forming an aldehyde which is then reacted with the antibody molecule. Attachment occurs via formation of a Schiff base with amino groups of the antibody molecule. Isothiocyanates can also be used as coupling agents for covalently attaching drugs to antibodies. Other techniques are known to the skilled artisan and within the scope of the present invention. Non-limiting examples of such techniques are described in, e.g., U.S. Pat. Nos. 5,665,358; 5,643,573; and 5,556,623, which are incorporated by reference in their entireties herein.

In certain embodiments, an intermediate, which is the precursor of the linker, is reacted with the drug under appropriate conditions. In certain embodiments, reactive groups are used on the drug and/or the intermediate. The product of the reaction between the drug and the intermediate, or the derivatized drug, is subsequently reacted with the anti-CD70 antibody under appropriate conditions.

IV. Other CD70-Targeting Moieties and Protein-Drug Conjugates

As indicated supra, in other embodiments, the CD70-targeting moiety need not be an antibody to be useful in accordance with the methods described herein. Accordingly, a CD70-targeting moiety can include one or more CDRs from an antibody that binds to CD70 and depletes or inhibits the proliferation of CD70-expressing cells when conjugated to a cytotoxic agent, or from an antibody that binds to CD70 and exerts an immunosuppressive effect when conjugated to an immunosuppressive agent. Typically, the protein is a multimer, most typically a dimer.

Further, CD70-binding proteins useful in accordance with the methods provided herein include fusion proteins, i.e., proteins that are recombinantly fused or chemically conjugated (including both covalent and non-covalent conjugation) to heterologous proteins (of typically at least 10, 20, 30, 40, 50, 60, 70, 80, 90 or at least 100 amino acids). The fusion does not necessarily need to be direct, but may occur through linker sequences.

For example, CD70-targeting moieties useful in the present methods can be produced recombinantly by fusing the coding region of one or more of the CDRs of an anti-CD70 antibody in frame with a sequence coding for a heterologous protein. The heterologous protein may provide one or more of the following characteristics: added therapeutic benefits; promote stable expression; provide a means of facilitating high yield recombinant expression; and/or provide a multimerization domain.

In other aspects, CD70-targeting moieties can include CD27 and variants or fragments thereof that bind to CD70 . CD70-targeting moieties can further include peptides, ligands and other molecules that specifically bind to CD70.

CD70-targeting moieties useful in the methods described herein can be identified using any method suitable for screening for protein-protein interactions. Typically, proteins are initially identified by their ability to specifically bind to CD70, then their ability to exert a cytostatic or cytotoxic effect on activated lymphocytes or CD70-expressing cancer cells when conjugated to a cytotoxic or cytostatic agent, or an immunosuppressive effect on an immune cell when conjugated to an immunosuppressive agent. Among the traditional methods which can be employed are "interaction cloning" techniques which entail probing expression libraries with labeled CD70 in a manner similar to the technique of antibody probing of λgt11 libraries. By way of example and not limitation, this can be achieved as follows: a cDNA clone encoding CD70 (or a 1F6 or 2F2 binding domain thereof) is modified at the terminus by inserting the phosphorylation site for the heart muscle kinase (HMK) (see, e.g., Blanar and Rutter, 1992, *Science* 256:1014-1018). The recombinant protein is expressed in *E. coli* and purified on a GDP-affinity column to homogeneity (Edery et al., 1988, *Gene* 74:517-525) and labeled using $\gamma^{32}$P-ATP and bovine heart muscle kinase (Sigma) to a specific activity of $1\times10^8$ cpm/μg, and used to screen a human placenta λgt11 cDNA library in a "far-Western assay" (Blanar and Rutter, 1992, *Science* 256:1014-1018). Plaques which interact with the CD70 probe are isolated. The cDNA inserts of positive λ plaques are released and subcloned into a vector suitable for sequencing, such as pBluescript KS (Stratagene).

One method which detects protein interactions in vivo, the two-hybrid system, is described in detail for illustration purposes only and not by way of limitation. One version of this system has been described (Chien et al., 1991, *Proc. Natl. Acad. Sci. USA* 88:9578-9582) and is commercially available from Clontech (Palo Alto, Calif.).

Once a CD70-binding protein is identified, its ability (alone or when multimerized or fused to a dimerization or multimerization domain) to exert a cytostatic or cytotoxic effect on CD70-expressing cancer cells (when conjugated to a cytotoxic agent) or an immunosuppressive effect on a CD70-expressing immune cell (when conjugated to an immunosuppressive agent) is determined by the methods described infra.

V. Assays for Cytotoxic, Cytostatic, and Immunosuppressive Activities

In accordance with the methods described herein, an anti-CD70 ADC or ADC derivative exerts a cytotoxic or cytostatic effect on a CD70-expressing cancer cell, or a cytotoxic, cytostatic, or immunosuppressive effect on activated CD70-expressing immune cell (e.g., activated lymphocyte or dendritic cell). Activated lymphocytes that can be assayed for a cytotoxic, cytostatic, or immunosuppressive effect of an anti-CD70 ADC or ADC derivative can be cultured cell lines (e.g., CESS, which is available from the ATCC; or KMH2 and L428, both of which are available from Deutsche Sammlung von Mikroorganismen und Zellkulturen GmbH), or from lymphocytes prepared from a fresh blood sample or other sources. Lymphocytes can be activated by the appropriate cocktails of antibodies and cytokines. For example, T lymphocytes can be activated using allogeneic stimulator cells or antigen-pulsed autologous antigen presenting cells and T cell clones can be activated by PHA and cytokines in the presence of feeder cells, as described in Example 9, infra. CD70-expressing cancer cells that can be assayed for a cytotoxic or cytotoxic effect can be tissue culture cell lines as described in Examples 7, infra, or from CD70-expressing cancer cells prepared from a subject.

Once an anti-CD70 ADC or ADC derivative is confirmed as exerting a cytotoxic or cytostatic on CD70-expressing cancer cells or a cytotoxic, cytostatic, or immunosuppressive effect on activated immune cells, its therapeutic value can be validated in an animal model. Exemplary animal models of immunological disorders or CD70-expressing cancers are described in Section VI, infra.

Methods of determining whether an agent exerts a cytostatic or cytotoxic effect on a cell are known. Illustrative examples of such methods are described infra.

For determining whether an anti-CD70 ADC or ADC derivative exerts a cytostatic effect on activated immune cells or CD70-expressing cancer cells, a thymidine incorporation assay may be used. For example, activated immune cells (e.g., activated lymphocytes) or CD70-expressing cancer cells at a density of 5,000 cells/well of a 96-well plated can be cultured for a 72-hour period and exposed to 0.5 μCi of $^3$H-thymidine during the final 8 hours of the 72-hour period, and the incorporation of $^3$H-thymidine into cells of the culture is measured in the presence and absence of the ADC or ADC derivative.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on activated immune cells or CD70 expressing cancer cells indicates that an anti-CD70 ADC or ADC derivative is useful in the treatment or prevention of immunological disorders and CD70-expressing cancers.

Cell viability can be measured by determining in a cell the uptake of a dye such as neutral red, trypan blue, or ALAMAR™ blue (see, e.g., Page et al., 1993, *Intl. J. of Oncology* 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, *J. Nat'l Cancer Inst.* 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, *J. Immunol. Methods* 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in *Biochemica*, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has previously been described by Duke and Cohen, *Current Protocols In Immunology* (Coligan et al. eds., 1992, pp. 3.17.1-3.17.16). Cells can be also labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsining the attached cells, combining the preparations following a centrifugation wash step (e.g., 10 minutes, 2000 rpm), and detecting apoptosis (e.g., by measuring DNA fragmentation). (See, e.g., Piazza et al., 1995, *Cancer Research* 55:3110-16).

Immunosuppressive effects can be measured, for example, by assaying for a cytotoxic or cytostatic effect (as described supra) on an activated immune cell involved in promoting immune responses (e.g., $CD8^+$ cytotoxic T cells, $CD4^+$ Th1 cells, B cells, or mature dendritic cells). In addition or alternatively, an immunosuppressive effect can be determined by examination of the presence or absence of specific immune cell populations (using, e.g., flow cytometry) such as, for example, the presence of T regulatory cells involved in suppression of an immune response; measurement of the functional capacity of immune cells, including, e.g., the cytolytic capacity of cytotoxic T cells; measurements of the cytokines, chemokines, cell surface molecules, antibodies or other secreted or cell-surface molecules of the cells (e.g., by flow cytometry, enzyme-linked immunosorbent assays, Western blot analysis, protein microarray analysis, immunoprecipitation analysis); or measurement of biochemical markers of activation of immune cells or signaling pathways within immune cells (e.g., Western blot and immunoprecipitation analysis of tyrosine, serine or threonine phosphorylation, polypeptide cleavage, and formation or dissociation of protein complexes; protein array analysis; DNA transcriptional profiling using DNA arrays or subtractive hybridization).

VI. Animal Models of Immunological Disorders or CD70-Expressing Cancers

The anti-CD70 ADCs or ADC derivatives can be tested or validated in animal models of immunological disorders or CD70-expressing cancers. A number of established animal models of immunological disorders or CD70-expressing cancers are known to the skilled artisan, any of which can be used to assay the efficacy of the ADC or ADC derivative. Non-limiting examples of such models are described infra.

Some examples for animal models of systemic and organ-specific autoimmune diseases including diabetes, systemic lupus erythematosus, systemic sclerosis, Sjögren's Syndrome, experimental autoimmune encephalomyelitis (multiple sclerosis), thyroiditis, myasthenia gravis, arthritis, uveitis, inflammatory bowel disease have been described by Bigazzi, "Animal Models of Autoimmunity: Spontaneous and Induced," in *The Autoimmune Diseases* (Rose & Mackay eds., Academic Press, 1998) and in "Animal Models for Autoimmune and Inflammatory Disease," in *Current Protocols in Immunology* (Coligan et al. eds., Wiley & Sons, 1997).

Allergic conditions, e.g., asthma and dermatitis, can also be modeled in rodents. Airway hypersensitivity can be induced in mice by ovalbumin (Tomkinson et al., 2001, *J. Immunol.* 166:5792-5800) or Schistosoma mansoni egg antigen (Tesciuba et al., 2001, *J. Immunol.* 167:1996-2003). The Nc/Nga strain of mice show marked increase in serum IgE and spontaneously develop atopic dermatitis-like leisons (Vestergaard et al., 2000, *Mol. Med. Today* 6:209-210; Watanabe et al., 1997, *Int. Immunol.* 9:461-466; Saskawa et al., 2001, *Int. Arch. Allergy Immunol.* 126:239-247).

Injection of immuno-competent donor lymphocytes into a lethally irradiated histo-incompatible host is a classical approach to induce acute GVHD in mice. Alternatively, the parent B6D2F1 murine model provides a system to induce both acute and chronic GVHD. In this model the B6D2F1 mice are F1 progeny from a cross between the parental strains of C57BL/6 and DBA/2 mice. Transfer of DBA/2 lymphoid cells into non-irradiated B6D2F1 mice causes chronic GVHD, whereas transfer of C57BL/6, C57BL/10 or B10.D2 lymphoid cells causes acute GVHD (Slayback et al., 2000, *Bone Marrow Transpl.* 26:931-938; Kataoka et al., 2001, *Immunology* 103:310-318).

Additionally, both human hematopoietic stem cells and mature peripheral blood lymphoid cells can be engrafted into SCID mice, and these human lympho-hematopoietic cells remain functional in the SCID mice (McCune et al., 1988, *Science* 241:1632-1639; Kamel-Reid and Dick, 1988, *Science* 242:1706-1709; Mosier et al., 1988, *Nature* 335:256-259). This has provided a small animal model system for the direct testing of potential therapeutic agents on human lymphoid cells. (See, e.g., Tournoy et al., 2001, *J. Immunol.* 166:6982-6991).

Moreover, small animal models to examine the in vivo efficacies of the anti-CD70 ADCs or ADC derivatives can be created by implanting CD70-expressing human tumor cell lines into appropriate immunodeficient rodent strains, e.g., athymic nude mice or SCID mice. Examples of CD70-expressing human lymphoma cell lines include, for example, Daudi (Ghetie et al., 1994, *Blood* 83:1329-36; Ghetie et al., 1990, *Int J Cancer* 15:481-5; de Mont et al., 2001, *Cancer Res* 61:7654-59), HS-Sultan (Caftan & Maung, 1996, *Cancer Chemother Pharmacol* 38:548-52; Caftan and Douglas, 1994, *Leuk Res* 18:513-22), and Raji (Ochakovskaya et al., 2001, *Clin Cancer Res* 7:1505-10; Breisto et al., 1999, *Cancer Res* 59:2944-49). A non-limiting example of a CD70-expressing Hodgkin's lymphoma line is L428 (Drexler, 1993, *Leukemia and Lymphoma* 9:1-25; Dewan et al., 2005, *Cancer Sci.* 96:466-473). Non-limiting examples of CD70 expressing human renal cell carcinoma cell lines include 786-O (Ananth et al., 1999, *Cancer Res* 59:2210-6; Datta et al., 2001, *Cancer Res* 61:1768-75), ACHN (Hara et al., 2001, *J Urol.* 166:2491-4; Miyake et al., 2002, *J Urol.* 167:2203-8), Caki-1 (Prewett et al., 1998, *Clin. Cancer Res.* 4:2957-66; Shi and Siemann, 2002, *Br. J. Cancer* 87:119-26), and Caki-2 (Zellweger et al., 2001, *Neoplasia* 3:360-7). Non-limiting examples of CD70-expressing nasopharyngeal carcinoma cell lines include C15 and C17 (Busson et al., 1988, *Int. J. Cancer* 42:599-606; Bernheim et al., 1993, *Cancer Genet. Cytogenet.* 66:11-5). Non-limiting examples of CD70-expressing human glioma cell lines include U373 (Palma et al., 2000, *Br. J. Cancer* 82:480-7) and U87MG (Johns et al., 2002, *Int. J. Cancer* 98:398-408). Non-limiting examples of multiple myeloma cell lines include MM.1S (Greenstein et al., 2003, *Experimental Hematology* 31:271-282) and L363 (Diehl et al., 1978, *Blut* 36:331-338). (See also Drexler and Matsuo, 2000, *Leukemia Research* 24:681-703). These tumor cell lines can be established in immunodeficient rodent hosts either as solid tumor by subcutaneous injections or as disseminated tumors by intravenous injections. Once established within a host, these tumor models can be applied to evaluate the therapeutic efficacies of the anti-CD70 ADCs or ADC derivatives as described herein on modulating in vivo tumor growth.

VII. Immune Disorders and CD70-expressing Cancers

The anti-CD70 ADCs and ADC derivatives as described herein are useful for treating or preventing an immunological disorder characterized by inappropriate activation of immune cells (e.g., lymphocytes or dendritic cells). Treatment or prevention of the immunological disorder, according to the methods described herein, is achieved by administering to a subject in need of such treatment or prevention an effective amount of the anti-CD70 ADC or ADC derivative, whereby the ADC or ADC derivative (i) binds to activated immune cells that express CD70 and that are associated with the disease state and (ii) exerts a cytotoxic, cytostatic, or immunosuppressive effect on the activated immune cells.

Immunological diseases that are characterized by inappropriate activation of immune cells and that can be treated or prevented by the methods described herein can be classified, for example, by the type(s) of hypersensitivity reaction(s) that underlie the disorder. These reactions are typically classified into four types: anaphylactic reactions, cytotoxic (cytolytic) reactions, immune complex reactions, or cell-mediated immunity (CMI) reactions (also referred to as delayed-type hypersensitivity (DTH) reactions). (See, e.g., *Fundamental Immunology* (William E. Paul ed., Raven Press, N.Y., 3rd ed. 1993).)

Specific examples of such immunological diseases include the following: rheumatoid arthritis, psoriatic arthritis, autoimmune demyelinative diseases (e.g., multiple sclerosis, allergic encephalomyelitis), endocrine ophthalmopathy, uveoretinitis, systemic lupus erythematosus, myasthenia gravis, Grave's disease, glomerulonephritis, autoimmune hepatological disorder, inflammatory bowel disease (e.g., Crohn's disease), anaphylaxis, allergic reaction, Sjogren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, psoriasis, scleroderma, progressive systemic sclerosis, CREST syndrome (calcinosis, Raynaud's phenomenon, esophageal dysmotility, sclerodactyly, and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, eyelids, chronic cyclitis, heterochronic cyclitis, Fuch's cyclitis, IgA nephropathy, Henoch-Schonlein purpura, graft versus host disease (e.g., following hematopoeitic stem cell transplant), transplantation rejection, cardiomyopathy, Eaton-Lambert syndrome, relapsing polychondritis, cryoglobulinemia, Waldenstrom's macroglobulemia, Evan's syndrome, and autoimmune gonadal failure.

Accordingly, the methods described herein encompass treatment of disorders of B lymphocytes (e.g., systemic lupus erythematosus, Goodpasture's syndrome, rheumatoid arthritis, and type I diabetes), $Th_1$-lymphocytes (e.g., rheumatoid arthritis, multiple sclerosis, psoriasis, Sjorgren's syndrome, Hashimoto's thyroiditis, Grave's disease, primary biliary cirrhosis, Wegener's granulomatosis, tuberculosis, or acute graft versus host disease), or $Th_2$-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of $Th_1$-lymphocytes or $Th_2$-lymphocytes.

In certain embodiments, the immunological disorder is a T cell-mediated immunological disorder, such as a T cell disorder in which activated T cell associated with the disorder express CD70 . ADCs or ADC derivatives can be administered to deplete such CD70-expressing activated T cells. In a specific embodiment, administration of ADCs or ADC derivatives can deplete CD70-expressing activated T cells, while resting T cells are not substantially depleted by the ADC or ADC derivative. In this context, "not substantially depleted" means that less than about 60%, or less than about 70% or less than about 80% of resting T cells are not depleted.

The anti-CD70 ADCs and ADC derivatives as described herein are also useful for treating or preventing a CD70-expressing cancer. Treatment or prevention of a CD70-expressing cancer, according to the methods described herein, is achieved by administering to a subject in need of such treatment or prevention an effective amount of the anti-CD70 ADC or ADC derivative, whereby the ADC or ADC derivative (i) binds to CD70-expressing cancer cells and (ii) exerts a cytotoxic or cytostatic effect to deplete or inhibit the proliferation of the CD70-expressing cancer cells.

CD70-expressing cancers that can be treated or prevented by the methods described herein include, for example, different subtypes of Non-Hodgkin's Lymphoma (indolent NHLs, follicular NHLs, small lymphocytic lymphomas, lymphoplasmacytic NHLs, or marginal zone NHLs); Hodgkin's disease (e.g., Reed-Sternberg cells); cancers of the B-cell lineage, including, e.g., diffuse large B-cell lymphomas, follicular lymphomas, Burkitt's lymphoma, mantle cell lymphomas, B-cell lymphocytic leukemias (e.g., acute lymphocytic leukemia, chronic lymphocytic leukemia); Epstein Barr Virus positive B cell lymphomas; renal cell carcinomas (e.g., clear cell and papillary); nasopharyngeal carcinomas; thymic carcinomas; gliomas; glioblastomas; neuroblastomas; astrocytomas; meningiomas; Waldenstrom macroglobulinemia; multiple myelomas; and colon, stomach, and rectal carcinomas.

In some embodiments, a CD70-expressing cancer has at least about 15,000, at least about 10,000 or at least about 5,000 CD70 molecules/cell.

VIII. Pharmaceutical Compositions Comprising Anti-CD70 ADCs and ADC Derivatives and Administration Thereof In accordance with the present methods, a composition comprising an anti-CD70 ADC or ADC derivative as described herein is administered to a subject having or at risk of having an immunological disorder or a CD70-expressing cancer. The term "subject" as used herein means any mammalian patient to which a CD70-binding protein-drug conjugate may be administered, including, e.g., humans and non-human mammals, such as primates, rodents, and dogs. Subjects specifically intended for treatment using the methods described herein include humans. The ADCs or ADC derivatives can be administered either alone or in combination with other compositions in the prevention or treatment of the immunological disorder or CD70-expressing cancer.

Various delivery systems are known and can be used to administer the anti-CD70 ADC or ADC derivative. Methods of introduction include but are not limited to intradermal, intramuscular, intraperitoneal, intravenous, subcutaneous, intranasal, epidural, and oral routes. The ADCs or ADC derivatives can be administered, for example by infusion or bolus injection, by absorption through epithelial or mucocutaneous linings (e.g., oral mucosa, rectal and intestinal mucosa, and the like) and can be administered together with other biologically active agents such as chemotherapeutic agents. Administration can be systemic or local.

In specific embodiments, the anti-CD70 ADC or ADC derivative composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the ADC or ADC derivative does not absorb are used.

In other embodiments, the ADC or ADC derivative is delivered in a controlled release system. In one embodiment, a pump may be used (see Langer, 1990, *Science* 249:1527-1533; Sefton, 1989, *CRC Crit. Ref Biomed. Eng.* 14:201; Buchwald et al., 1980, *Surgery* 88:507; Saudek et al., 1989, *N. Engl. J. Med.* 321:574). In another embodiment, polymeric materials can be used. (See *Medical Applications of Controlled Release* (Langer & Wise eds., CRC Press, Boca Raton, Fla., 1974); *Controlled Drug Bioavailability, Drug Product Design and Performance* (Smolen & Ball eds., Wiley, New York, 1984); Ranger & Peppas, 1983, *Macromol. Sci. Rev. Macromol. Chem.* 23:61 . See also Levy et al., 1985, *Science* 228:190; During et al., 1989, *Ann. Neurol.* 25:351; Howard et al., 1989, *J. Neurosurg.* 71:105.) Other controlled release systems are discussed, for example, in Langer, supra.

The anti-CD70 ADCs or ADC derivatives are administered as pharmaceutical compositions comprising a therapeutically effective amount of the ADC or ADC derivative and one or more pharmaceutically compatible ingredients. For example, the pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol mono stearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the nucleic acid or protein, typically in purified form, together with a suitable amount of carrier so as to provide the form for proper administration to the patient. The formulations correspond to the mode of administration.

In typical embodiments, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the pharmaceutical can also include a buffering agent (e.g., a phosphate, citrate or amino acid, such as histidine), a solubilizing agent (e.g., nonionic detergents such as a polysorbate, triton, or polyoxamer; or an amino acid) and/or a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

In certain embodiments, the pharmaceutical compositions comprising the anti-CD70 ADC or ADC derivative can further comprise a second therapeutic agent (e.g., a second ADC or ADC derivative or a non-conjugated cytotoxic or immunosuppressive agent such as, for example, any of those described herein).

Further, the pharmaceutical composition can be provided as a pharmaceutical kit comprising (a) a container containing an anti-CD70 ADC or ADC derivative in lyophilized form and (b) a second container containing a pharmaceutically acceptable diluent (e.g., sterile water) for injection. The pharmaceutically acceptable diluent can be used for reconstitution or dilution of the lyophilized ADC or ADC derivative. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the ADC or ADC derivative that is effective in the treatment or prevention of an immunological disorder or CD70-expressing cancer can be determined by stgndard clinical techniques. In addition, in vitro assays may optionally be employed to help identify optimal dosage ranges. The precise dose to be employed in the formulation will also depend on the route of administration, and the stage of immunological disorder or CD70-expressing cancer, and should be decided according to the judgment of the practitioner and each patient's circumstances. Effective doses may be extrapolated from dose-response curves derived from in vitro or animal model test systems.

For example, toxicity and therapeutic efficacy of the ADCs or ADC derivatives can be determined in cell cultures or experimental animals by standard pharmaceutical procedures for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. ADCs or ADC derivatives that exhibit large therapeutic indices are preferred. Where an ADC or ADC derivative exhibits toxic side effects, a delivery system that targets the ADC or ADC derivative to the site of affected tissue can be used to minimize potential damage non-CD70-expressing cells and, thereby, reduce side effects.

The data obtained from the cell culture assays and animal studies can be used in formulating a range of dosage for use in humans. The dosage of the anti-CD70 ADC or ADC derivative typically lies within a range of circulating concentrations that include the $ED_{50}$ with little or no toxicity. The dosage may vary within this range depending upon the dosage form employed and the route of administration utilized. For any ADC or ADC derivative used in the method, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Generally, the dosage of an anti-CD70 ADC or ADC derivative administered to a patient with an immunological disorder or CD70-expressing cancer is typically 0.1 mg/kg to 100 mg/kg of the subject's body weight. More typically, the dosage administered to a subject is 0.1 mg/kg to 50 mg/kg of the subject's body weight, even more typically 1 mg/kg to 30 mg/kg, 1 mg/kg to 20 mg/kg, 1 mg/kg to 15 mg/kg, 1 mg/kg to 12 mg/kg, 1 mg/kg to 10 mg/kg, or 1 mg/kg to 7.5 mg/kg of the subject's body weight. Generally, human antibodies have a longer half-life within the human body than antibodies from other species due to the immune response to the foreign proteins. Thus, lower dosages of ADCs comprising humanized, chimeric or human antibodies and less frequent administration is often possible.

A dose of an anti-CD70 ADC or ADC derivative can be administered, for example, daily, once per week (weekly), twice per week, thrice per week, four times per week, five times per week, biweekly, monthly or otherwise as needed.

In some embodiments, the dosage of an anti-CD70 ADC or ADC derivative corresponds to a sub-optimal dosage (i.e., below the $EC_{50}$ for the anti-CD70 ADC or ADC derivative). For example, the dosage of an anti-CD70 ADC or ADC derivative can comprise a dosage selected from the lowest 25%, lowest 15%, lowest 10% or lowest 5% of the therapeutic window. As used herein, the term "therapeutic window" refers to the range of dosage of a drug or of its concentration in a bodily system that provides safe and effective therapy.

In some embodiments, the dosage of an anti-CD70 ADC or ADC derivative is from about 0.05 mg/kg to about 2 mg/kg, about 0.05 mg/kg to about 1 mg/kg, or about'0.1 mg/kg to about 0.9 mg/kg, or about 0.15 to about 0.75 mg/kg of the subject's body weight. Such a dosage can be administered from 1 to about 15 times per week. Each dose can be the same or different. For example, a dosage of about 0.15 mg/kg of an anti-CD70 ADC or ADC derivative can be administered from 1 to 10 times per four day, five day, six day or seven day period.

The anti-CD70 ADC or ADC derivative can be administered in combination with one or more other therapeutic agents for the treatment or prevention of immunological disorders or CD70-expressing cancers. For example, combination therapy can include a second cytostatic, cytotoxic, or immunosuppressive agent (for example, an unconjugated cytostatic, cytotoxic, or immunosuppressive agent such as those conventionally used for the treatment of cancers or immunological disorders (e.g., standard of care therapies)). Combination therapy can also include, e.g., administration of an agent that targets a receptor or receptor complex other than CD70 on the surface of activated lymphocytes, dendritic cells or CD70-expressing cancer cells. An example of such an agent is a second, non-CD70 antibody that binds to a molecule at the surface of an activated lymphocyte, dendritic cells or CD70-expressing cancer cells. Another example is a ligand that targets such a receptor or receptor complex. Typically, such an antibody or ligand binds to a cell surface receptor on activated lymphocytes, dendritic cells or CD70-expressing cancer cells and enhances the cytotoxic or cytostatic effect of the anti-CD70 antibody by delivering a cytostatic or cytotoxic signal to the activated lymphocytes, dendritic cells or CD70-expressing cancer cells.

In certain embodiments, the therapeutic agent is an anti-VEGF agent, such as AVASTIN (bevacizumab) or NEXAVAR (Sorafenib); a PDGF blocker, such as SUTENT (sunitinib malate); an immunomodulatory agent such as Revlimid (lenalidomide); a cytokine such as G-CSF, GM-CSF or IL-2; VELCADE (bortezomib); a kinase inhibitor, such as NEXAVAR (sorafenib tosylateor); a steroid; or an immunosuppressants, such as Rapamycin (Sirolimus). In some embodiments, the therapeutic agent can be a combined therapy, such as CHOP (Cyclophosphamide, Doxorubicin, Prednisolone and Vincristine), CHOP-R (Cyclophosphamide, Doxorubicin Vincristine, Prednisolone, and rituximab) or ABVD (Doxorubicin, Bleomycin, Vinblastine and Dacarbazine). In other embodiments, the therapeutic agent can be an antibody, such as an anti-CD40 antibody (see, e.g., U.S. Pat. No. 6,838,261) or RITUXAN (Rituximab).

Such combinatorial administration can have an additive or synergistic effect on disease parameters (e.g., severity of a symptom, the number of symptoms, or frequency of relapse).

With respect to therapeutic regimens for combinatorial administration, in a specific embodiment, an anti-CD70 ADC or ADC derivative is administered concurrently with a second therapeutic agent. In another specific embodiment, the second therapeutic agent is administered prior or subsequent to administration of the anti-CD70 ADC or ADC derivative, by at least an hour and up to several months, for example at least an hour, five hours, 12 hours, a day, a week, a month, or three months, prior or subsequent to administration of the ADC or ADC derivative.

The present invention is not to be limited in scope by the specific embodiments described herein. Various modifications of the invention in addition to those described herein will become apparent to those skilled in the art from the foregoing description and accompanying figures. Such modifications are intended to fall within the scope of the appended claims.

The invention is further described in the following examples, which are in not intended to limit the scope of the invention. Cell lines described in the following examples were maintained in culture according to the conditions specified by the American Type Culture Collection (ATCC) or Deutsche Sammlung von Mikroorganismen and Zellkulturen GmbH, Braunschweig, Germany (DMSZ). Cell culture reagents were obtained from Invitrogen Corp., Carlsbad, Calif.

EXAMPLE 1

Sequence Analysis of Anti-CD70 Monoclonal Antibodies 1F6 and 2F2

To determine the cDNA sequences encoding the light ($V_L$) and heavy ($V_H$) chain variable regions of 1F6 and 2F2 mAb, total RNA was isolated from the 1F6 and 2F2 hybridomas using the TRIzol® Reagent (Invitrogen, Carlsbad, Calif.) according to the manufacturer's instructions. The gene-specific primers mIgcK1 5'-CTT CCA CTT GAC ATT GAT GTC TTT G-3' (SEQ ID NO:41) and mIgG1 5'-CAG GTC ACT GTC ACT GGC TCA G-3' (SEQ ID NO:42) were applied to reverse transcribe the light chain variable ($V_L$) and heavy chain variable ($V_H$) first strand cDNAs from both RNA preparations, respectively. First strand cDNA reactions were run using the SuperScript™ First Strand Synthesis System for RT-PCR from Invitrogen (Carlsbad, Calif.). The $V_L$ and $V_H$ cDNAs were then poly-G tailed using terminal deoxynucleotidyl transferase (TdT) (Invitrogen) and the supplied TdT buffer in conditions specified by the manufacturer. Poly-G tailed $V_L$ and $V_H$ first strand cDNAs were then subjected to PCR amplification. The forward primer for both the $V_L$ and $V_H$ PCRs was ANCTAIL 5' GTC GAT GAG CTC TAG AAT TCG TGC CCC CCC CCC CCC C-3' (SEQ ID NO:43). The reverse primer for amplifying the $V_L$ was HBS-mck 5'-CGT CAT GTC GAC GGA TCC AAG CTT CAA GAA GCA CAC GAC TGA GGC AC-3' (SEQ ID NO:44). The reverse primer for amplifying the $V_H$ was HBS-mG1 5'-CGT CAT GTC GAC GGA TCC AAG CTT GTC ACC ATG GAG TTA GTT TGG GC-3' (SEQ ID NO:45). PCRs were run with Ex Taq (Fisher Scientific, Pittsburgh, Pa.) and the supplied reaction buffer in conditions specified by the manufacturer. The $V_L$ and $V_H$ PCR products were then cut by HindIII and EcoRI and cloned into HindIII/EcoRI-cut pUC19. Recombinant plasmid clones were identified, and the nucleotide sequences for the 1F6 and 2F2 hybridomas were determined.

Complementarity determining regions (CDRs) in the heavy and light chains of 1F6 and 2F2 mAbs were determined according to the criteria described in Kabat et al., 1991, *Sequences of Proteins of Immunological Interest*, Washington D.C., US Department of Health and Public Services; Chothia and Lesk, 1987, *J. Mol. Biol.* 196:901-17 (FIGS. 1 and 2). Sequence alignments at both the cDNA and amino acid levels revealed closely related light chain genes were probably utilized in both hybridomas. There is a 92% sequence identity between 1F6 $V_L$ and 2F2 $V_L$ on the amino acid levels. Sequence comparison of the CDRs shows that 1F6 CDR-L1 is identical to 2F2 CDR-L1, only one divergent substitution is present between 1F6 CDR-L2 and 2F2 CDR-L2, and only 2 conservative substitutions are present between 1F6 CDR-L3 and 2F2 CDR-L3 (FIG. 3). On the other hand, a higher degree of sequence diversity is present between 1F6 $V_H$ and 2F2 $V_H$, about 66 of 137 amino acid residues are different between the 2 $V_H$S. Sequence comparison of the CDRs shows that 5 of 10 residues are different between 1F6 CDR-H1 and 2F2 CDR-H1 (3 of the 5 substitutions are divergent), 12 of 17 residues are different between 1F6 CDR-H2 and 2F2 CDR-H2 (9 of the 12 substitutions are divergent), and 5 of 9 residues are different between 1F6 CDR-H3 and 2F2 CDR-H3 (4 of the 5 substitutions are divergent) (FIG. 3).

EXAMPLE 2

Synthesis of Anti-CD70 Drug Conjugates

The ability of anti-CD70 to deliver a potent cytotoxic drug in the form of an antibody drug conjugate (ADC) to eliminate CD70-expressing cells was tested. Monomethyl auristatin E (MMAE), auristatin phenylalanine phenylenediamine (AFP), and monomethyl auristatin phenylalanine (MMAF) were used as the targeted cytotoxic drugs for this study. The drugs were linked to the anti-CD70 mAb 1F6 by the valine-citrulline (vc) dipeptide linker to give the 1F6-vcMMAE, 1F6-vcAFP conjugates and 1F6-vcMMAF.

A. Synthesis of 1F6-vcMMAE

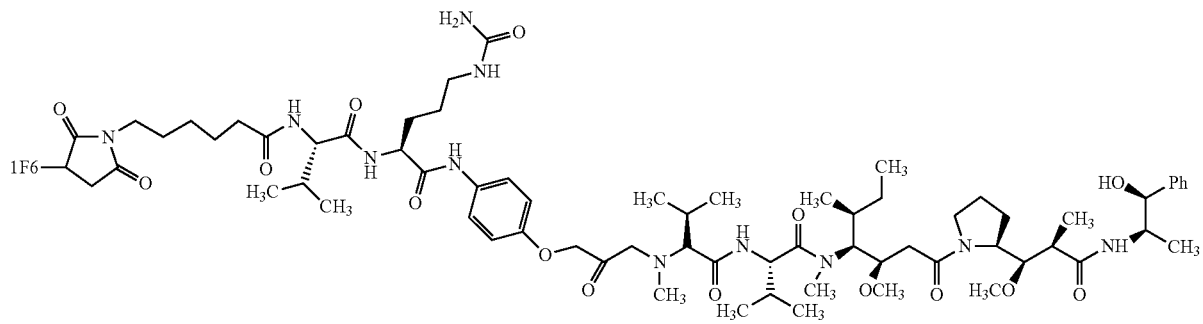

The synthesis of the ADC 1F6-vcMMAE, the general structure of which is depicted above, is described below.

1. Drug-Linker Compound Synthesis

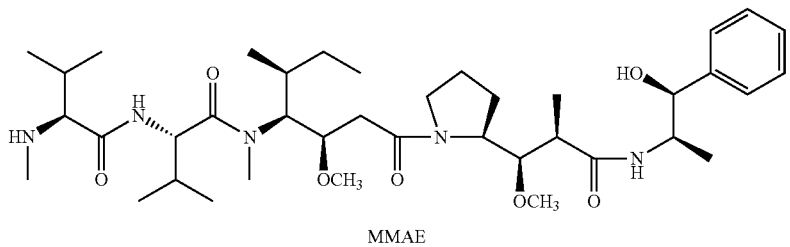 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

MMAE

Synthesis of auristatin E has been previously described (U.S. Pat. No. 5,635,483; Pettit, 1999, *Prog. Chem. Org. Nat. Prod.* 70:1-79). The monomethyl derivative of Auristatin E (MMAE) was prepared by replacing a protected form of monomethylvaline for N,N-dimethylvaline in the synthesis of auristatin E (Senter et al., U.S. Provisional Application No. 60/400,403; and PCT/US03/24209 (supra)).

To prepare the drug-linker compound, MMAE (1.69 g, 2.35 mmol), maleimidocaproyl-L-valine-L-citrulline-p-aminobenzyl alcohol p-nitrophenylcarbonate (2.6 g, 3.52 mmol, 1.5 eq., prepared as described in Dubowchik et al., 2002, *Bioconjugate Chem.* 13:855-869) and HOBt (64 mg, 0.45 mmol, 0.2 eq.) were diluted with DMF (25 mL). After 2 min, pyridine (5 mL) was added and the reaction was monitored using reverse-phase HPLC. The reaction was shown to be complete in 24 hr. The reaction mixture was concentrated to provide a dark oil, which was diluted with 3 mL of DMF. The MT solution was purified using flash column chromatography (silica gel, eluant gradient:100% dichloromethane to 4:1 dichloromethane-MeOH). The relevant fractions were combined and concentrated to provide an oil that solidified under high vacuum to provide a mixture of the desired drug-linker compound and unreacted MMAE as a dirty yellow solid ($R_f$ 0.40 in 9:1 dichloromethane-MeOH). The dirty yellow solid was diluted with DMF and purified using reverse-phase preparative-HPLC (Varian Dynamax C18 column 41 4 mm×25 cm, 8μ, 100 Å, using a gradient run of MeCN and 0.1% aqueous TFA at 45 mL/min from 10% to 100% over 40 min followed by 100% MeCN for 20 min) to provide the desired drug-linker compound as an amorphous white powder (Rf 0.40 in 9:1 dichloromethane-MeOH) which was >95% pure by HPLC and which contained less than 1% of MMAE. Yield: 1.78 g (57%); ES-MS m/z 1316.7 [M+H]+; UV $\lambda_{max}$ 215, 248 nm.

2. Conjugate Preparation

Antibody Reduction. To 0.7 mL 1F6 (10 mg/mL) was added 90 μL of 500 mM sodium borate/500 mM NaCl, pH 8.0, followed by 90 μL of 100 mM DTT in water, and 20 μL of $H_2O$. After incubation at 37° C. for 30 min, the buffer was exchanged by elution over G25 resin equilibrated and eluted with PBS containing 1 mM DTPA (Aldrich). The thiol/Ab value was found to be 9.8 by determining the reduced antibody concentration from the solution's 280 nm absorbance, and the thiol concentration by reaction with DTNB (Aldrich) and determination of the absorbance at 412 nm.

Conjugation of the Reduced Antibody. The reduced mAb was chilled on ice. The drug-linker compound was used as a DMSO solution of known concentration, and the quantity of drug-linker added to the reaction mixture was calculated as follows: L stock solution=V×[Ab]×Fold Excess/[Drug-Linker], where V and [Ab] are the volume and molar concentration of the reduced antibody solution, respectively. 0.904 μL cold $H_2O$ was added to the reduced antibody solution, followed by 500 μL cold acetonitrile. 30.5 μL of 10.2 mM drug-linker compound stock solution was diluted into 1.47 mL acetonitrile. The acetonitrile drug-linker solution was chilled on ice, then added to the reduced antibody solution. The reaction was terminated after 0.5 hr by the addition of a 20 fold molar excess of cysteine over maleimide. The reaction mixture was concentrated by centrifugal ultrafiltration and purified by elution through de-salting G25 in PBS at 4° C. 1F6-vcMMAE was then filtered through 0.2 micron filters under sterile conditions and immediately frozen at −80° C. 1F6-vcIVIMAE was analyzed for 1) concentration, by LTV absorbance; 2) aggregation, by size exclusion chromatography; 3) drug/Ab, by measuring unreacted thiols with DTNB, and 4) residual free drug, by reverse phase HPLC.

B. Synthesis of 1F6-vcAFP

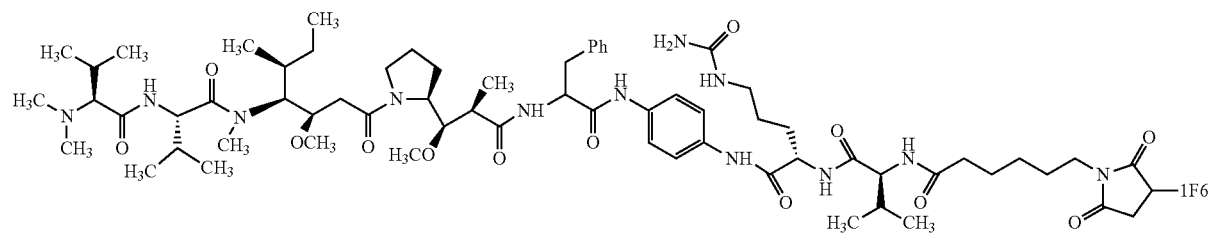

The synthesis of the ADC 1F6-vcAFP, the general structure of which is depicted above, is described below.

1. AFF Synthesis

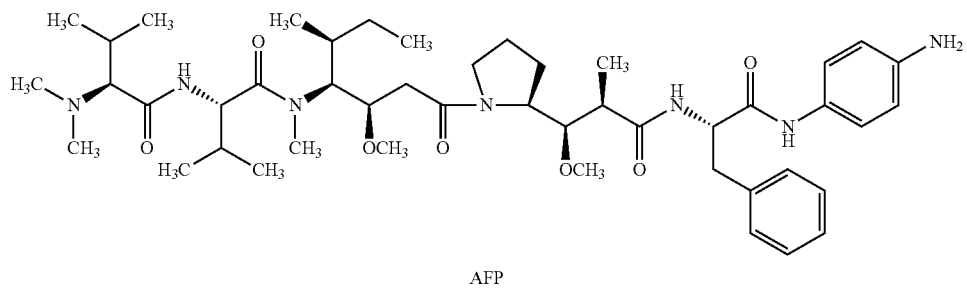 [SMILES: CC[C@H](C)[C@@H]([C@@H](CC(=O)N1CCC[C@H]1[C@H](OC)[C@@H](C)C(=O)N[C@@H](Cc1ccccc1)C(=O)Nc1ccc(N)cc1)OC)N(C)C(=O)[C@@H](NC(=O)[C@H](C(C)C)N(C)C)C(C)C]

AFP

Boc-phenylalanine (1.0 g, 3.8 mmol) was added to a suspension of 1,4-diaminobenzene•HCl (3.5 g, 19.0 mmol, 5.0 eq.) in triethylamine (10.7 mL, 76 0 mmol, 20 eq.) and dichloromethane (50 mL). To the resulting solution was added DEPC (3.2 mL, 19.0 mmol, 5.0 eq.) via syringe. HPLC showed no remaining Boc-phe after 24 hr. The reaction mixture was filtered, and the filtrate was concentrated to provide a dark solid. The dark solid residue was partitioned between 1:1 EtOAc-water, and the EtOAc layer was washed sequentially with water and brine. The EtOAc layer was dried and concentrated to provide a dark brown/red residue that was purified using HPLC (Varian Dynamax column 41.4 mm×25 cm, 5µ, 100 Å using a gradient run of MeCN and water at 45 mL/min form 10% to 100% over 40 min followed by 100% MeCN for 20 min). The relevant fractions were combined and concentrated to provide a red-tan solid intermediate. Yield: 1.4 g (100%); ES-MS m/z 355.9 [M+H]+; UV λmax 215, 265 nm; $^1$H NMR (CDCl3) δ 7.48 (1 H, br s), 7.22-7.37 (5 H, m), 7.12 (2 H, d, J=8.7 Hz), 7.61 (2 H, d, J=8.7 Hz), 5.19 (1 H, br s), 4.39-4.48 (1 H, m), 3.49 (2 H, s), 3.13 (2 H, d, J=5.7 Hz), 1.43 (9 H, s).

The red-tan solid intermediate (0.5 g, 1.41 mmol) and diisopropylethylamine (0.37 mL, 2.11 mmol, 1.5 eq.) were diluted with dichloromethane (10 ml), and to the resulting solution was added Fmoc-Cl (0.38 g, 1.41 mmol). The reaction was allowed to stir, and a white solid precipitate formed after a few minutes. The reaction was complete according to HPLC after 1 hr. The reaction mixture was filtered, and the filtrate was concentrated to provide an oil. The oil was precipitated with EtOAc, resulting in a reddish-white intermediate product, which was collected by filtration and dried under vacuum. Yield: 0.75 g (93%); ES-MS m/z 578.1 [M+H]+, 595.6 [M+NH$_4$]+.

The reddish-white intermediate (0.49 g, 0.85 mmol), was diluted with 10 mL of dichloromethane, and then treated with 5 mL of trifluoroacetic acid. The reaction was complete in 30 min according to reverse-phase HPLC. The reaction mixture was concentrated and the resulting residue was precipitated with ether to provide an off-white solid. The off-white solid was filtered and dried to provide an amorphous powder, which was added to a solution of Boc-Dolaproine (prepared as described in Tetrahedron, 1993, 49(9):1913-1924) (0.24 g, 0.85 mmol) in dichloromethane (10 mL). To this solution was added triethylamine (0.36 mL, 2.5 mmol, 3.0 eq.) and PyBrop (0.59 g, 1.3 mmol, 1.5 eq.). The reaction mixture was monitored using reverse-phase HPLC. Upon completion, the reaction mixture was concentrated, and the resulting residue was diluted with EtOAc, and sequentially washed with 10% aqueous citric acid, water, saturated aqueous sodium bicarbonate, water, and brine. The EtOAc layer was dried (MgSO$_4$), filtered, and concentrated. The resulting residue was purified using flash column chromatography (silica gel) to provide an off-white powdered intermediate. Yield: 0.57 g (88%); ES-MS m/z 764.7 [M+NH$_4$]+; UV λ$_{max}$ 215, 265 nm; $^1$H NMR (DMSO-d$_6$) δ 10.0-10.15 (1 H, m), 9.63 (1 H, br s), 8.42 (½H, d, J=8.4 Hz), 8.22 (½H, d, J=8.4 Hz), 7.89 (2 H, d, J=7.2 Hz), 7.73 (2 H, d, J=7.6 Hz), 7.11-7.55 (13 H, m), 4.69-4.75 (1 H, m), 4.46 (2 H, d, J=6.8 Hz), 4.29 (1 H, t, J=6.4 Hz), 3.29 (3 H, s), 2.77-3.47 (7 H, m), 2.48-2.50 (3 H, m), 2.25 (⅔H, dd, J=9.6, 7.2 Hz), 1.41-1.96 (4 H, m), 1.36 (9 H, s), 1.07 (1 H, d, J=6.4 Hz, rotational isomer), 1.00 (1 H, d, J=6.4 Hz, rotational isomer).

The white solid intermediate (85 mg, 0.11 mmol) and N-Methylval-val-dil-O-t-butyl (55 mg, 0.11 mmol, prepared as described in Pettit et al. 1996, J. Chem. Soc. Perk I p. 859) were diluted with dichloromethane (5 mL), and then treated with 2.5 mL of trifluoroacetic acid under a nitrogen atmosphere for two hours at room temperature. The reaction completion was confirmed by RP-HPLC. The solvent was removed in vacuo and the resulting residue was azeotropically dried twice with toluene, and then dried under high vacuum for 12 hours.

The residue was diluted with dichloromethane (2 mL), diisopropylethylamine (3 eq.) was added, followed by DEPC (1.2 eq.). After the reaction was completed, the reaction mixture was concentrated under reduced pressure, the resulting residue was diluted with EtOAc, and washed sequentially with 10% aqueous citric acid, water, saturated aqueous sodium bicarbonate, and brine. The EtOAc layer was dried, filtered and concentrated to provide a yellow oil.

The yellow oil was diluted with dichloromethane (10 mL) and to the resulting solution diethylamine (5 mL) was added. According to HPLC, reaction was completed after 2 hr. The reaction mixture was concentrated to provide an oil. The oil was diluted with DMSO, and the DMSO solution was purified using reverse phase preparative-HPLC (Varian Dynamax column 21.4 min×25 cm, 5µ, 100 Å, using a gradient run of MeCN and 0.1% TFA at 20 mL/min from 10% to 100% over 40 min followed by 100% MeCN for 20 min) The relevant fractions were combined and concentrated to provide the desired drug as an off-white solid. Overall yield: 42 mg (44% overall); ES-MS m/z 837.8 [M+H]+, 858.5 [M+Na]+; UV λ$_{max}$ 215, 248 nm.

2. Preparation of Drug-Linker Compound

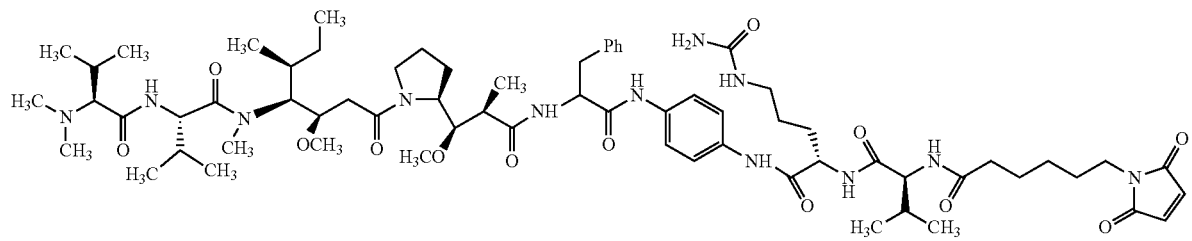 [SMILES: CC[C@H](C)[C@@H]([C@@H](CC(=O)N1CCC[C@H]1[C@H](OC)[C@@H](C)C(=O)NC(Cc1ccccc1)C(=O)Nc1ccc(NC(=O)[C@H](CCCNC(N)=O)NC(=O)[C@@H](NC(=O)CCCCCN2C(=O)C=CC2=O)C(C)C)cc1)OC)N(C)C(=O)[C@@H](NC(=O)[C@H](C(C)C)N(C)C)C(C)C]

The trifluoroacetate salt of AFP (0.37 g, 0.39 mmol, 1.0 eq.) and Fmoc-val-cit (0.30 g, 0.58 mmol, 1.5 eq., prepared according to Dubowchik et al., 2002, *Bioconjugate Chem.* 13:855-896) were diluted with DMF (5 mL, 0.1 M), and to the resulting solution was added pyridine (95 µL, 1.2 mmol, 3.0 eq.). HATU (0.23 g, 0.58 mmol, 1.5 eq.) was then added as a solid, and the reaction mixture was allowed to stir under argon atmosphere while being monitored using HPLC. The reaction progressed slowly, and 4 hr later, 1.0 eq. of diisopropylethylamine was added. The reaction was complete in 1 hr. The reaction mixture was concentrated in vacuo and the resulting residue was purified using prep-HPLC (Varian Dynamax C18 column 41.4 mm×25 cm, 5µ, 100 Å, using a gradient run of MeCN and 0.1% aqueous TFA at 45 mL/min from 10% to 100% over 40 min followed by 100% MeCN for 20 min) to provide a faint pink solid intermediate.

The pink solid intermediate was diluted with DMF (30 mL) and to the resulting solution was added diethylamine (15 mL). Reaction was complete by HPLC in 2 hr. The reaction mixture was concentrated and the resulting residue was washed twice with ether. The solid intermediate was dried under high vacuum and then used directly in the next step.

The solid intermediate was diluted with DMF (20 mL) and to the resulting solution was added 6-(2,5-dioxy-2,5-dihydro-pyrrol-1-yl)-hexanoic acid 2,5-dioxy-pyrrolidin-1-yl ester (0.12 g, 0.39 mmol, 1.0 eq.) (EMCS, Molecular Biosciences Inc., Boulder, Colo.). After 4 days, the reaction mixture was concentrated to provide an oil which was purified using prep-HPLC (Varian Dynamax C18 column 41.4 mm×25 cm, 5µ, 100 Å, using a gradient run of MeCN and 0.1% aqueous TFA at 45 mL/min from 10% to 100% over 40 min followed by 100% MeCN for 20 min) to provide the desired drug-linker compound as a white flaky solid. Yield: 0.21 g (38% overall); ES-MS m/z 1285.9 [M+H]$^+$; 13.07.8 [M+Na]$^+$; UV $\lambda_{max}$ 215, 266 nm.

3. Conjugate Preparation

Antibody Reduction. To 0.48 mL 1F6 (10.4 mg/mL) was added 75 µL of 500 mM sodium borate/500 mM NaCl, pH 8.0, followed by 75 µL of 100 mM DTT in water, and 20 µL PBS. After incubation at 37° C. for 30 min, the buffer was exchanged by elution over G25 resin equilibrated and eluted with PBS containing 1 mM DTPA (Aldrich). The thiol/Ab value was found to be 10.3 by determining the reduced antibody concentration from the solution's 280 nm absorbance, and the thiol concentration by reaction with DTNB (Aldrich) and determination of the absorbance at 412 nm.

Conjugation of the Reduced Antibody. The reduced mAb was chilled on ice. The drug-linker compound was used as a DMSO solution of known concentration, and the quantity of drug-linker added to the reaction mixture was calculated as follows: L stock solution=V×[Ab]×Fold Excess/[Drug-Linker], where V and [Ab] are the volume and molar concentration of the reduced antibody solution, respectively. 984 µL cold PBS/DTPA was added to the reduced antibody solution, followed by 400 µL acetonitrile, and the mixture chilled on ice. 26.4 µL of 8.3 mM drug-linker compound stock solution was then added to the reduced antibody/DMSO solution. The reaction was terminated after 1 hr by the addition of a 40 µL of 100 mM cysteine. The reaction mixture was concentrated by centrifugal ultrafiltration and purified by elution through de-salting G25 in PBS at 4° C. 1F6-vcAFP was then filtered through 0.2 micron filters under sterile conditions and immediately frozen at −80° C. 1F6-vcAFP was analyzed for 1) concentration, by UV absorbance; 2) aggregation, by size exclusion chromatography; 3) dmg/Ab, by measuring unreacted thiols by treatment with DTT, followed by DTNB, and 4) residual free drug, by reverse phase HPLC.

C. Synthesis of 1F6-vcMMAF

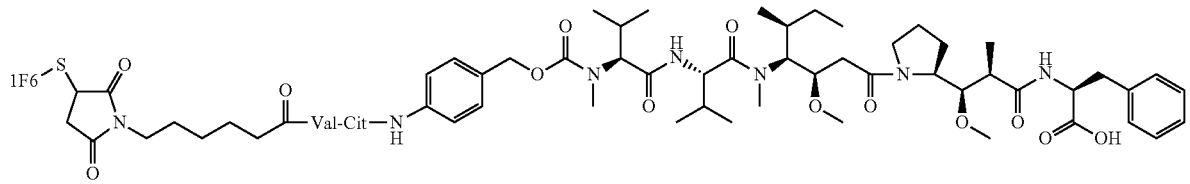

The synthesis of the ADC 1F6-vcMMAF, the general structure of which is depicted above, is described below.

1. MMAF Synthesis

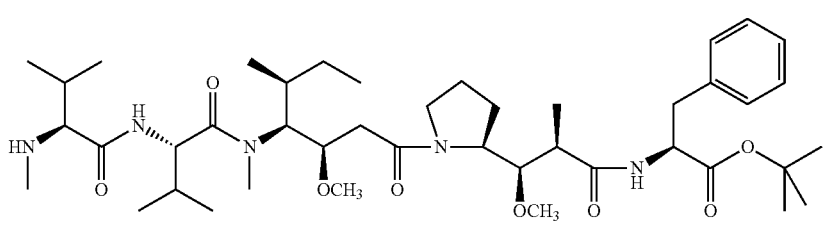

Compound 1

MMAF was prepared from its t-butyl ester (Compound 1) as is described below. Phenylalanine t-butyl ester HCl salt (868 mg, 3 mmol), N-Boc-Dolaproine (668 mg, 1 eq.), DEPC (820 µL, 1.5 eq.), and DIEA (1.2 mL) were diluted with dichloromethane (3 mL). After 2 hours (h) at room temperature (about 28 degrees Celsius), the reaction mixture was diluted with dichloromethane (20 mL), washed successively with saturated aqueous (aq.) NaHCO₃ (2×10 mL), saturated aq. NaCl (2×10 mL). The organic layer was separated and concentrated. The resulting residue was re-suspended in ethyl acetate and was purified via flash chromatography on silica gel in ethyl acetate. The relevant fractions were combined and concentrated to provide the dipeptide as a white solid: 684 mg (46%). ES-MS m/z 491.3 [M+H]$^+$.

For selective Boc cleavage in the presence of t-butyl ester, the above dipeptide (500 mg, 1.28 mmol) was diluted with dioxane (2 mL). 4M HCl/dioxane (960 µL, 3 eq.) was added, and the reaction mixture was stirred overnight at room temperature. Almost complete Boc deprotection was observed by RP-HPLC with minimal amount of t-butyl ester cleavage. The mixture was cooled down on an ice bath, and triethylamine (500 µL) was added. After 10 min., the mixture was removed from the cooling bath, diluted with dichloromethane (20 mL), washed successively with saturated aq. NaHCO₃ (2×10 mL), saturated aq. NaCl (2×10 mL) The organic layer was concentrated to give a yellow foam: 287 mg (57%). The intermediate was used without further purification.

The tripeptide N-Fmoc-N-Methylval-val-dil-O-t-butyl (0.73 mmol) was treated with TFA (3 mL), dichloromethane (3 mL) for 2 h at room temperature. The mixture was concentrated to dryness, the residue was co-evaporated with toluene (3×20 mL), and dried in vacuum overnight. The residue was diluted with dichloromethane (5 mL) and added to the deprotected dipeptide Dap-phe-O-t-butyl (287 mg, 0.73 mmol), followed by DIEA (550 µL, 4 eq.), DEPC (20 µL, 1.1 eq.). After 2 h at room temperature the reaction mixture was diluted with ethyl acetate (50 mL), washed successively with 10% aq. citric acid (2×20 mL), saturated aq. NaHCO₃ (2×10 mL), saturated aq. NaCl (10 mL). The organic layer was separated and concentrated. The resulting residue was re-suspended in ethyl acetate and was purified via flash chromatography in ethyl acetate. The relevant fractions were combined and concentrated to provide N-Fmoc-N-Methylval-val-dil-dap-phe-O-t-butyl as a white solid: 533 mg (71%). R$_f$ 0.4 (EtOAc). ES-MS m/z 1010.6 [M+H]$^+$.

The product (200 mg, 0.2 mmol) was diluted with dichloromethane (3 mL), diethylamine (1 mL). The reaction mixture was stirred overnight at room temperature. Solvents were removed to provide an oil that was purified by flash silica gel chromatography in a step gradient 0-10% MeOH in dichloromethane to provide Compound 1 (below) as a white solid: 137 mg (87%). R$_f$ 0.3 (10% MeOH/CH₂Cl₂). ES-MS m/z 788.6 [M+H]$^+$.

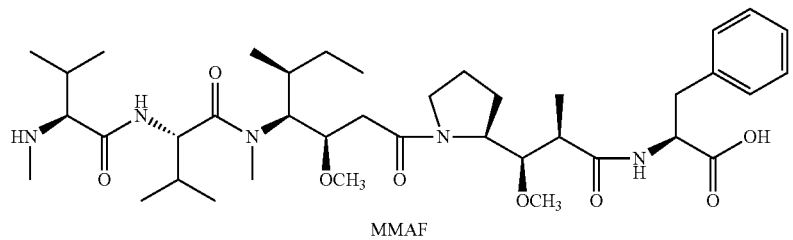

MMAF

MMAF was prepared from Compound 1 (30 mg, 0.038 mmol) by treatment with 4M HCl/dioxane (4 ml) for 7 h at room temperature. The solvent was removed, and the residue was dried in a vacuum overnight to give provide MMAF as a hydroscopic white solid: 35 mg (120% calculated for. HCl salt). ES-MS m/z 732.56 [M+H]$^+$.

2. Preparation of Drug-Linker Compound

Compound 1 (83 mg, 0.11 mmol), maleimidocaproyl-L-valine-L-citrulline-p-aminobenzyl alcohol p-nitrophenylcarbonate (85 mg, 0.12 mmol, 1.1 eq.), and HOBt (2.8 mg, 21 µmol, 0.2 eq.) were taken up in dry DMF (1.5 mL) and pyridine (0.3 mL) while under argon. After 30 h, the reaction was found to be essentially complete by HPLC. The mixture was evaporated, taken up in a minimal amount of DMSO and purified by prep-HPLC (C₁₂-RP column, 5µ, 100 Å, linear gradient of MeCN in water (containing 0.1% TFA) 10 to 100% in 40 min followed by 20 min at 100%, at a flow rate of 25 mL/min) to provide MC-Val-Cit-PAB-MMAF-O-t-butyl ester as a white solid. Yield: 103 mg (71%). ES-MS m/z 1387.06 [M+H]$^+$, 1409.04 [M+Na]$^+$; UV λ$_{max}$ 205, 248 nm.

MC-Val-Cit-PAB-MMAF-O-t-butyl ester (45 mg, 32 µmol) was suspended in methylene chloride (6 mL) followed by the addition of TFA (3 mL). The resulting solution stood for 2 h. The reaction mixture was concentrated in vacuo and purified by prep-HPLC (C₁₂-RP column, 5µ, 100 Å, linear gradient of MeCN in water (containing 0.1% TFA) 10 to 100% in 40 min followed by 20 min at 100%, at a flow rate of 25 mL/min). The desired actions were concentrated to provide MC-Val-Cit-PAB-MMAF as an off-white solid. Yield: 11 mg (25%). ES-MS m/z 1330.29 [M+H]$^+$, 1352.24 [M+Na]$^+$; UV $\lambda_{max}$ 205, 248 nm.

3. Conjugate Preparation

Antibody Reduction. To 0.75 mL 1F6 (4.2 mg/mL) was added 50 µL of 500 mM sodium borate/500 mM NaCl, pH 8.0, followed by 100 µL of 100 mM DTT in water, and 100 µL PBS. After incubation at 37° C. for 30 min, the buffer was exchanged by elution over G25 resin equilibrated and eluted with PBS containing 1 mM DTPA (Aldrich). The thiol/Ab value was found to be 8.9 by determining the reduced antibody concentration from the solution's 280 nm absorbance, and the thiol concentration by reaction with DTNB (Aldrich) and determination of the absorbance at 412 nm.

Conjugation of the Reduced Antibody. The reduced mAb was chilled on ice. The drug-linker compound was used as a DMSO solution of known concentration, and the quantity of drug-linker added to the reaction mixture was calculated as follows: L stock solution=V×[Ab]×Fold Excess/[Drug-Linker], where V and [Ab] are the volume and molar concentration of the reduced antibody solution, respectively. The reduced antibody (785 µl of 1.77 mg/ml) was added to the mixture of 7.2 µl of 12.9 mM MCvcMMAF in 92 µl of acetonitrile and mixed rapidly. The reaction mixture was allowed to incubate on ice for 1 h and followed by addition of a 40 µL of 100 mM cysteine. The reaction mixture was purified by G25 column equilibrated in PBS at 4° C. 1F6-vcAFP was then filtered through 0.2 micron filters under sterile conditions and immediately frozen at –80° C. 1F6-vcMMAF was analyzed for 1) concentration, by UV absorbance; 2) aggregation, by size exclusion chromatography; 3) drug/Ab, by measuring unreacted thiols by treatment with DTT, followed by DTNB, and 4) residual free drug, by reverse phase HPLC.

EXAMPLE 3

Expression of CD70 on Hematologic Cell Lines

Surface expression of CD70 was examined using flow cytometry. In general, 0.2×10$^6$ cells were incubated with 50 µl of staining medium (RPMI-1640 supplemented with 5-10% FBS) containing a fluorochrome-conjugated mAb (10 µg/ml) for single-color flow cytometry or a cocktail of fluorochrome-conjugated mAbs for multiple-color flow cytometry. Incubations were carried out on ice for 20-30 minutes. Cells were then washed 3 times with the staining buffer and fixed in PBS containing 1% of paraformaldehyde. Flow cytometric analysis was performed with a FACScan (BD Immunocytometry, San Jose, Calif.) and data were analyzed by either the CellQuest (BD Immunocytometry) or the WinMDI software. The anti-human CD70 monoclonal antibodies (mAb) 1F6 and 2F2 were obtained from the Central Laboratory of the Netherlands Red Cross Blood Transfusion Service (Amsterdam, The Netherlands). 1F6 was conjugated to AlexaFluor488 (AF) (Molecular Probes, Eugene, Oreg.) according to the manufacturer's instruction, and AF-conjugated 1F6 was used to detect CD70 by flow cytometry whenever necessary. The anti-CD70 mAb Ki-24 and anti-CD3 mAb were purchased from BD PharMingen (San Diego, Calif.).

The expression of cell surface CD70 was surveyed on a panel of hematologic cell lines. This panel included both Epstein-Barr Virus (EBV) negative American Burkitt's lymphoma (BL) and EBV$^+$ African Burkitt's lymphoma lines, a variety of non-Hodgkin's lymphoma (NHL) lines which are EBV$^-$, 2 Hodgkin's disease (HD) lines, 2 EBV-transformed B lymphoblastoid cell lines (EBV-LCL), and an acute T cell leukemia line Jurkat (FIG. 4). The cell lines were maintained in culture conditions specified by the ATCC or DSMZ. For flow cytometric analysis, AF-conjugated or a commercially available anti-CD70 (clone Ki-24) purchased from BD PharMingen was used. Cell lines on which anti-CD70 showed greater than 2-fold binding compared to the control IgG binding, based on mean fluorescence intensities, were arbitrarily defined as CD70-expressing. Based on this criterion, all of the BL lines, both EBV$^+$ and EBV$^-$, examined expressed detectable, albeit low levels of CD70. Five out of ten NHL cell lines expressed CD70. Both HD and EBV-LCL also expressed CD70 at levels that were generally higher than those of BL and NHL lines. The acute T leukemia cell line Jurkat was found to be CD70$^-$.

EXAMPLE 4

Proliferation Inhibitory and Cytotoxic Effects of Anti-CD70 ADCs on CD70$^+$ Hematologic Lines A subset of the CD70$^+$ hematologic lines listed in FIG. 4 was tested for sensitivity to the 1F6 ADCs. These lines were seeded at 5,000 cells per well in 96-well plates in quadruplicates in a total of 200 µl of culture medium containing graded doses of the ADCs as indicated in the FIG. 5 and the accompanying figure legend. Proliferation assays were carried out for 96 hours. Tritiated thymidine ($^3$H-TdR) incorporation during the last 16 hours of incubation was used to assess DNA synthesis. The responses of a CD70$^+$ B lymphoma cell line WSU-NHL and the CD70$^-$ Jurkat cells are shown in the upper panels of FIG. 5. Both 1F6-vcMMAE and 1F6-vcAFP exerted dose-dependent inhibitory effects on the proliferation of WSU-NHL cells. Proliferation inhibitory effects were apparent when the ADCs were used at concentrations higher than 0.005 µg/ml. The non-binding IgG control ADCs did not exert any significant effects at concentrations lower than 0.5 µg/ml. On the other hand, proliferation of the CD70$^-$ Jurkat acute T leukemia cell line was not affected by either 1F6-vcMMAE or 1F6-vcAFP at concentrations as high as 2 µg/ml. Hence, the proliferation inhibitory activity of the 1F6 ADCs on target positive cells resulted from specific binding of ADCs to CD70 expressed on the target cells. The responses of other CD70$^+$ cell lines tested are summarized in the lower panel of FIG. 5. Significant proliferation inhibition by the 1F6 ADCs was observed in 2 of the 3 B lineage non-Hodgkin's lymphoma cell lines (MC116 and WSU-NHL), 2 of 2 Hodgkin's disease lines, and the EBV-transformed B lymphoblastoid cell line CESS. In all the responsive cell lines tested, 1F6-vcAFP was demonstrated to exert more potent inhibitory activity than 1F6-vcMMAE. These results suggest that anti-CD70 ADCs can potentially be applied in immunotherapy of CD70$^+$ lymphomas. Moreover, EBV-LCLs are phenotypically very similar to activated normal B cells. Both EBV-LCLs and activated normal B cells are also efficient antigen presenting cells possessing strong T cell stimulatory activities. The observation that anti-CD70 ADC can efficiently suppress the proliferation of EBV-LCL CESS cells indicates that anti-CD70 ADCs can also be applied to suppress immune responses by eliminating activated B cells.

EXAMPLE 5

Expression of CD70 Transcripts in Solid Tumors

Hodgkin's disease (BD) and nasopharyngeal carcinoma (NPC) are two examples of conditions that frequently associate with EBV and a prominent lymphoid stroma at the tumor sites. The role of this lymphoid stroma is uncertain and may represent infiltration of lymphocytes to tumors as part of the immune response to tumor-associated antigens. Alternatively, the recruitment of lymphocytes by tumor cells may be a mechanism through which tumor cells derive cytokine and growth factors from the infiltrating lymphocytes in a paracrine fashion. Some of these growth factors may contribute to tumor development by supporting tumor cell proliferation as hypothesized for HD (Gruss et al., 1997, *Immunol. Today* 18:156-63). CD70 has been found to be present on the Reed-Sternberg cells in HD, and FIG. 4 demonstrates the expression of CD70 on HD cell lines. In a study on frozen tumor biopsies from EBV-associated undifferentiated nasopharyngeal carcinomas, 80% (16 of 20 cases) showed in situ expression of the CD70 protein on tumor cells (Agathanggelou et al., 1995, *Am. J. Pathol.* 147:1152-60). Others also reported the expression of CD70 on EBV-tumors including thymic carcinomas (Hishima et al., 2000, *Am. J. Surg. Path.* 24:742-746), gliomas, and meningiomas (Held-Feindt and Mentlein, 2002, *Int. J. Cancer* 98:352-56).

The potential expression of CD70 in additional carcinoma types was further surveyed using the Cancer Profiling Array (CPA) (BD Biosciences Clontech, Palo Alto, CA). The CPA includes normalized cDNA from 241 tumor and corresponding normal tissues from individual patients. In order to examine the expression of CD70 message in these patients, a piece of cDNA corresponding to 3' untranslated region of nucleotides 734-874 of the CD70 message was amplified using the reverse transcriptase polymerase chain reaction (RT-PCR) approach. First strand cDNA was synthesized from total RNA isolated from the Burkitt's lymphoma cell line Ramos (ATCC) using the SuperScriptTM First Strand Synthesis System for RT-PCR from Invitrogen (Carlsbad, CA). The forward primer 5'-CCA CTG CTG CTG ATT AG-3' (SEQ ID NO:54), the reverse primer 5'-CAA TGC CTT CTC TTG TCC-3' (SEQ ID NO:55), and the Advantage 2 PCR Kit (Clontech, Palo Alto, CA) were used for the PCR. The PCR product was cloned into the pCR4-TOPO vector and sequence verified. To generate a probe for hybridization, PCR was run using the cloned cDNA as the template, the above primer pairs, and the Advantage 2 PCR Kit (Clontech). To label the probe with 32P-dGTP, 200 ng of the purified PCR product were combined with 75 ng of random hexamer, 33 iuM each of dATP, dTTP and dCTP, 5 IA of a-32P dGTP (approximately 3000 Ci/mmol, 10 mCi/ml, Amersham Pharmacia Biotech, Piscataway, NJ), 1 IA of Klenow fragment (New England Biolabs, Beverly, MA), and lx EcoPol buffer (New England Biolabs) in a total volume of 50 pl. The reaction mixture was incubated at room temperature for 15 minutes, and EDTA was added to a final concentration of 10 mM to stop the reaction. Labeled probe was purified using ProbeQuant G-50 Micro Columns (Amersham Pharmacia Biotech, Piscataway, NJ). This probe was hybridized to patient cDNA spotted on a CPA using the BD ExpressHyb hybridization solution (BD Biosciences) according to the manufacturer's instructions. Hybridization signals were quantified by phospho-imaging on a Phospholmager SI (Amersham). Reprobing the same CPA for the housekeeping EF-1gene gave tumor:normal ratio of approximately one for each sample pair, confirming comparable loading of cDNA. Therefore ratios between the CD70 hybridization signals obtained from tumor and normal cDNAs were used as a semi-quantitative measurement to CD70 transcript expression.

Differential hybridization of the CD70 probe to tumor cDNA was observed in several cancer types. Most notably, cDNAs from 9 of 20 cases of kidney carcinoma and one case each of colon, stomach, and rectum carcinoma showed more intense hybridization signals than cDNAs from the corresponding normal tissues. The 9 cases (45%) of kidney cancer in FIG. 6, all classified as RCC, showed more than 2-fold (range of 2.3 to 8.9) over-expression of CD70 transcripts. In the single case of stomach, colon, and rectum cancer showing differential CD70 cDNA hybridization (FIG. 6), the tumor: normal ratios were 2.9, 8.9, and 3.2, respectively.

Figure 6:
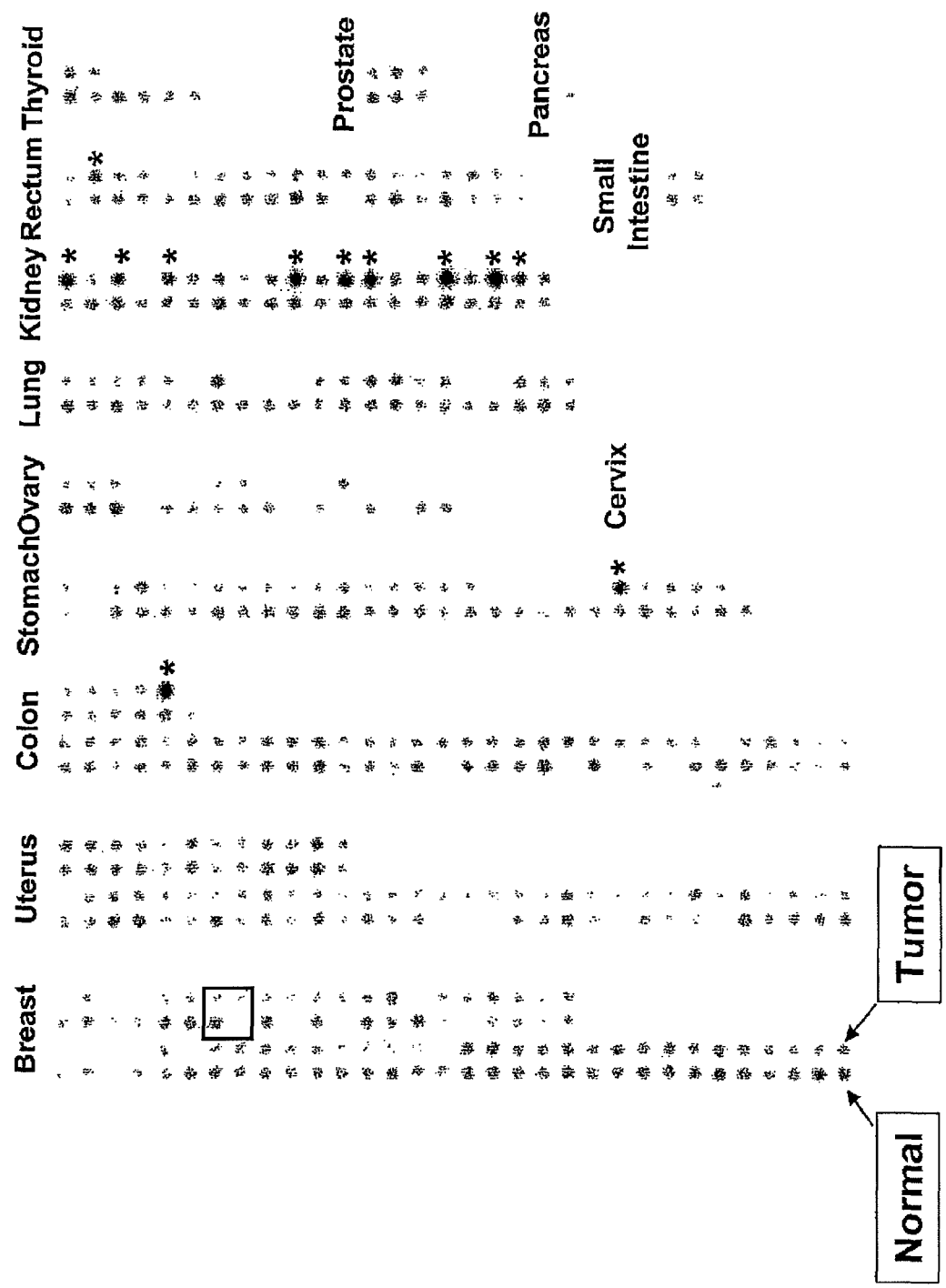
FIG. 6: Cancer Profiling Array (CPA) analysis of the expression of CD70 message in multiple cancer types. Expression of CD70 in 241 tumor isolates and the corresponding adjacent normal tissues on a CPA was determined by hybridization with a CD70 cDNA probe. Thirteen tumor types are present on the array as indicated in the figure. Each pair of dots represents a tumor sample (right side, T) and the corresponding normal tissue (left side, N). For some cDNA sets, as exemplified by the boxed sample set, the cDNA sample on the upper left spot is derived from the normal tissue, the upper right from the metastatic tumor, and the lower right from the primary tumor. Asterisks denote cDNA pairs in which CD70 transcript over-expression was detected in the tumor cDNA (tumor:normal ratio of >2-fold, based on hybridization intensity).

Quantitative PCR (QPCR) was used to quantify CD70 transcript expression in 8 RCC and 4 normal kidney cDNA samples, all obtained from BioChain (Hayward, Calif.). The RCC cDNA samples were from donors independent of those on the CPA in FIG. 6. QPCR analysis was performed using TaqMan™ MGB chemistry (Applied Biosystems, Foster City, Calif.) containing a reporter dye at the 5' end (FAM or VIC) and a non-fluorescent quencher (NFQ) at the 3' end on an ABI PRISM 7000 Sequence Detection System (Applied Biosystems). Assays specific for either CD70 (Applied Biosystems Assay#Hs00174297_m1) or control gene GAPDH (Applied Biosystems PDAR#4326317E) were used to evaluate samples. Comparison of CD70 transcript expression between normal kidney and RCC tissues was conducted based on the comparative threshold cycle (Ct) method as previously reported (Winer et al., 1999, *Anal. Biochem.* 270: 41-49; Aarskog and Vedeler, 2000, *Hum. Genet.* 107: 494-498). Ct values for the CD70 and a housekeeping gene GAPDH from two independent reactions were generated. The Ct values for the GAPDH transcripts from normal kidney and RCC samples did not differ significantly from each other (<1 cycle, student's t-test: p=0.405), suggesting that CD70 expression can be normalized against GAPDH for tumor: normal comparison. ΔCt values for CD70 expression in RCC and normal kidney samples were calculated by subtracting $Ct_{GAPDH}$ from $Ct_{CD70}$ to give $\Delta Ct_{Tumor}$ and $\Delta Ct_{Normal}$, respectively. ΔΔCt values were calculated by subtracting $\Delta Ct_{Normal}$ from $\Delta Ct_{Tumor}$. CD70 transcript expression in RCC expressed as fold increase over normal kidneys was then expressed as $2^{(-\Delta\Delta Ct)}$. CD70 transcript over-expression (>2-fold) was observed in 6 of the 8 RCC cDNA samples, consistent with the results obtained form the CPA experiment (FIG. 6). Over-expression of CD70 transcripts ranged from 2.5- to 133.7-fold (FIG. 7).

EXAMPLE 6

Expression of CD70 Protein on Renal Cell Carcinoma

Immunohistochemistry was used to determine if over-expression of CD70 transcript in RCC was paralleled by CD70 protein expression. Frozen RCC tissue sections and normal adjacent tissue sections from two patients independent of those used in CD70 transcript analysis (FIGS. 6 and 7) were fixed in acetone at −20° C. for 10 minutes. After rehydration in PBS, sections were blocked with PBS containing 5% normal goat serum and Avidin D for 30 minutes at room temperature, and washed in PBS. Sections were incubated with the anti-CD70 mAb 2F2 or non-binding IgG at 2 µg/ml in PBS containing 5% normal goat serum with biotin for 60 minutes at room temperature. After washes with PBS, biotinylated anti-mouse IgG (VECTASTAIN ABC Kit, Vector Laboratories, Burlingame, Calif.) at a 1:250 dilution in PBS containing 5% normal goat serum was used to detect bound primary antibody by incubating for 30 minutes at room temperature. Excess biotinylated anti-mouse IgG was removed by PBS washes. Sections were quenched with 1% $H_2O$, in PBS for 30 minutes at room temperature, washed, and then incubated with the VECTASTAIN ABC complex made up according to the manufacturer's instructions. After PBS washes, sections were incubated for 30 minutes at room temperature with the DAB solution (VECTASTAIN ABC Kit) made up according to the manufacturer's instructions for color development. Sections were then washed in water, counterstained with hematoxylin for 2 minutes, mounted in VectaMount (Vector Laboratories), and then observed using 40× light microscopy.

Intense binding of 2F2 to RCC tumor sections from 2 different donors was observed (FIG. 8A, right panels). In contrast, a control IgG did not bind to serial tumor sections, confirming the specificity of 2F2 for CD70 (FIG. 8A, left panels). 2F2 also did not demonstrate binding beyond that of the control IgG to normal adjacent tissues from the same RCC samples (FIG. 8B), suggesting minimal or no CD70 protein expression in normal kidneys. These results confirm the overexpression of CD70 transcripts in RCC and provide direct evidence for in situ CD70 protein expression in RCC.

Figure 9A:
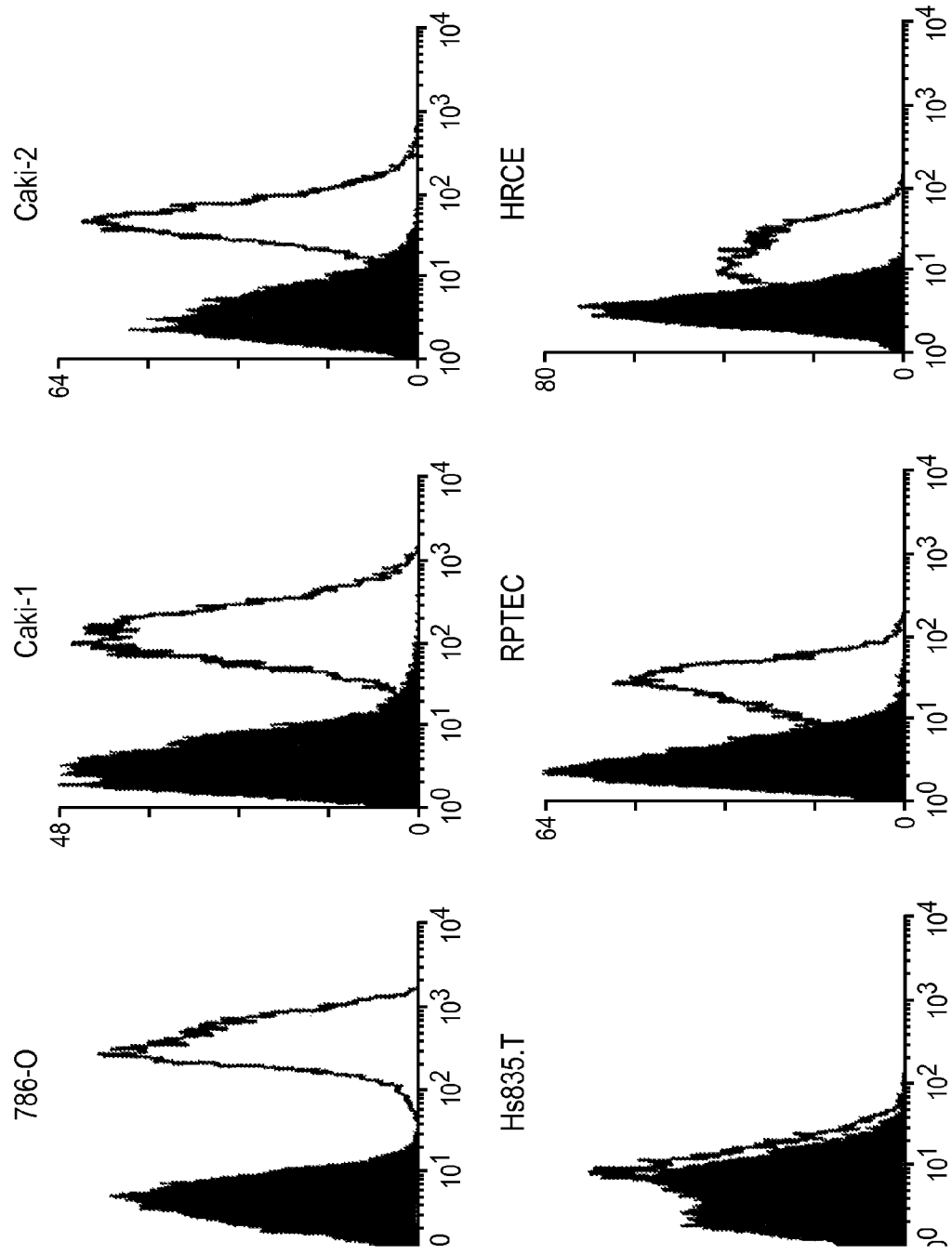
FIGS. 9A and B: Expression of CD70 on renal cell carcinoma cell lines (RCC). CD70 expression on the surface of a panel of RCC was determined by flow cytometry. (A) The staining profiles of an anti-CD70 (open curves) and a control IgG (closed curves) on four representative RCC cell lines 786-O, Caki-1, Caki-2, and Hs 835.T and two normal renal tubule epithelial lines RPTEC and HRCE are shown. (B) CD70 expression on additional RCC cell lines (CAL54, SK-RC-6, SK-RC-7, 786-O, A498, and ACHN) is compared to cell lines shown in (A). Mean fluorescence intensity of anti-CD70 staining and background fluorescence are plotted. Numbers on top of each bar indicate either mean fluorescence intensity obtained from anti-CD70 binding or background fluorescence.

Expression of the CD70 protein on the RCC cell surface was next examined. A panel of 7 RCC lines was evaluated using flow cytometry. The RCC lines Hs 835.T, Caki-1, Caki-2, 786-O, 769-P, and ACHN were obtained from the ATCC (Manassas, Va.) and were maintained in conditions specified by the ATCC. The RCC lines CAL54 and A498 were obtained from Deutsche Sammlung von Mikroorganismen and Zellkulturen GmbH (Braunschweig, Germany). Cell lines were maintained in the conditions specified the vendors. The RCC lines SK-RC-6 and SK-RC-7 have been reported previously (Murakami et al., 1984, *Hepatology* 42:192-8). SK-RC-6 and SK-RC-7 was maintained in DMEM supplemented with 10% fetal bovine serum (FBS). Two normal human renal tubule epithelial lines, RPTEC and HRCE (Cambrex, East Rutherford, N.J.) were also included in the analysis. FIG. 9A shows that the RCC lines 786-O, Caki-1, and Caki-2 expressed CD70 while Hs 835.T did not. Low, but detectable, levels of CD70 expression were also observed on the normal kidney tubule epithelial lines PRTEC and HRCE. FIG. 9B summarizes the relative levels of CD70 expressed on RCC lines and normal kidney epithelial cells lines based on the mean fluorescence intensity obtain from flow cytometry. Of the 10 RCC lines tested 9 were found to be CD70 expressing. These results demonstrate that the presence of CD70 transcripts and protein in kidney carcinomas was accompanied by surface expression of CD70 on the cancer cells.

EXAMPLE 7

Figure 10:
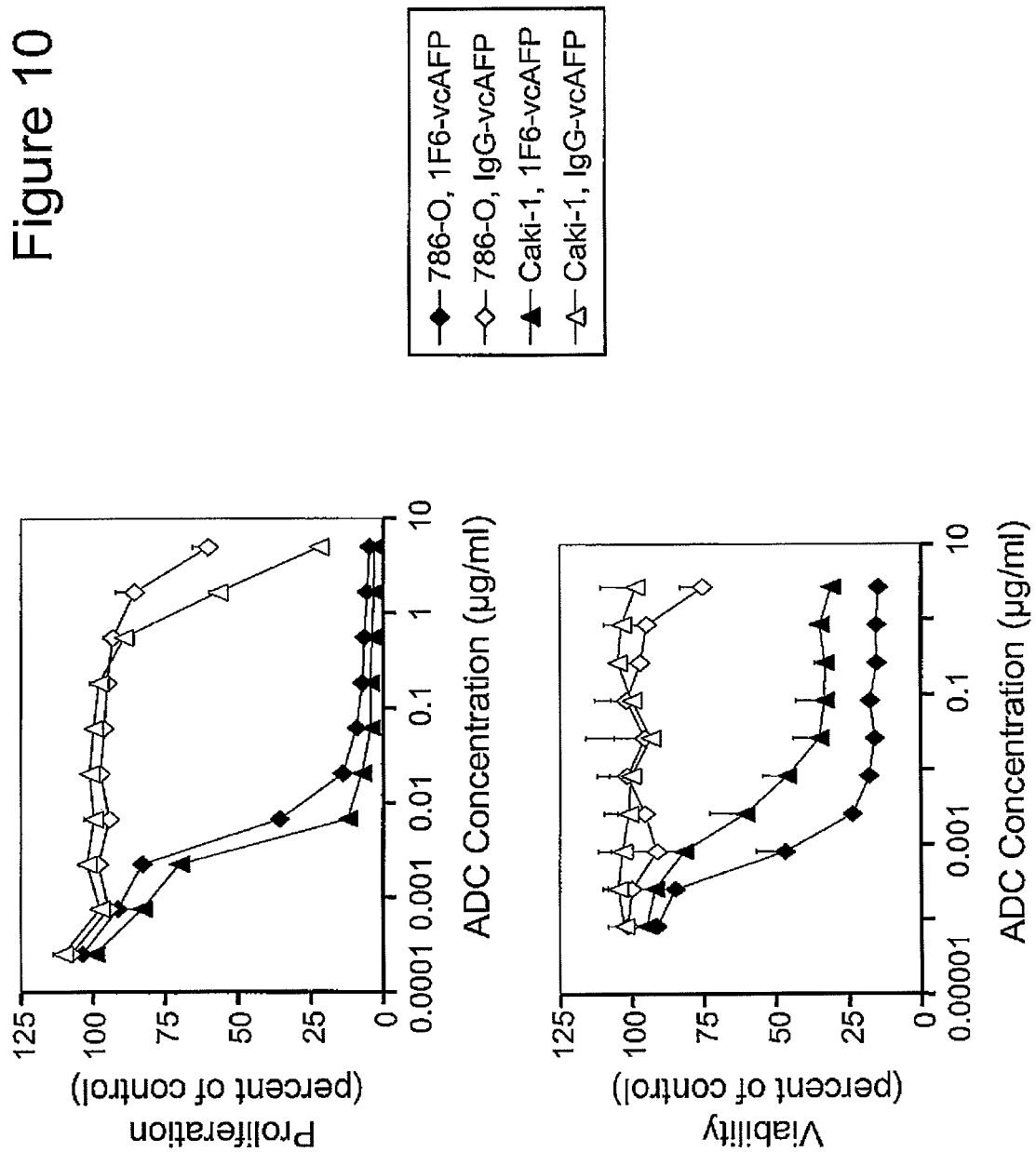
FIG. 10: Growth inhibitory and cytotoxicity activities of 1F6-vcAFP. 786-O or Caki-1 cells were incubated with graded doses of 1F6-vcAFP or the non-binding control IgG-vcAFP. Cells were incubated for a total of 96 hours. $^3$H-thymidine incorporation (upper panel) and reduction of alamarBlue (lower panel) were used to determine proliferation and cell viability, respectively. Data points are expressed as percentages of the untreated control. Error bars represent the standard deviations of values obtained from quadruplicate wells.

Proliferation Inhibitory and Cytotoxic Effects of Anti-CD70 ADCs on CD70⁺ Renal Cell Carcinoma Cell Lines To examine the responses of CD70⁺ RCC lines to 1F6 ADCs, cells were seeded between 1,000 to 3,000 cells per well in 100 µl of medium. An additional 100 µl of culture medium containing graded doses of ADCs were added to the wells after cells were allowed to attached overnight. In addition to DNA synthesis, cell viability, as a reflection of the cytotoxic activities of ADCs, was also assayed by the reduction of alamarBlue™ (Biosource International, Camarillo, Calif.). The alamarBlue™ dye was added at a one to four dilution during the last 4 to 24 hours of the incubation. Dye reduction was assessed by fluorescence spectrometry using the excitation and emission wavelengths of 535 nm and 590 nm, respectively. For analysis, the amount of $^3$H-TdR incorporated or the extent of alamarBlue™ reduction by the treated cells was compared to that of the untreated control cells. FIG. 10 shows the effects of 1F6-vcAFP on the proliferation ($^3$H-TdR incorporation) and viability (alamarBlue™ reduction) on two representative CD70⁺ RCC lines. 1F6-vcAFP demonstrated potent proliferation inhibitory (FIG. 10, upper panel) and cytotoxic (FIG. 10, lower panel) activities on Caki-1 and 786-O cells, maximal effects were achieved at concentrations lower than 0.1 µg/ml. In contrast, non-binding control IgG-vcAFP at concentrations lower than 1 µg/ml exerted minimal effects on these cells.

FIG. 11 summarizes the $IC_{50}$s for 1F6-vcMMAE, 1F6-vcAFP, and 1F6-vcMMAF on inhibiting the proliferation and inducing cytotoxicity in RCC and normal kidney tubule epithelial cells. 1F6-vcMMAE was very effective in suppressing the proliferation of Caki-1 and Caki-2 cells with $IC_{50}$ values lower than 20 ng/ml. However, it was not active on other CD70⁺ RCC lines, the CD70⁻ Hs 835.T cells, or the normal kidney epithelial lines RPTEC and HRCE. $IC_{50}$ values for proliferation inhibition by 1F6-vcAFP ranged from 2-247 ng/ml for CD70⁺ RCC lines. Substantially higher $IC_{50}$ values were obtained for 1F6-vcAFP on the CD70⁻ Hs 835.T, suggesting specific targeting of CD70. 1F6-vcMMAF were also active in inhibiting proliferation in all CD70⁺ RCC lines tested, with $IC_{50}$ values lower than 30 ng/ml. Proliferation inhibition was paralleled with cytotoxicity. $IC_{50}$ values for 1F6-vcAFP to induce cytotoxicity were below 20 ng/ml in 4 of the 7 CD70⁺ RCC lines tested, while those for 1F6-vcMMAF were below 30 ng/ml in 5 of 7 CD70⁺ RCC lines tested. Specific targeting by the 1F6 ADC to CD70 was confirmed by the much higher $IC_{50}$ values obtained for the control non-binding IgG ADCs, >1000 ng/ml for all the lines tested. Moreover, RCC appeared to be differentially more sensitive to anti-CD70 ADC-mediated proliferation inhibition and cytotoxicity, as despite detectable expression of CD70, normal kidney epithelial cells were very insensitive to 1F6 ADCs when compared to the CD70⁺ RCC lines.

EXAMPLE 8

In Vivo Efficacy of 1F6-vcAFP in a Xenograft Model of RCC

Figure 12:
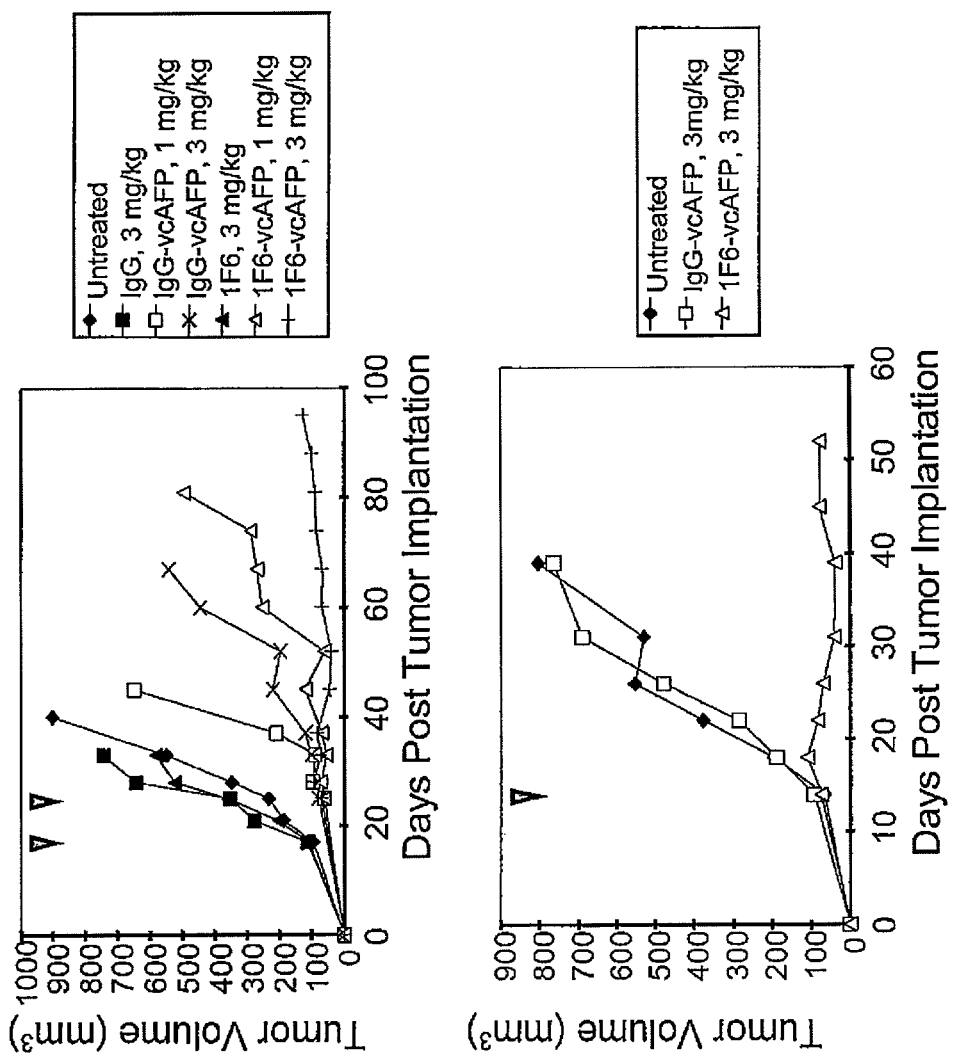
FIG. 12: In vivo efficacy of 1F6-vcAFP in a RCC model. Tumors were initiated in nude mice by implanting tissue tumor blocks (30 mm$^3$ in size) containing Caki-1 cells. Treatment began when average tumor size within a treatment group was around 100 mm$^3$. In the upper panel, treatment for the IgG and 1F6 groups began 17 days post implantation (filled arrow), while treatment for the 1F6-vcAFP and IgG-vcAFP groups began 25 days post implantation (open arrow). Indicated doses of either unconjugated mAbs or their ADCs were given for one course on a q4d×4 schedule. The lower panel shows results from a repeat experiment when treatment began 14 days (filled arrow) after tumor implantation with 3 mg/kg and a q4d×4 schedule of 1F6-vcAFP or IgG-vcAFP.

Subcutaneous xenografts of Caki-1 cells have been successfully used as models for RCC to test the efficacy of antibody-based therapeutics including an anti-VEGF antibody (Dagnaes-Hansen et al., 2003, *Anticancer Res.* 23: 1625-30) as well as an ADC consisting of calicheamicin the tall conjugated to an anti-gamma-glutamyltransferase antibody (Knoll et al., 2000, *Cancer Res.* 60: 6089-94). Using xenografts of the Caki-1 line in nude mice, the in vitro antitumor activity of 1F6-vcAFP was tested. To establish Caki-1 tumors, nude mice were injected subcutaneously with 5×10⁶ Caki-1 cells in 0.2 ml PBS. Average tumor size increased to more than 500 mm³ within 55 days post injection. Caki-1-containing tumors were excised from tumor bearing mice and tumor tissue blocks of approximately 30 mm³ were prepared. Naive nude mice to be used for evaluating in vivo antitumor activity of anti-CD70 ADC were each implanted subcutaneously with one tumor block of 30 mm³. Following implantation, tumor sizes increased to more than 800 mm³ within 40 days in the absence of any treatment (FIG. 12). Treatment was initiated when the average tumor size within a group was approximately 100 mm³ (FIG. 12, arrows). Very little therapeutic activity was detected in 1F6, as tumor growth rate in mice treated with 1F6 was virtually identical to either the untreated control or the IgG-treated group. However, treatment of mice with 1F6-vcAFP significantly inhibited tumor growth. The average tumor size in mice treated with 1 mg/ml of 1F6-vcAFP was <600 mm³ 56 days after treatment initiation, whereas in the group treated with IgG-vcAFP at the same dose the average tumor size was already >600 mm³ 20 days after treatment initiation (FIG. 12, upper panel). Increasing the dose of 1F6-vcAFP to 3 mg/ml further suppressed tumor growth; average tumor size was kept under 200 mm³ 70 days after treatment initiation while IgG-vc-AFP at the same dose resulted in tumors >400 mm³ 42 days after treatment initiation (FIG. 12, upper panel). The potent, specific in vivo antitumor activity of 1F6-vcAFP at 3 mg/kg was from a separate experiment is shown in FIG. 12, lower panel.

EXAMPLE 9

Expression of CD70 on Activated T Cells

Figure 13:
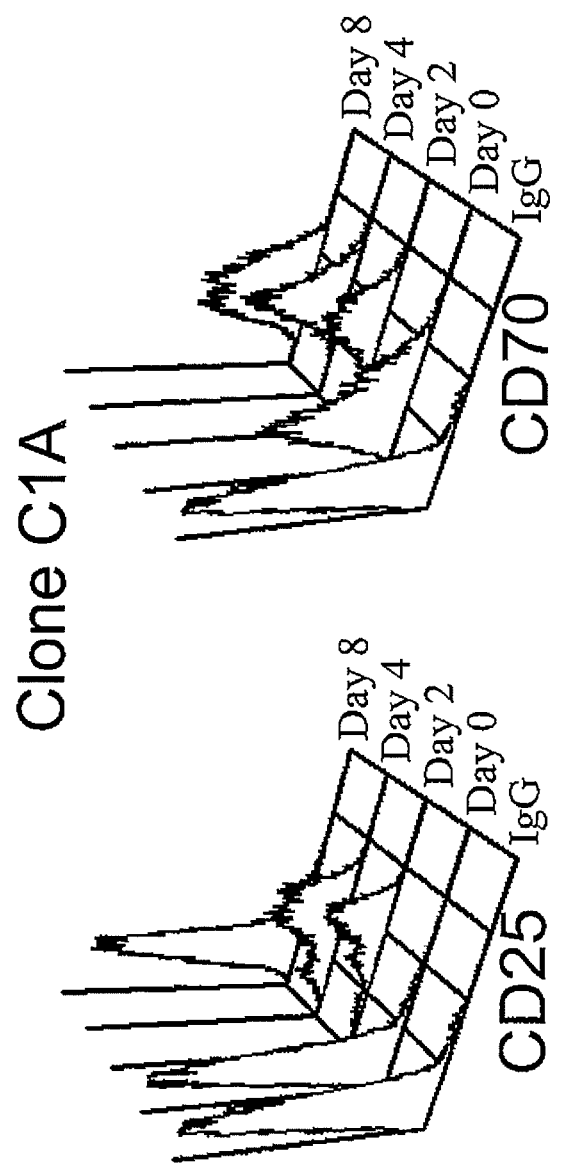
FIG. 13: Activation-induced CD70 expression on a T cell clone. A representative T cell clone C1A was activated by phytohemaggutinin A-L (PHA-L), irradiated feeder cells, IL-2, and. IL-4 . CD25 (left panel) and CD70 (right panel) expression on days 0, 2, 4, and 8 were determined by flow cytometric analysis.

The generation and maintenance of the T cell clones have been described in U.S. Provisional Patent Application No. 60/331,750 and in International Patent Application PCT/US02/37223, both of which are incorporated herein by reference in their entireties. To activate resting T cell clones, 5×10⁶ T cells were incubated in RPMI-1640 supplemented with 10% FBS and 2 mM L-glutamine with PHA-L (1-2 µg/ml) (Sigma), 10×10⁶ irradiated feeder cells (CESS), rhIL-2 (200 IU/ml) (Proleukin, Chiron, Emeryville, Calif.), and IL-4 (10 ng/ml) (R&D Systems, Minneapolis, Minn.). T cell clones were usually allowed to expand for 10-14 days before re-stimulation. A panel of antigen non-specific T cell clones was examined for the expression of CD70. Table 2 summarizes the characteristics of the T cell clones examined. This panel contains both CD4⁺ and CD8⁺ T cells clones that appear to belong to different T cell differentiation pathways as suggested by their cytokine profiles. Significant levels of CD70 were detectable on all of the clones examined. T cell clones were activated by PHA, irradiated feeder cells (CESS), and rIL-2 and the expression of CD25 and CD70 was monitored by flow cytometric analysis. Clone C1A, representative of other T cell clones, showed extensive upregulation of CD25, which peaked on day 2 (FIG. 13). This is indicative of T lymphocyte activation. Expression of CD25 gradually declined in the following days. The induction of CD70 expression paralleled that of CD25. The peak CD70 induction was also observed after 2 days of stimulation. Considerable CD70 expression was still detectable on day 8. All T cell clones examined, including those listed in Table 2, showed similar kinetics and magnitudes of activation-induced expression of CD70.

TABLE 2

T cell clone phenotypes and activation-induced expression of CD70

| T cell clone | T-lineage marker | CD70 expression* | Cytokine profile | Designation |
|---|---|---|---|---|
| 3.27.2 | CD3, CD4 | 15 | IL-4, IL5, IL-13, IFNγ | Th0 |
| 4.01.1 | CD3, CD4 | 7 | IL-4, IL5, IL-13, IFNγ | Th0 |
| 20G5 | CD3, CD4 | 3 | IL-4, IL-13 | Th2 |
| 40D8 | CD3, CD4 | 8 | IL-4, IL-13 | Th2 |
| C1A | CD3, CD8 | 3 | IL-4, IL-13, IFNγ | Tc0 |
| C2A | CD3, CD8 | 12 | IL-4, IL-13, IFNγ | Tc0 |

*Ratio between the mean log fluorescence intensities for anti-CD70 binding and control IgG binding

EXAMPLE 10

Proliferation Inhibitory Effects of Anti-CD70 ADCs on Activated T Cells

The effects of 1F6 ADCs on the proliferation of activated T cells were examined using activated T cell clones, mixed lymphocyte reactions (MLR), and antigen-primed T cells. Standard proliferation assays in 96-well format in quadruplicates were used to evaluate the effects of anti-CD70 ADCs on activated T cells. For MLR, PBMCs were seeded at 50,000 cells/well with 50,000 irradiated allogeneic CESS cells in a total volume of 200 µl of medium. For tetanus toxoid-induced T cell proliferation, tetanus toxoid-reactive T cells were seeded at 20,000 cells/well with 2,000 autologous DCs in a total volume of 200 µl. Dialyzed and clarified tetanus toxoid (Colorado Serum Company, Denver, Colo.) was used at a final concentration of 1:50 dilution. Two-day activated T cell clones were seeded at 10,000 cells per well. Proliferation assays was usually carried out for 72 to 120 hours. Tritiated thymidine (³H-TdR) incorporation during the last 16 hours of incubation and scintillation counting were used to assess DNA synthesis. For analysis, the amount of thymidine incorporated by the treated cells was compared to that of the untreated control cells.

Figure 14:
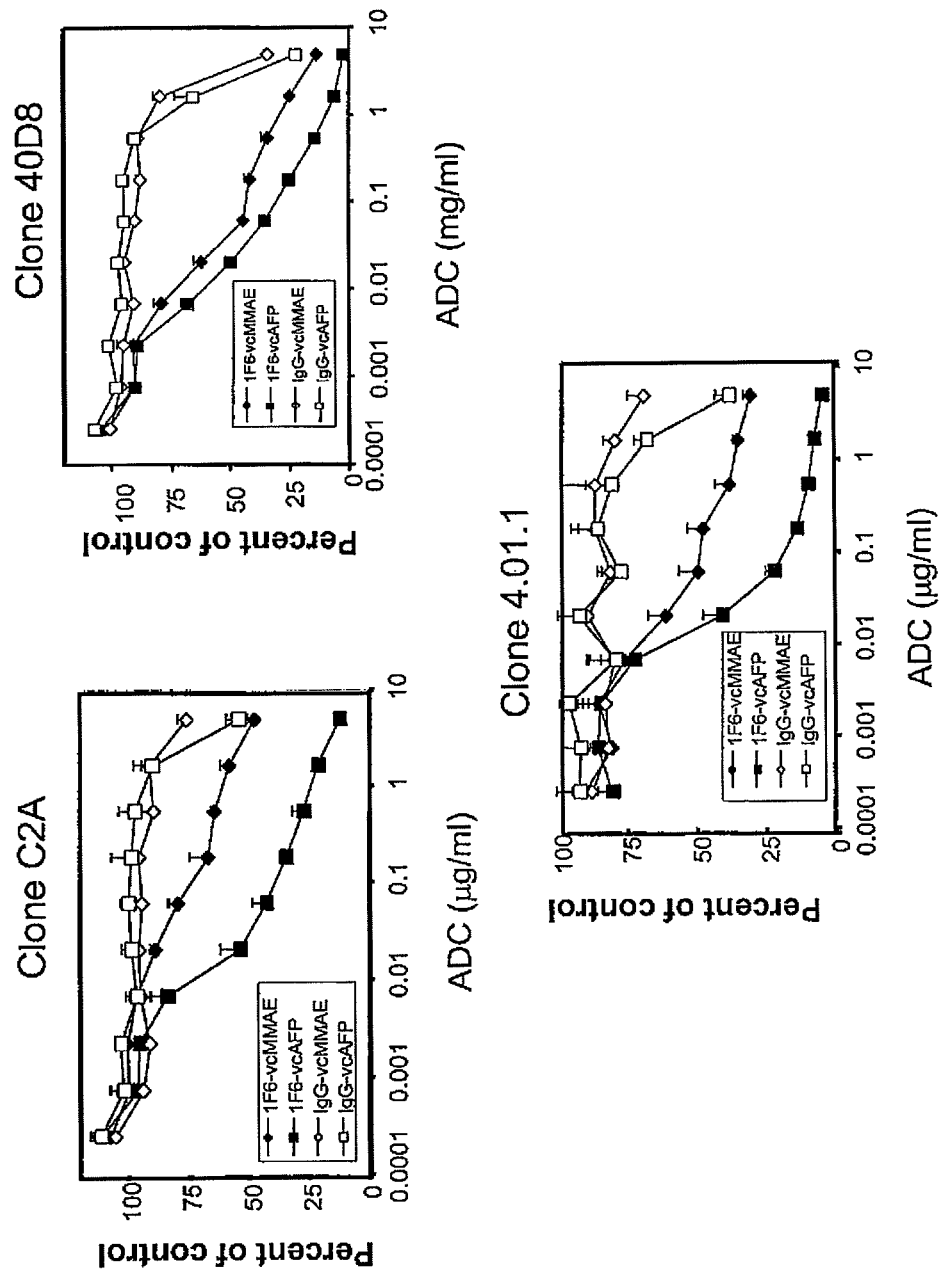
FIG. 14: Effects of anti-CD70 ADCs on the proliferation of activated T cell clones. Resting T cell clones C2A, 40D8, and 4.01.1 were induced to express CD70 as described. At the peak of CD70 expression (2 days after activation), cells were harvested and treated with graded doses of 1F6-vcMMAE, 1F6-vcAFP, or the corresponding non-binding control IgG (IgG) ADCs as indicated in the figure in the presence of rhIL-2 and rhIL-4 . Cells were exposed to the ADCs continuously for an additional 72 hours. T cell proliferation was determined by pulsing with $^3$H-TdR during the last 16 hours of incubation.

In the first system, the responses of T cell clones to 1F6 ADCs were examined. Resting T cell clones were activated to induce CD70 expression as described in FIG. 13 and the accompanying figure legend. After 2 days of activation, a portion of the cells was analyzed for CD25 and CD70 expression by flow cytometry to confirm cellular activation and CD70 induction. The remaining cells were pelleted and resuspended in new medium containing 200 IU/ml of rIL-2 or 200 IU/ml of IL-2 and 10 ng/ml IL-4. Cells were then plated out at 10,000 cells/well in a final volume of 200 µl of medium containing graded concentrations of 1F6 ADCs or the non-binding IgG ADCs. Cells were incubated for an additional 72 hours with the last 16 hours pulsed with ³H-TdR to assess cellular DNA synthesis. The results for the responses of three T cell clones toward ADC treatment was shown in FIG. 14. 1F6 ADCs at concentrations higher than 0.01 µg/ml significantly inhibited the proliferation of the T cell clones. 1F6-vcAFP appeared to be more active than 1F6-vcMMAE; the IC$_{50}$s for 1F6-vcAFP on all 3 clones were found to be below 0.05 µg/ml. The control ADC cIgG-vcMMAE and cIgG-vcAFP did not significantly inhibit proliferation at concentrations below 2 µg/ml, confirming the antigen specificity of the 1F6 ADCs.

Figure 15:
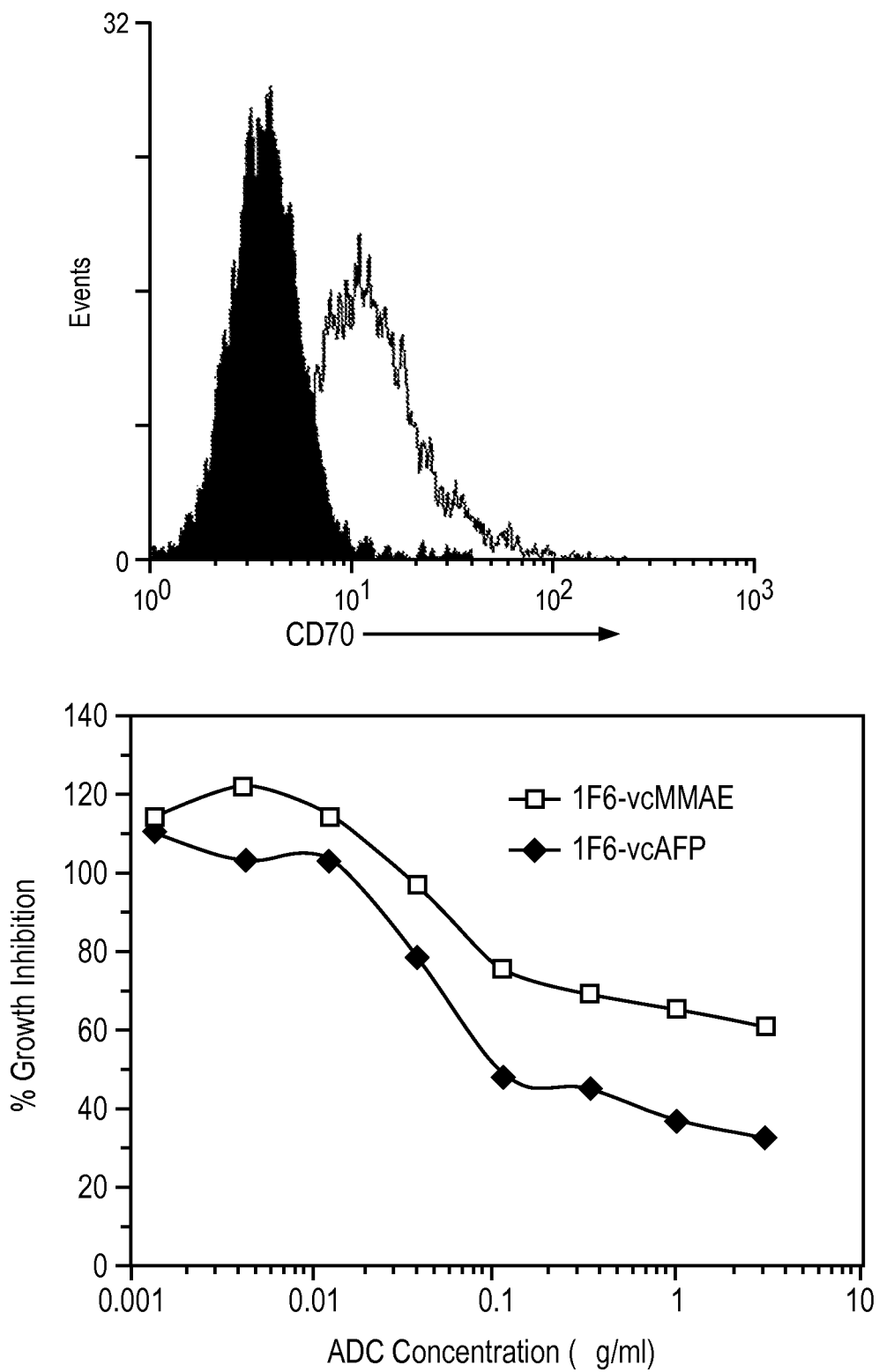
FIG. 15: Effects of anti-CD70 ADCs on mixed lymphocyte reaction. An MLR was set up between PBMCs and irradiated allogeneic CESS cells. Expression of CD70 on activated alloreactive T cells is shown on the upper panel. Binding of anti-CD70 mAb and control IgG is indicated by the open and closed curves, respectively. Graded doses of either 1F6-vcMMAE or 1F6-vcAFP were added to the culture at initiation. Cultures were exposed to the ADCs for a total of 120 hours. T cell proliferation was determined by pulsing with $^3$H-thymidine during the last 16 hours of incubation (lower panel).

In the second system, an MLR was set up between PBMC and an irradiated allogeneic stimulator CESS. Allogeneic activation of peripheral blood T cells was achieved by conventional mixed lymphoycte reactions (MLR). MLR were initiated by mixing PBMCs and irradiated allogeneic Epstein-Barr virus (EBV)-transformed B lymphoblastoid CESS cells (ATCC, Manassas, Va.) at a ratio of one T cell to ten irradiated CESS cells. T cell density was adjusted to 0.25×10⁶ T cells/ml of RPMI-1640 supplemented with 10% FBS and 2 mM L-glutamine. Rapid proliferation and expansion of alloreactive T cells was observed after approximately 96 hours of culture. After 5 days of stimulation, cells were assessed for CD70 expression using the anti-CD70 mAb 1F6 by flow cytometry. Flow cytometric analysis showed that most of the cells within the viable gate were CD3⁺ T cells and that CD70 was expressed on the viable CD3⁺ T cells. FIG. 15, upper panel, shows the expression of CD70 at the end of the MLR (120 hours after initiation). In parallel cultures in 96-well plates, graded doses of either 1F6-vcMMAE or 1F6- vcAFP were included in the cultures at initiation. DNA synthesis was assayed during the last 16 hours of the 5-day culture by a pulse of $^3$H-TdR. Both 1F6-vcMMAE and 1F6-vcAFP substantially inhibited T cell proliferation (FIG. 15, lower panel). 1F6-vcAFP was more active than 1F6-vcMMAE, with an $IC_{50}$ of approximately 0.1 μg/ml.

In the third system, the effect of 1F6 and 1F6 ADCs on antigen-induced T cell proliferation was examined. To evaluate antigen-specific T cell activation, T cells specific against tetanus toxoid were enriched from PBMC by multiple rounds of antigenic stimulation with tetanus toxoid in the presence of autologous DCs. Before antigenic stimulation of T cells, mature autologous DCs pulsed with tetanus toxoid were prepared as described above. Autologous PBMC were then co-cultured with antigen-pulsed mature DCs at a ratio of 10 PBMC to 1 DC. At the density of 0.25-0.5×10$^6$ PBMCs/ml of RPMI-1640 supplemented with 10% FBS and 2 mM L-glutamine. T cell activation and expansion were allowed to continue for 7 days. Viable T cells were harvested from the culture and re-stimulated with tetanus toxoid-pulsed autologous mature DCs again under conditions identical to those in first round of activation. Two additional, identical rounds of activation were conducted to further enrich for tetanus toxoid-specific T cells.

Figure 16:
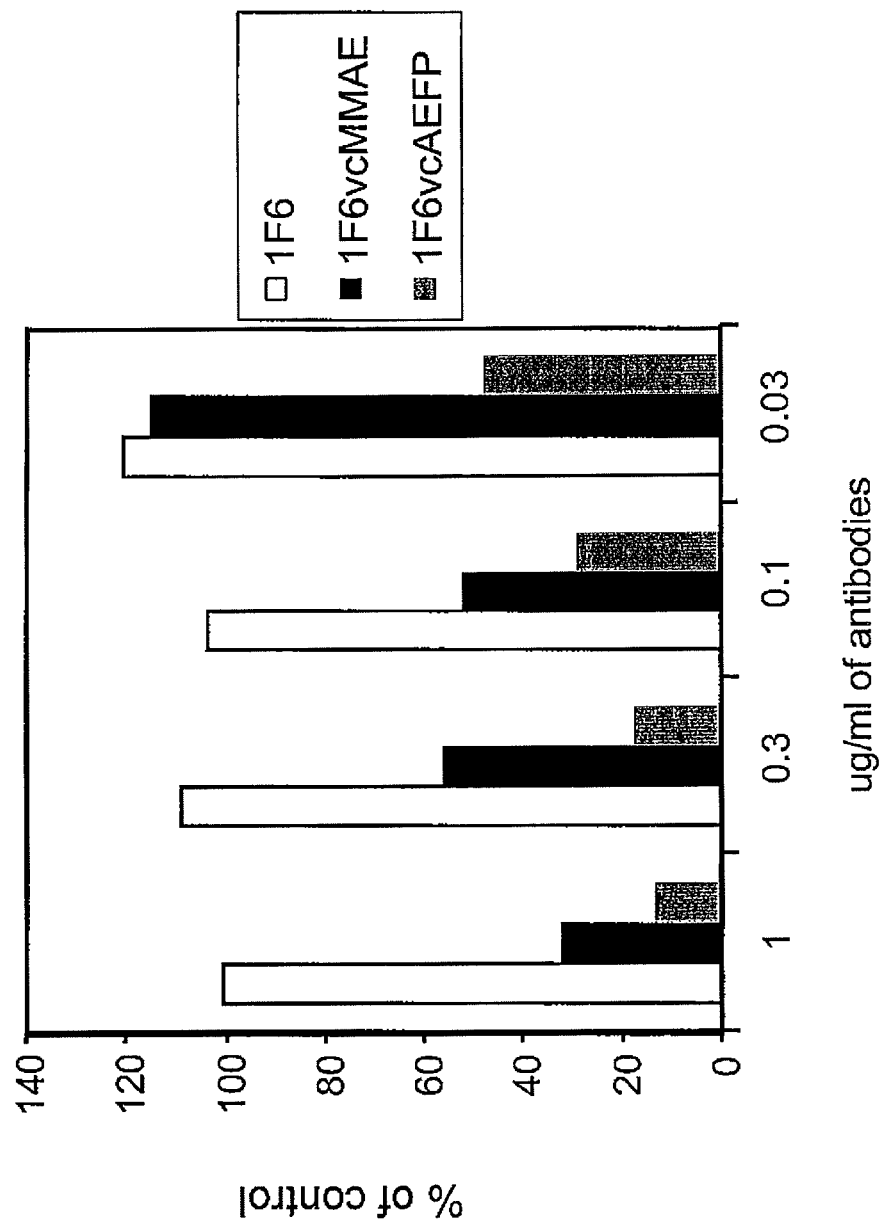
FIG. 16: Effects of anti-CD70 or anti-CD70 ADC on antigen-induced T cell proliferation. T cells enriched for tetanus toxoid reactivity were stimulated with autologous dendritic cells and tetanus toxoid in the presence of graded doses of 1F6, 1F6-vcMMAE, or 1F6-vcAFP for a total of 96 hours. T cell proliferation was determined by pulsing with $^3$H-thymidine during the last 16 hours of incubation.

Tetanus toxoid-specific T cells were enriched and expanded by four consecutive rounds of stimulation by tetanus toxoid and autologous DCs as described above. After the 4th round of stimulation, resting tetanus toxoid-specific T cells were plated in 96-well plates at 20,000 cells/well in the presence of autologous DCs (at 2,000 cells/well) and tetanus toxoid. Graded doses of 1F6, 1F6-vcMMAE, and 1F6-vcAFP were also included in the cultures at the initiation. DNA synthesis was assay during the last 16 hours by $^3$H-TdR incorporation. Unconjugated 1F6 did not show a significant effect on tetanus toxoid-induced T cell proliferation, whereas both 1F6-vcMMAE and 1F6-vcAFP exerted substantial inhibition at doses higher than 0 03 μg/ml (FIG. 16).

EXAMPLE 11

CD70 Expression on Activated T Cells During an Antigen-Specific in Vitro Immune Response A 9-amino acid peptide (GILGFVFTL, M1 peptide; SEQ ID NO:56) derived from the influenza virus matrix protein binds to the peptide-binding groove of the HLA-A0201 molecule. Presentation of the M1 peptide by HLA-A0201 expressing antigen presenting cells to autologous T cells specifically stimulates the activation and expansion of CD8' cytotoxic T cells expressing the T cell receptor V1317 chain (Lehner et al., 1995, *J. Exp. Med.* 181:79-91), constituting a convenient in vitro experimental system to track the activation and expansion of antigen-specific T cells to their cognate antigen.

To examine CD70 expression on activated antigen-specific T cells, PBMCs from a normal donor expressing HLA-A0201 were stimulated with the M1 peptide. PBMCs were seeded at 2×10$^6$ cells/ml with 5 μg/ml of M1 peptide in AIMV medium supplemented with 5% human AB serum. IL-2 (Proleukin, Chiron) and IL-15 (R&D Systems, MN) were added to final concentrations of 20 IU/ml and 5 ng/ml, respectively, once every two days beginning on day 2 after culture initiation. The expansion of CD8$^+$/Vβ17$^+$ T cells and induction of CD70 on the CD8$^+$/Vβ17$^+$ was followed by three-color flow cytometry. Vβ17$^+$ T cells were identified by the anti-TCRVβ17 mAb clone E17.5F3 (Beckman Coulter, Miami, Fla.). Results from a representative experiment are shown in FIGS. 17A and B.

Figure 17B:
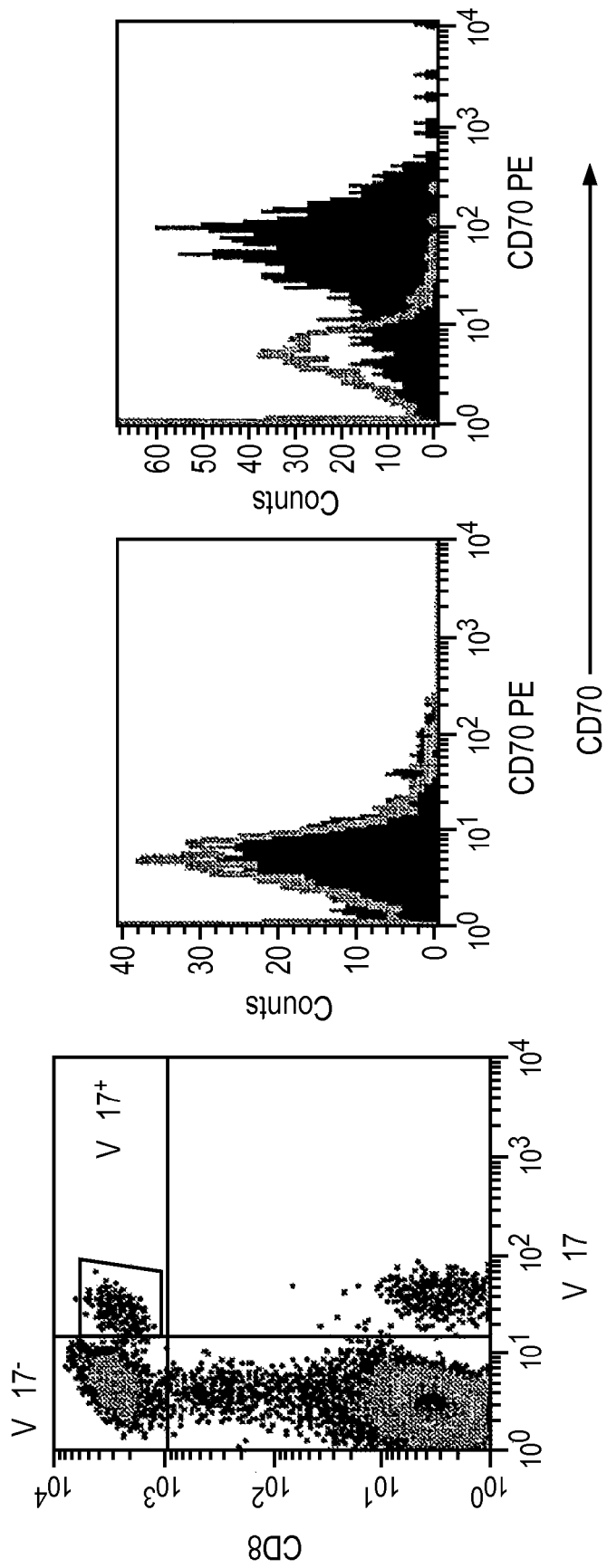
FIG. 17: CD70 induction during antigen-specific T cell expansion. PBMCs from a normal HLA-A0201 donor were stimulated with the M1 peptide derived from the influenza virus matrix protein. (A) Expansion of M1 peptide-specific CD8$^+$ cells expressing TCR Vβ17 chain was followed by flow cytometry (upper panels). The lower left panel shows the percentage of CD8$^+$/Vβ17$^+$ cells expressing CD70 and the lower right panel shows the intensity of CD70 expression on the expanding CD8$^+$/Vβ17$^+$ cells. (B) A representative example of specific CD70 induction on the expanding CD8$^+$/Vβ17$^+$ after stimulation with the M1 peptide for five days. Binding of the control IgG (open curves) and anti-CD70 mAb (closed curves) on the CD8$^+$/Vβ17$^-$ or CD8$^+$/Vβ17$^+$ cells are shown.

FIG. 17A, upper panels, shows that only 0.9% of the cells within the lymphocyte population were CD8$^+$/Vβ17$^+$ two days after culture initiation. T cell expansion was only evident within the CD8$^+$/Vβ17$^+$ population. The percentage of CD8$^+$/Vβ17$^+$ progressively increased to 23% on day 11. CD70 expression became detectable 3 days after antigen stimulation (FIG. 17A, lower panel). On day 7, approximately 60% of the expanding CD8$^+$/Vβ17$^+$ cells expressed CD70 (FIG. 17A, lower left panel). The highest level of CD70 expression as indicated by the mean fluorescence intensity (MFI) was also detected on day 7 (FIG. 17A, lower right panel). The percentage of CD70$^+$/CD8$^+$/Vβ17$^+$ cells and the MFI of CD70 expression on the CD8$^+$/Vβ17$^+$ started to decline thereafter. Whereas CD70 was clearly expressed on the CD8$^+$/Vβ17$^+$ cells, no CD70 could be detected on the CD8$^+$/Vβ17$^-$ cells (FIG. 17B). These results confirmed that CD70 induction was restricted to the activated T cells responding to the antigenic stimulation but not the bystander, antigen non-specific T cells.

EXAMPLE 12

In Vitro Deletion of CD70$^+$ Antigen-Specific T Cells by Anti-CD70 ADCs

PBMCs from a normal donor expressing HLA-A0201 were stimulated with the M1 peptide as described in Example 11. On day 5, cells were harvested, washed, and re-seeded at 0.5-1×10$^6$ cells/ml (approximately 100,000 of CD8$^+$/Vβ17$^+$ T cells) in fresh AIMV medium supplemented with 5% human AB, 20 IU/ml of IL-2, and 5 ng/ml of IL-15. 1F6 or control non-binding IgG (cIgG) ADCs were added to some cultures to a final concentration of 1 μg/ml. Total viable cell counts were conducted 24, 48, and 76 hours after ADC addition. Two-color flow cytometry was conducted to determine the percentages of CD8$^+$/Vβ17$^+$ cells among the viable cells. The absolute number of CD8$^+$/Vβ17$^+$ T cells in each culture was then calculated. The number of CD8$^+$/Vβ17$^+$ T cells in the two control cultures increased to more than 800,000 after 76 hours (FIG. 18, upper panel). Substantial inhibition of CD8$^+$/Nβ17$^+$ T cell expansion was seen in the 1F6 ADC-treated cultures. The number of CD8$^+$/Vβ17$^+$ T cells was approximately 400,000 in the 1F6-vcMMAE-treated culture, compared to >800,000 in the cIgG-vcMMAE-treated culture. Virtually no expansion of CD8$^+$/Vβ17$^+$ T cells occurred in the 1F6-vcAFP-treated culture, whereas >500,000 of CD8$^+$/V≠217$^+$ T cells were present in the cIgG-vcAFP-treated culture. The effects of 1F6 ADCs on the CD8$^+$/Vβ17$^-$ cells were also evaluated. FIG. 18, lower panel, shows that the CD8$^+$/Vβ17$^+$ cells in the 1F6-vcAFP- and 1F6-vcMMAE-treated cultures were <40% and <20%, respectively, of the control untreated culture at the end of the experiment. In contrast, the antigen non-specific bystander, antigen non-specific CD8$^+$/Vβ17$^-$ cells in the ADC-treated cultures were >60% of the untreated culture. These results demonstrate that 1F6 ADCs specifically targeted the CD70$^+$/CD8$^+$/Vβ317$^+$ T cells and exerted limited effects on the CD70$^-$/CD8$^+$/Vβ17$^-$ T cells that co-inhabited the same culture, suggesting limited bystander toxicity of the 1F6 ADCs.

Figure 19:
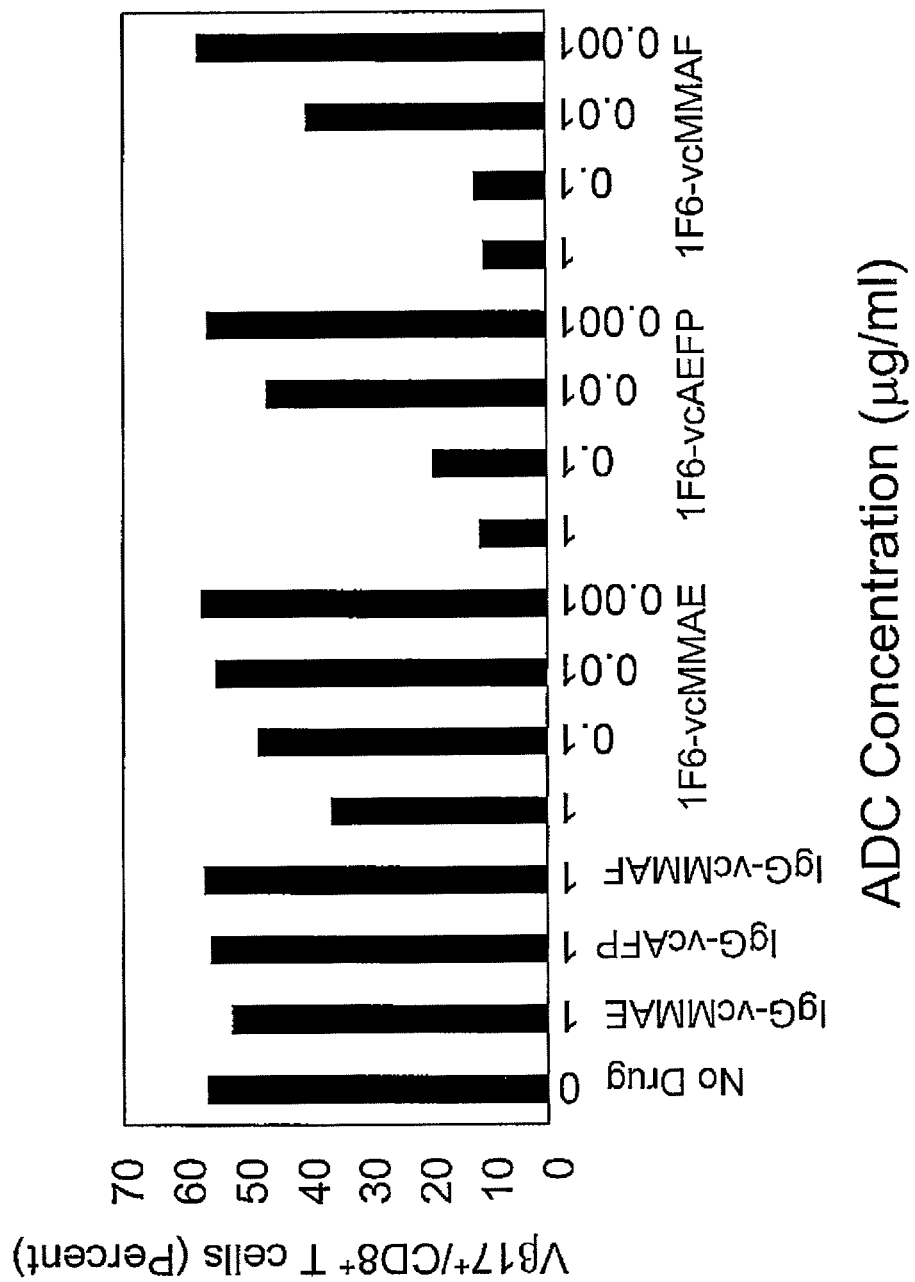
FIG. 19: Dose-response comparison of anti-CD70 ADCs on deletion of antigen-specific CD8$^+$/Vβ17$^+$ cells. PBMCs from a normal HLA-A0201donor were stimulated with the M1 peptide for 5 days. 1F6 ADCs or control non-binding IgG (cIgG) ADCs were given to cells to the specified final concentrations. The percentages of CD8$^+$/Vβ17$^+$ cells 4 days post ADC addition was determined by flow cytometry as in FIG. 17.

The potency of three 1F6 ADCs was then compared. HLA-A0201 PBMCs were stimulated with the M1 peptide and re-seeded as described for FIG. 18 with the various ADCs at the indicated concentrations (FIG. 19). The percent of CD8$^+$/Vβ17$^+$ T cells after a 96-hour incubation was determined. A dose-dependent inhibition of CD8$^+$/Vβ17$^+$ T cell expansion was observed with 1F6-vcMMAE, -vcAFP, and -vcMMAF, while the corresponding IgG control ADCs at the top concentration of 1 µg/ml showed no detectable inhibitory activity compared to the no drug control culture. The $IC_{50}$ values for 1F6-vcAFP and 1F6-vcMMAF were between 0.1 and 0.01 µg/ml. The inhibitory activity of 1F6-vcMMAE appeared to be weaker than both 1F6-vcAFP and 1F6-vcMMAF.

Figure 20:
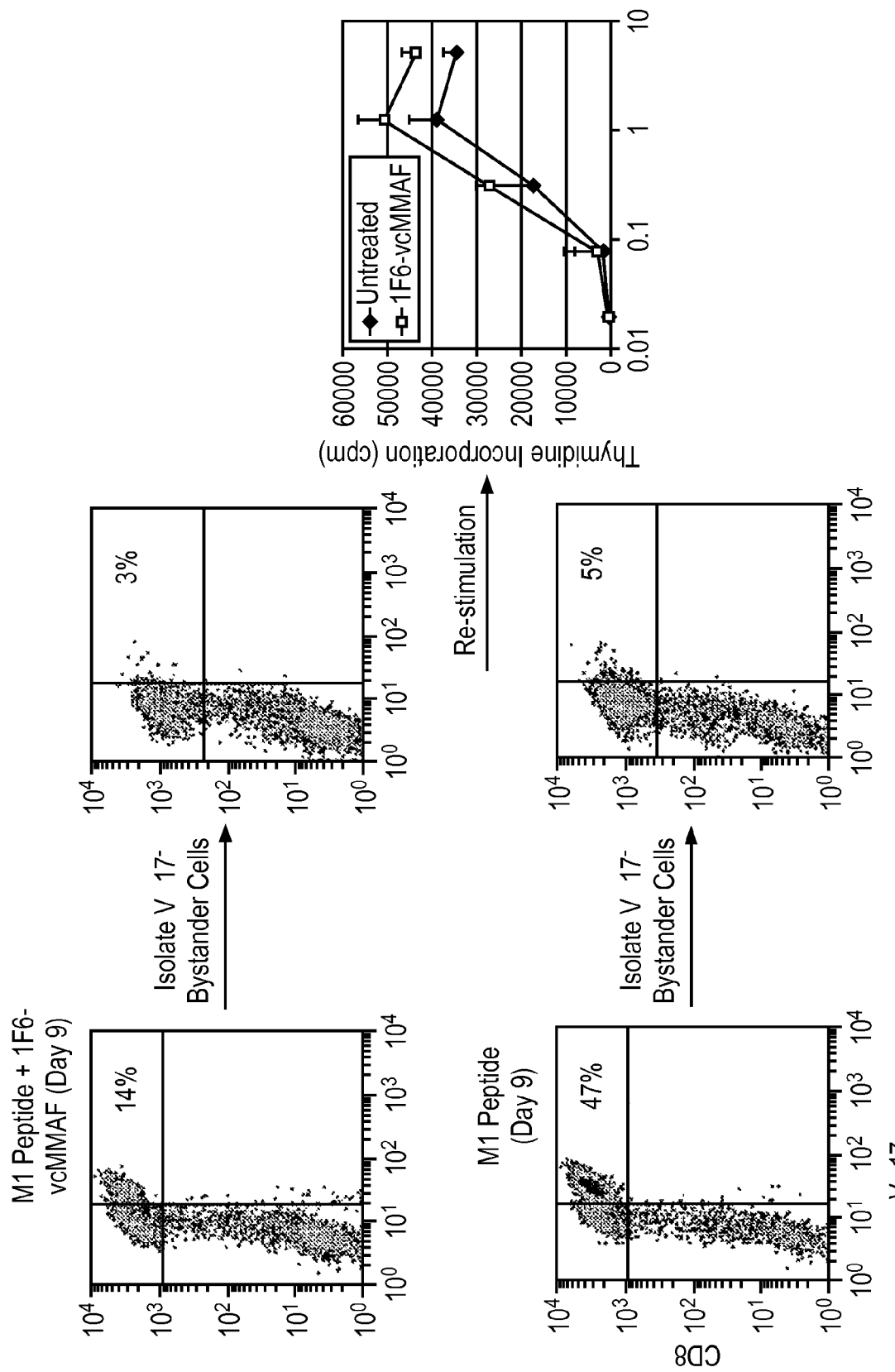
FIG. 20: Limited effects of 1F6 ADCs on the proliferation capacity of the CD70$^-$ bystander T cells. PBMCs from a normal HLA-A0201donor were stimulated with the M1 peptide for 5 days. Cells were either allowed to expand or treated with 1 μg/ml 1F6-vcMMAF for an additional 4 days. Percentages of CD8$^+$/Vβ17$^+$ cells were determined by flow cytometry (left column). In order to assess the proliferation capacity of the CD70$^-$ bystander, antigen non-specific T cells, Vβ17$^+$ T cells were eliminated from the cultures by immuno-depletion (center column). The resulting Vβ17$^-$ cells were then stimulated with graded doses of immobilized anti-CD3 and anti-CD28 mAb for a total of 96 hours, and DNA synthesis was detected by pulsing with $^3$H-TdR during the last 18 hours of incubation.

A re-stimulation assay was used to evaluate the functional capacity of the bystander, antigen non-specific $CD8^+/V\beta17^-$ T cells. HLA-A0201 expressing PBMCs were stimulated with the M1 peptide and then treated with 1 µg/ml of 1F6-vcMMAF on day 5 to delete the $CD70^+/CD8^+/V\beta17^+$ T cells as described in FIGS. 18 and 19. As expected the number of $CD8^+/V\beta17^+$ T cells in the ADC-treated culture was lower than the untreated culture, 14% versus 47% (FIG. 20, left column) Responses of the remaining cells to a mitogenic re-stimulation were assessed. In order to normalize for the number of $V\beta17^-$ T cells used in the re-stimulation assay and minimize the contribution of $CD8^+/V\beta17^+$ T cells to the proliferation response, $V\beta17^-$ T cells were enriched by negative immunoselection. Briefly, day 9 cells were harvested, washed, and resuspended to $5\times10^7$ cells/ml in medium containing an anti-TCRV$\beta$17 mAb (clone E17.5F3) at 1-2 µg/$10^6$ target T cells. After incubation at 4° C. for 30 minutes, unbound anti-TCRV$\beta$17 mAb was removed by washing the cells twice with PBS containing 0.1% human serum. The cells were resuspended at a concentration of $2\text{-}5\times10^6$/ml two washes in medium and Dynabeads M-450 goat anti-mouse IgG paramagnetic beads (Dynal Biotech Inc., Lake Success, N.Y.) were added at a ratio of 4 paramagnetic beads to 1 target T cell. The mixture was rotated at 4° C. for 30 minutes. Paramagnetic beads with bound $V\beta17^+$ T cells were then separated from the rest of the cells by a magnetic device. Remval of $V\beta17^+$ T cells was confirmed by two-color flow cytometry. FIG. 20, middle column, shows that only 3% and 5% of the cells were left in the 1F6-vcMMAF-treated and untreated cultures, respectively. Anti-CD3 and anti-CD28 immobilized onto tissue culture wells at graded concentrations were used to re-stimulate the $V\beta17^-$ cells in the absence of any exogenous IL-2. Twenty thousand $V\beta17^-$ cells were seeded per well in 96-well plates in a total of 200 µl of AIMV medium supplemented with 5% human serum. Cells were cultured for 96 hours, and DNA synthesis was assayed by $^3$H-TdR incorporation during the last 18 hours of culture. $V\beta17^-$ T cells enriched from the 1F6-vcMMAF-treated culture demonstrated a dose-dependent response to anti-CD3 plus anti-CD28 re-stimulation comparable to that of the untreated cells. This suggests that, although the $V\beta17^-$ T cells were incubated with the $CD8^+/V\beta17^+$ cells in the presence of 1F6-vcMMAF for 4 days, they had retained their proliferation capacity. More importantly, their ability to mount a proliferation response in the absence of any exogenous IL-2 illustrates that they were also functionally intact with regard to their ability to express and secrete the necessary cytokine (s) needed for their proliferation. Taken together, these results suggest that anti-CD70 ADCs can selectively delete $CD70^+$ activated T cells without causing substantial collateral damage to bystander T cells. This characteristic suggests that they can be applied as immunosuppressive agents that may have minimum impact on the immune repertoire of the host.

EXAMPLE 13

Treatment of Experimental Allergic Encephalomyelitis by Administration of Anti-CD70 ADCs Studies indicate a role for CD70/CD27-mediated T cell-T cell interactions in enhancing the $Th_1$-mediated immune responses in cell-mediated autoimmune diseases, including, for example, autoimmune demyelinating diseases. In this example, experimental allergic encephalomyelitis (EAE), an animal model of the demyelinating disease multiple sclerosis (MS), is treated with an ADC comprising an antibody that (a) is conjugated to AFP or MMAE with a val-cit (vc) linker and (b) recognizes an epitope of murine CD70 correspoding the 1F6 epitope of human CD70.

Induction and clinical assessment of Experimental allergic encephalomyelitis (EAE): R-EAE (relapsing EAE) is induced in six- to seven-week-old female SJL mice by subcutaneous immunization with 100 µl of complete Freund's adjuvant (CFA) emulsion containing 200 µg of Mycobacterium tuberculosis H37Ra and 40 µg of the immunodominant epitope of proteolipid protein, $PLP_{139-151}$. The signs of EAE are scored on a 0 to 5 scale as follows: (0) normal; (1) limp tail or hind limb weakness; (2) limp tail and hind-limb weakness (waddling gait); (3) partial hind-limb paralysis; (4) complete hind-limb paralysis; and (5) moribund. A relapse is defined as a sustained increase (more than 2 days) in at least one full grade in clinical score after the animal had improved previously at least a full clinical score and had stabilized for at least 2 days. The data are plotted as the mean clinical score for all animals in a particular treatment group or as the relapse rate (total number of relapses in a group divided by the total number of mice in that group).

Anti-CD70 ADC Administration Regimens: Anti-CD70 ADC (0.1-3 mg/kg body weight) is administered intraperitoneally in a total volume of 100 µl. Mice are treated 3 times per week for 3 consecutive weeks (9 total treatments). Treatment is initiated before disease onset (day 7) or at the peak of acute disease (day 14). As a control, one group of EAE-induced mice are left untreated.

Inhibition of INF-$\alpha$ and IFN-$\gamma$ induction: The demonstration of induction of TNF-$\alpha$ and IFN-$\gamma$ in brains of EAE shows an inflammatory disease process indicative of EAE disease progression and inhibition of these cytokines in brains of SJL mice treated with anti-CD70 ADC indicates the value of anti-CD70 ADC therapy in preventing or treating EAE. Brains are obtained from from at least three animals treated preclinically (at day 13, after three treatments, and day 26, after nine treatments) and at peak of acute disease (at day 20, after three treatments, and day 33, after nine treatments). Brains are fixed (10% buffered formalin), and tissues are embedded in paraffin and sectioned. Sections are then independently stained for TNF-$\alpha$ or IFN-$\gamma$ by incubation with a primary antibody specific for the respective cytokine, followed by incubation with a secondary antibody conjugated to FITC. Tissue sections are then mounted in mounting media and analyzed by immunofluorescence microscopy. Decreased levels of TNF-$\alpha$ or INF-$\gamma$ staining in ADC-treated mice versus the untreated EAE-induced mice shows inhibition of inflammatory cytokine induction using anti-CD70 ADC therapy.

Inhibition of Disease Symptoms or Relapse Rates: EAE-induced SIL, mice in the treatment group are compared with untreated EAE-induced mice to assess the efficacy of anti-CD70 ADC therapy in either preventing disease onset or treating established disease. For mice treated preclinically, a decrease in the mean score for EAE disease, as compared to the untreated control group, demonstrates the efficacy of anti-CD70 ADC therapy in preventing disease. For mice treated at the peak of acute disease, either (a) a decrease in the relapse rate or (b) a decrease in the post-treatment mean score for EAE, as compared to the untreated control group, demonstrates the efficacy of anti-CD70 ADC therapy in treating established disease.

EXAMPLE 14

Mouse Xenograft Model of Renal Cell Carcinoma

Figure 21A:
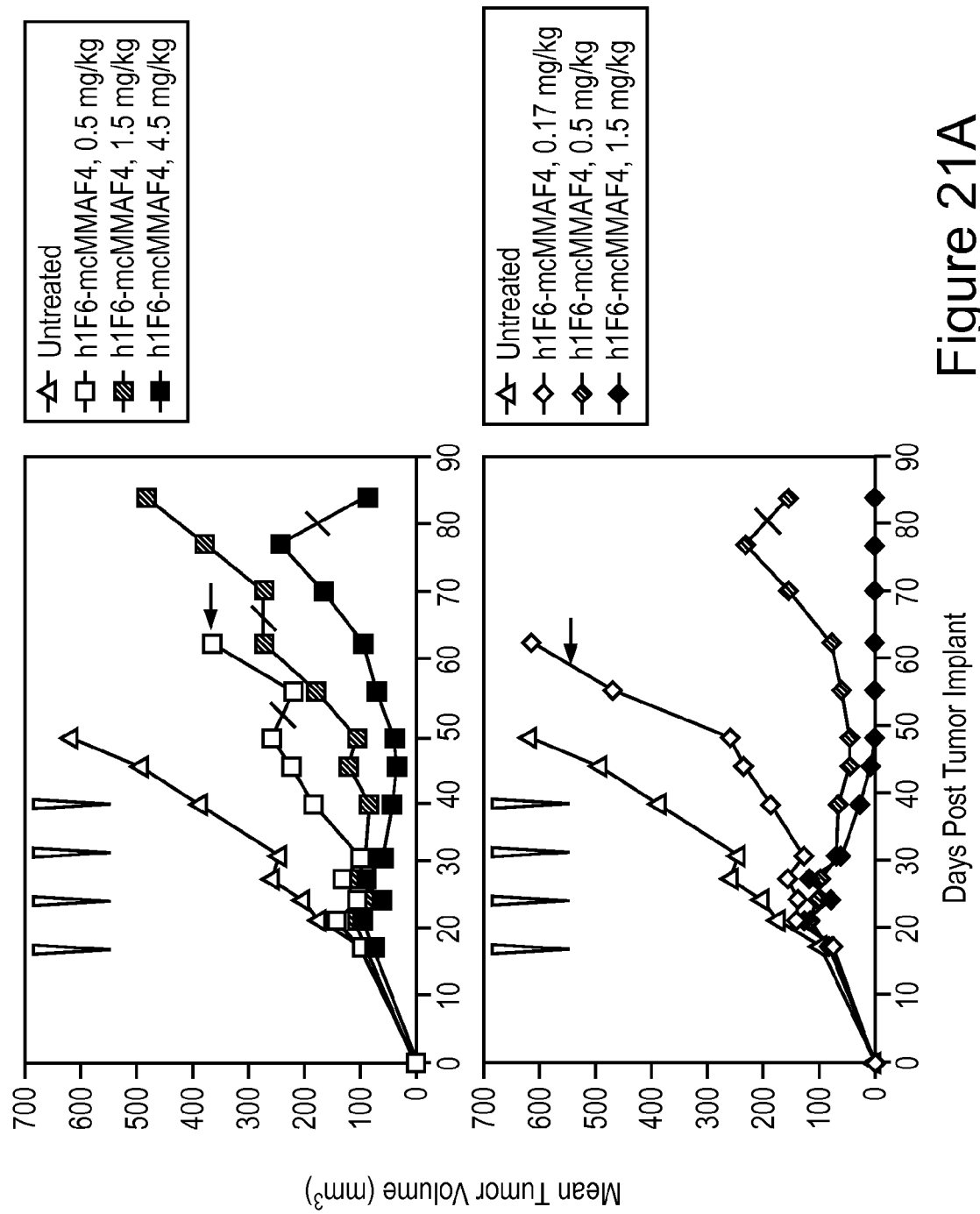
FIG. 21: Mouse Xenograft model of Renal Cell Carcinoma. (A) Subcutaneous 786-O tumors were initiated in nude mice by implanting tumor fragments (N=5 or 6/group) of approximately 30 mm$^3$. Tumor growth was allowed to establish and treatment began when average tumor size within each group was approximately 100 mm$^3$. h1F6-mcMMAF4 or h1F6-vcMMAE4 at the indicated doses was administered at a q4d×4 schedule beginning on day 17 after tumor implantation, as indicated by the arrows. Cross-strikes indicate when animals with tumors>1000 mm$^3$ were euthanized. (B) 786-O tumor implantation and treatment initiation are the same as given in (A). Groups of mice (N=5-7) were administered with h1F6-mcMMAF4 or h1F6-vcMMAE4 at 0.17 mg/kg at a q4d×4 or q4d×10 schedule beginning on day 13 after tumor implantation. Tumor growth is represented by Kaplan-Meier plots. An event was registered when a mouse with a tumor quadrupled in size compared to day 13 when treatment began. Mice with tumor that did not quadruple in size at the end of the experiment on day 43 were censored. The log-rank test was used to generate p values between treatment groups and the untreated group.

A 786-O subcutaneous xenograft model was used to evaluate the antitumor activity of anti-CD70 ADCs administered at different dosages and schedules. Subcutaneous 786-O tumors were initiated in nude mice by implanting tumor fragments (N=5 or 6/group) of approximated 30 mm$^3$. Tumor growth was allowed to establish and treatment began when average tumor size was approximately 100 mm$^3$. Tumor dimensions were determined by caliper measurements to monitor growth. Tumor size was calculated using the formula of (length× width$^2$)/2. In the absence of any treatment, mean tumor volume increased to approximately 600 mm$^3$ within 40 to 50 days after tumor implantation (see FIG. 21A). A dose-dependent effect in tumor growth suppression was observed in mice received either humanized 1F6 (h1F6)-mcMMAF4 (see U.S. Patent Application Publication No. 2005-0238649; loaded with an average of four MMAF molecules per antibody) or h1F6-vcMMAF4 (loaded with an average of four MMAF molecules per antibody). Detectable delay in tumor growth was observed even at 0.5 and 0.17 mg/kg of h1F6-mcMMAF4 and h1F6-vcMMAF4, respectively.

Figure 21B:
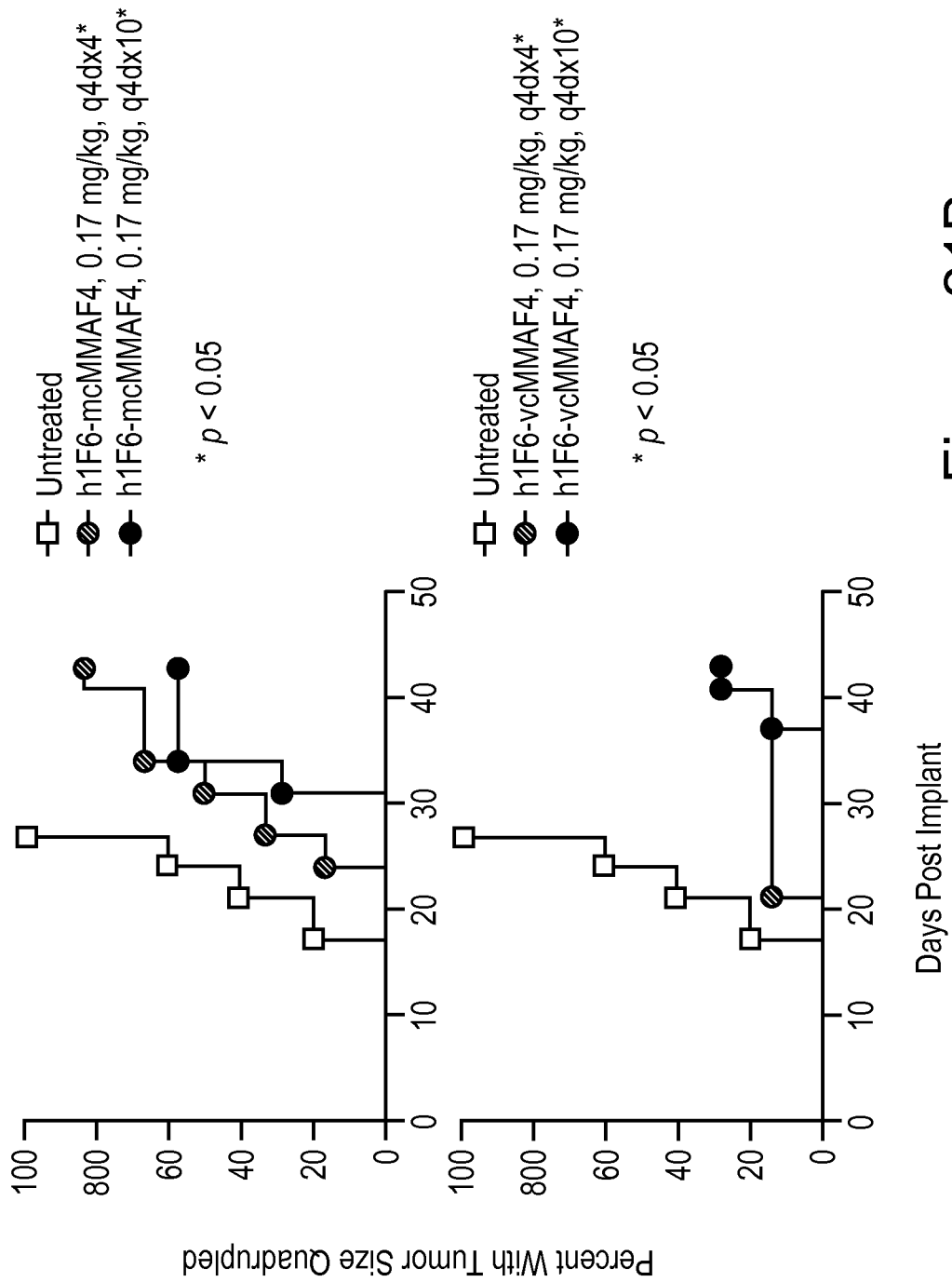

Tumor growth was also assessed by time needed for tumors to quadruple in size (see FIG. 21B). Treatment with either h1F6-mcMMAF4 or h1F6-vcMMAF4 at 0.17 mg/kg significantly delayed the growth of tumors. This delay was observed when the ADCs were given on a q4d×4 or q4d×10 schedule. However, additional administrations as exemplified by the q4d×10 schedule appeared to have a stronger growth inhibitory activity compared to the q4d×4 schedule.

EXAMPLE 15

Expression of CD70 on Multiple Myeloma Cell Lines

Cell surface CD70 expression was evaluated in a panel of multiple myeloma cell lines (Table 3). Copy number of CD70 molecules expressed by each cell line was determined by quantitative flow cytometry using the QIFIKit® (Dako, Carpinteria, Calif.). Response of these cells to anti-CD70 ADC-mediated cytotoxicity was determined. Both chimeric 1F6(c1F6)-vcMMAF4 and c1F6-mcMMAF4 were cytotoxic against CD70-expressing multiple myeloma cells. The IC$_{50}$ values obtained with c1F6-vcMMAF4 ranged from 1.2-160 ng/mL while that obtained with c1F6-mcMMAF4 ranged from 1.7-500 ng/mL.

TABLE 3

Cytotoxic Activity of Anti-CD70 ADCs against Multiple Myeloma Cell Lines

| Cell Line | CD70 copies/cell | IC$_{50}$ (ng/mL) | |
|---|---|---|---|
| | | c1F6-vcMMAF4 | c1F6-mcMMAF4 |
| MM.1S | 14,000 | 20 | 22 |
| MM.1R | 25,000 | 13 | 20 |
| AMO-1 | 92,000 | 16 | 38 |
| JJN-3 | 19,000 | 46 | 61 |
| L363 | 13,000 | 78 | 210 |
| LB | 45,000 | 80 | 500 |
| U266 | 155,000 | 1.2 | 1.7 |
| LP-1 | 34,000 | 160 | 155 |
| MOLP-8 | 9,000 | 73 | 33 |

EXAMPLE 16

Mouse Xenograft Models of Multiple Myeloma

Figure 22A:
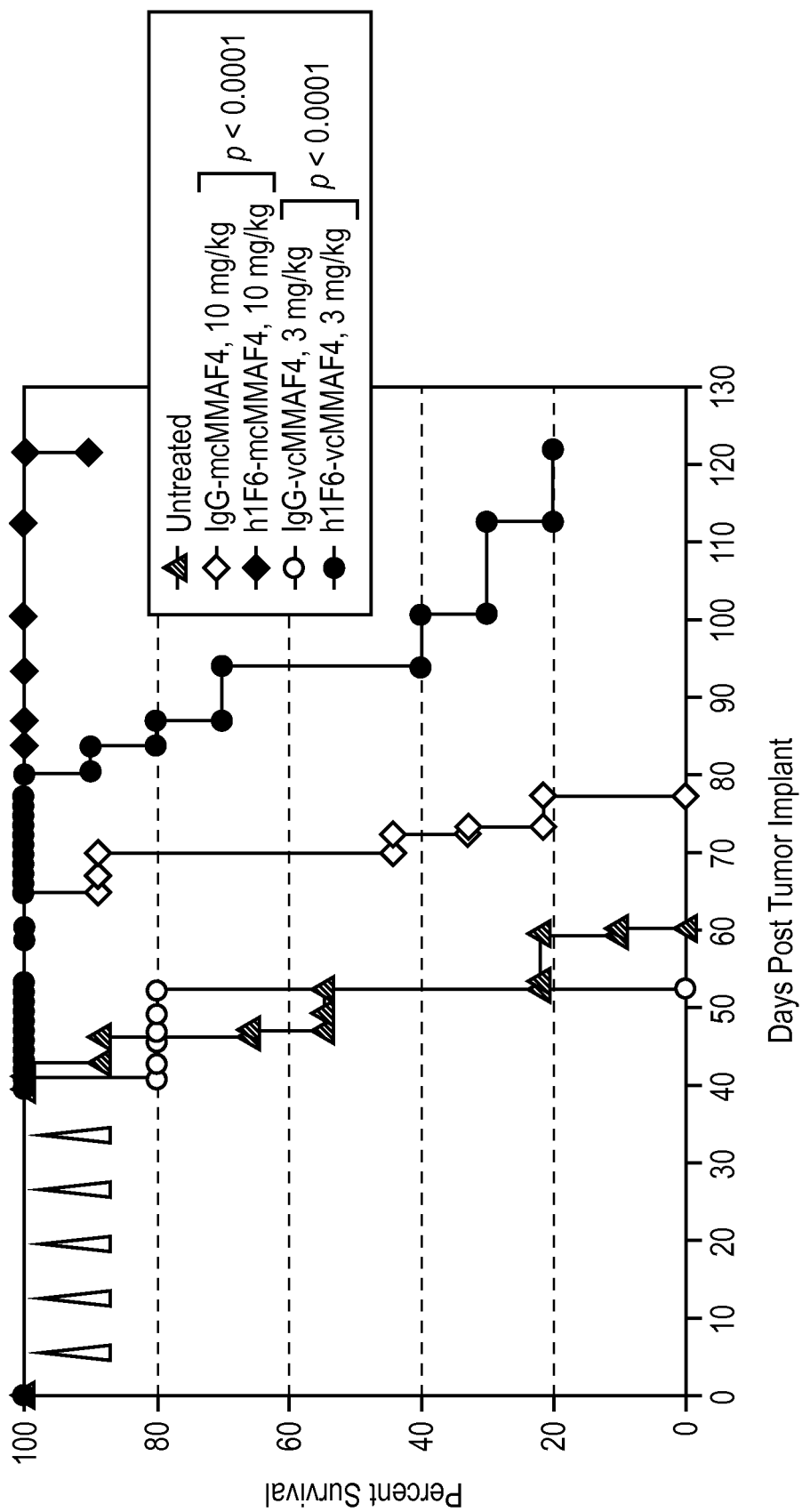
FIG. 22: Mouse Xenograft Model of Multiple Myeloma. (A) Ten million MM-1S cells were injected intravenously into each SCID mouse. Groups of mice (N=8-10) were left untreated, received IgG-vcMMAF4, IgG-mcMMAF4, h1F6-vcMMAF4, or h1F6-mcMMAF4 at the specified doses on a q7d×5 schedule, as indicated by the arrows. Mice showing symptoms of hind limb paralysis, hunched posture, cranial swelling, and/or scruffy coat were euthanized, and the percent survival of each group was plotted. The log-rank test was used to generate p values between treatment groups and the control groups. (B). Bone marrow cells were recovered from the femurs of euthanized mice due to the above disease symptoms or on day 122 post tumor cell implantation when the experiment was terminated. The percentage of CD138-expressing MM-1S cells in the femers of each mouse was determined by flow cytometry. The Mann-Whitney test was used to derived p values between the indicated groups.
Figure 22B:
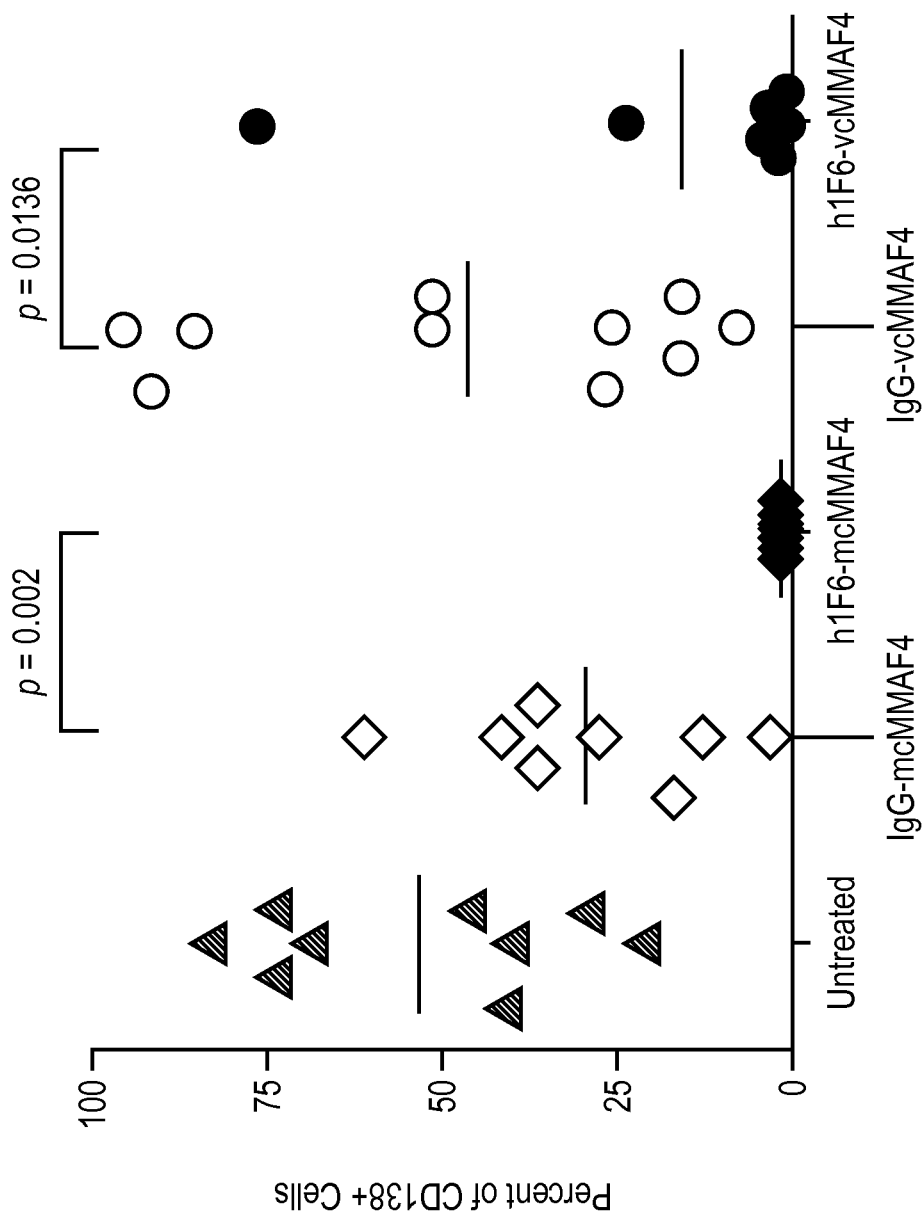

The in vivo activity of anti-CD70 ADCs in xenograft models of multiple myeloma was further examined. Human multiple myeloma cell lines MM-1S or L363 were resuspended in RPMI-1640 medium at the concentration of 10×10$^6$ cells/300 µL. To establish tumors 300 µL of cell suspension were injected intravenously through the tail veins of SCID mice. In the MM-1S model, untreated mice succumbed to the injected tumor cells and manifested symptoms around 40 days post tumor implant including hind limb paralysis, hunched posture, cranial swelling, and/or scruffy coat. Mice were euthanized when they demonstrated one or more of these symptoms. Both h1F6-vcMMAF4 and h1F6-mcMMAF4 provided significant survival benefits to tumor bearing mice compared to control non-binding IgG-vcMMAF4 and IgG-mcMMAF4 (see FIG. 22A). Tumor burden in the MM-1S model was also assessed by enumerating the number of bone marrow cells expressing human CD138, a plasma cell marker expressed by the MM-1S cells. Bone marrow cells were recovered from mice that were euthanized due to manifestation of symptom or at the end of the experiment on day 122, and the number of CD138-expressing MM-1S cells was determined by flow cytometry. Compared to untreated mice, both control IgG-vcMMAF4 and IgG-mcMMAF4 did not significantly reduce the number of CD138-expressing cells in the bone marrow. On the other hand, h1F6-vcMMAF4 and h1F6-mcMMAF4 significantly reduce tumor burden as demonstrated by much lower number of bone marrow CD138-expressing cells compared to the control ADCs (see FIG. 22B).

Figure 23:
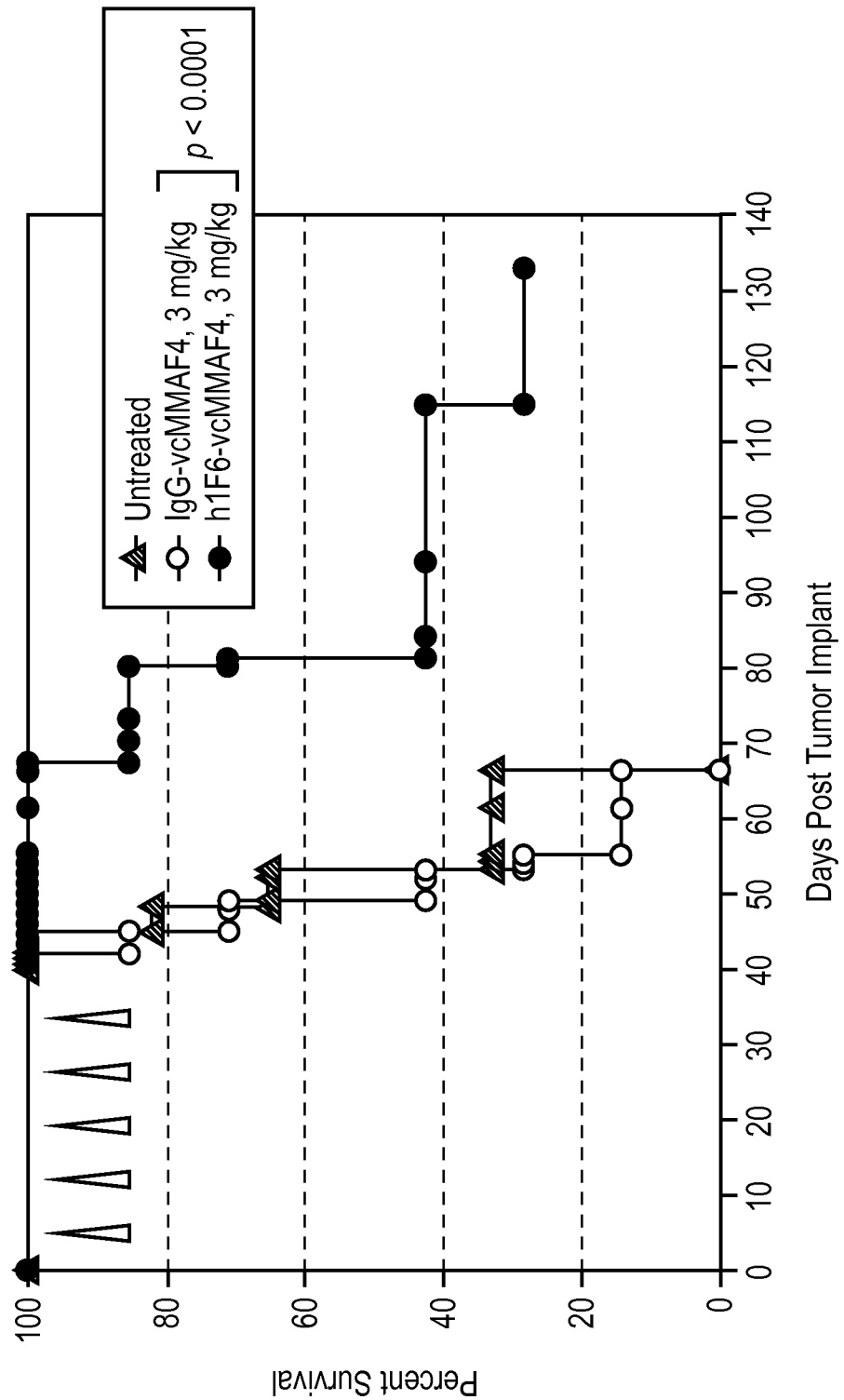
FIG. 23: Mouse Xenograft model of Multiple Myeloma. (A) Ten million L363 cells were injected intravenously into each SCID mouse. Groups of mice (N=7) were left untreated, received IgG-vcMMAF4, or h1F6-vcMMAF4 at the specified doses on a q7d×5 schedule as indicated by the arrows. Mice showing palpable tumor masses were euthanized, and the percent survival of each group was plotted. The log-rank test was used to generate the p value between the treated group and the untreated group. (B) Serum samples were obtained from mice 40 days after tumor implant. The concentration of human λ light chain in the serum of each mice was determined by ELISA. The Mann-Whitney test was used to derived p values between the indicated groups.
Figure 23B:
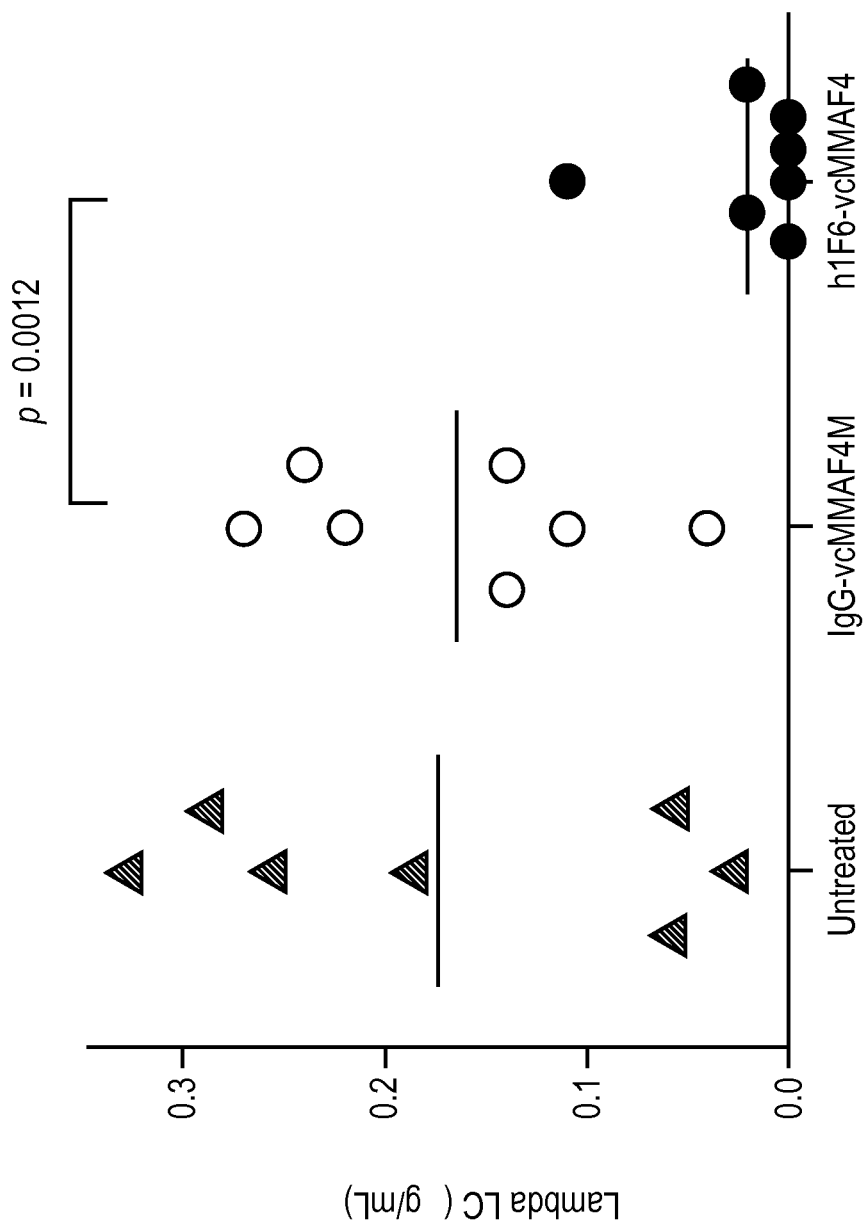

In the L363 model, disseminated tumor masses develop at multiple locations in mice receiving no treatment, and tumor masses became palpable around 40 days after tumor injection, at which tumor bearing mice would be euthanized. Similar to the MM-1S model, control IgG-vcMMAF4 provided no survival advantage, whereas h1F6-vcMMAF4 significantly prolonged survival (see FIG. 23A). Since L363 cells secrete immunoglobulin lambda light chain (λ LC), tumor burden can be determined by monitoring the level of human λ LC in the plasma of tumor bearing mice. An ELISA was used to detect secreted 1 LC. Ninety six-well flat-bottom Immuno plates (Nunc Maxisorp, #442404, Nalge Nunc International, Rochester, N.Y.) was coated with 100 µL/well of goat anti-human Ig (Southern Biotech #2010-01, Birmingham, Ala.) at 2 µg/mL in 0.1M sodium carbonate/bicarbonate overnight at 4° C. Wells were washed 5× with 1× PBST (PBS, 0.05% Tween-20), and blocked with 200 µL/well of 1% BSA/PBST (0.05% Tween-20) for 1 hour at room temperature. After 5 washes with 1× PBST, serially diluted human λ LC-containing mouse serum samples were added. Purified human λ LC (Bethyl labs, #P80-127, Montgomery, Tex.) was used as the standard. After one hour of incubation at room temperature, wells were washed 5 times with 1× PBST. HRP-goat anti-human lambda chain specific F(ab')$_2$ (Southern Biotech #2072-05) at 1:4000 dilution in 1% BSA/PBST was added. After an additional one hour incubation at room temperature, wells were washed 5 times with 1× PBST. TMB substrate 100 µL/well (Sigma, #T8665, St. Louis, Mo.) was used to detect captured λ LC. Forty days after L363 cell implant serum λ LC levels were comparable between the untreated mice and the IgG-vcMMAF4-treated mice (FIG. 23B). In contrast, serum λ LC levels in the h1F6-vcMMAF4-treated mice were significantly lower (FIG. 23B), confirming the ability of anti-CD70 ADC to reduce tumor burden in mice bearing multiple myeloma xenografts.

EXAMPLE 17

Expression of CD70 on Hodkin's and Glioblastoma Cell Lines

Cell surface CD70 expression was also evaluated in panels of Hodgkin's disease (Table 4) and glioblastoma cell lines (Table 5). The copy number of CD70 molecules expressed by each cell line was determined by quantitative flow cytometry using the QIFIKit® (Dako, Carpinteria, Calif.). The response of these cells to anti-CD70 ADC-mediated cytotoxicity was determined. Both chimeric 1F6(c1F6)-vcMMAF4 and c1F6-mcMMAF4 were cytotoxic against these CD70-expressing cell lines. In the Hodgkin's disease panel, the $IC_{50}$ values obtained with c1F6-vcMMAF4 ranged from 0.41-42 ng/mL while that obtained with c1F6-mcMMAF4 ranged from 5.2-310 ng/mL (Table 5). In the glioblastoma panel, the $IC_{50}$ values obtained with h1F6-vcMMAF4 ranged from 2.3-27 ng/mL while that obtained with h1F6-mcMMAF4 ranged from 15-110 ng/mL (Table 4).

TABLE 4

Cytotoxic Activity of Anti-CD70 ADCs against Hodgkin's Disease Cell Lines

| Cell Line | CD70 copies/cell | $IC_{50}$ (ng/mL) c1F6-vcMMAF4 | c1F6-mcMMAF4 |
|---|---|---|---|
| RPMI-6666 | 21,000 | 42 | 230 |
| Hs445 | 64,000 | 7.3 | 310 |
| L428 | 105,000 | 1.4 | 35 |
| KMH2 | 160,000 | 0.41 | 5.2 |
| SUP-HD-1 | 221,000 | 6.3 | 53 |

TABLE 5

Cytotoxic Activity of Anti-CD70 ADCs against Glioblastoma Cell Lines

| Cell Line | CD70 copies/cell | $IC_{50}$ (ng/mL) c1F6-vcMMAF4 | c1F6-mcMMAF4 |
|---|---|---|---|
| U251 | 117,000 | 5.3 | 15 |
| SNB-19 | 90,000 | 12 | 27 |
| U373MG | 70,000 | 16 | 35 |
| GMS-10 | 64,000 | 27 | 110 |
| DBTRG-05MG | 59,000 | 2.3 | 20 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references, including patent applications, patents, and scientific publications, are cited herein, the disclosures of each of which is incorporated herein by reference in its entirety.

---

What is claimed is:

1. A method for the treatment of a CD70-expressing cancer in a subject, the method comprising:
   administering to the subject, in an amount effective for the treatment, an antibody-drug conjugate (ADC) comprising an antibody that binds to CD70 and a cytotoxic agent; wherein the cancer is multiple myeloma.

2. The method of claim 1, wherein the antibody of the ADC competes for binding to CD70 with a monoclonal antibody comprising a heavy chain variable region having the amino acid sequence set forth in SEQ ID NO:50, and a light chain variable region having the amino acid sequence set forth in SEQ ID NO:51.

3. The method of claim 2, wherein the antibody of the ADC comprises H1, H2, H3, L1, L2 and L3 complementarity-determining regions having, respectively, the amino acid sequences set forth in SEQ ID NO:6, SEQ ID NO:8, SEQ ID NO:10; SEQ ID NO:16, SEQ ID NO:18, and SEQ ID NO:20.

4. The method of claim 2, wherein the antibody of the ADC is a humanized antibody.

5. The method of claim 1, wherein the antibody of the ADC competes for binding to CD70 with a monoclonal antibody comprising a heavy chain variable region having the amino acid sequence set forth in SEQ ID NO:52, and a light chain variable region having the amino acid sequence set forth in SEQ ID NO:53.

6. The method of claim 1, wherein the antibody is a chimeric antibody comprising a human constant region.

7. The method of claim 5, wherein the antibody of the ADC comprises H1, H2, H3, L1, L2, and L3 complementarity-determining regions having the amino acid sequences set forth in SEQ ID NO:26, SEQ ID NO:28; SEQ ID NO:30; SEQ ID NO:36, SEQ ID NO:38 and SEQ ID NO:40, respectively.

8. The method of claim 1, wherein the cytotoxic agent is selected from the group consisting of a DNA minor groove binding agent, a DNA minor groove alkylating agent, an enediyne, a duocarmycin, a maytansinoid, and a vinca alkaloid.

9. The method of claim 1, wherein the cytotoxic agent is an anti-tubulin agent.

10. The method of claim 9, wherein the cytotoxic agent is AFP or MMAE.

11. The method of claim 1, wherein the antibody is conjugated to the cytotoxic agent via a linker.

12. The method of claim 11, wherein the linker is cleavable under intracellular conditions.

13. The method of claim 12, wherein the cleavable linker is a peptide linker cleavable by an intracellular protease.

14. The method of claim 13, wherein the peptide linker comprises a dipeptide.

15. The method of claim 14, wherein the dipeptide is a val-cit or a phe-lys dipeptide.

16. The method of claim 1, wherein the subject is human.

17. The method of claim 1, wherein the method comprises:
   administering to the subject in need thereof from about one to about ten suboptimal dosages, over a period of about four to about ten days, of the antibody-drug conjugate.

18. The method of claim 15, wherein the linker comprises the dipeptide val-cit, and the cytotoxic agent is MMAE, MMAF or AFP.

19. The method of claim 1, wherein the antibody blocks binding of CD70 to CD27 receptor.

20. The method of claim 19, wherein the cytotoxic agent is an anti-tubulin agent.

21. The method of claim 20, wherein the anti-tubulin agent is AFP or MMAE.

* * * * *

SEQUENCE LISTING

```
<160> NUMBER OF SEQ ID NOS: 60

<210> SEQ ID NO 1
<211> LENGTH: 411
<212> TYPE: DNA
<213> ORGANISM: Mus sp.

<400> SEQUENCE: 1
atggcttggg tgtggaccct gctattcctg atggcagctg cccaaagtgc ccaagcacag      60
atccagttgg tgcagtctgg acctgaggtg aagaagcctg agagacagt caagatctcc     120 tgcaaggctt ctgggtatac cttcacaaac tatggaatga ctgggtgaa gcaggctcca     180 ggaaagggtt taaagtggat gggctggata aacacctaca ctggagagcc aacatatgct     240
gatgccttca agggacggtt tgccttctct ttggaaacct ctgccagcac tgcctatttg     300
cagatcaaca acctcaaaaa tgaggacacg gctacatatt tctgtgcaag agactacggc     360
gactatggta tggactactg gggtcaagga acctcagtca ccgtctcctc a              411

<210> SEQ ID NO 2
<211> LENGTH: 137
<212> TYPE: PRT
<213> ORGANISM: Mus sp.

<400> SEQUENCE: 2

Met Ala Trp Val Trp Thr Leu Leu Phe Leu Met Ala Ala Ala Gln Ser
1               5                   10                  15
```

```
Ala Gly Ala Gln Ile Gln Leu Val Gln Ser Gly Pro Glu Val Lys Lys
         20                  25                  30
Pro Gly Glu Thr Val Lys Ile Ser Cys Lys Ala Ser Gly Tyr Thr Phe
             35                  40                  45
Thr Asn Tyr Gly Met Asn Trp Val Lys Gln Ala Pro Gly Lys Gly Leu
 50                  55                  60
Lys Trp Met Gly Trp Ile Asn Thr Tyr Thr Gly Glu Pro Thr Tyr Ala
 65                  70                  75                  80
Asp Ala Phe Lys Gly Arg Phe Ala Phe Ser Leu Glu Thr Ser Ala Ser
                 85                  90                  95
Thr Ala Tyr Leu Gln Ile Asn Asn Leu Lys Asn Glu Asp Thr Ala Thr
            100                 105                 110
Tyr Phe Cys Ala Arg Asp Tyr Gly Asp Tyr Gly Met Asp Tyr Trp Gly
        115                 120                 125
Gln Gly Thr Ser Val Thr Val Ser Ser
    130                 135

<210> SEQ ID NO 3
<211> LENGTH: 57
<212> TYPE: DNA
<213> ORGANISM: Mus sp.

<400> SEQUENCE: 3
atggcttggg tgtggacctt gctattcctg atggcagctg cccaaagtgc ccaagca      57

<210> SEQ ID NO 4
<211> LENGTH: 19
<212> TYPE: PRT
<213> ORGANISM: Mus sp.

<400> SEQUENCE: 4

Met Ala Trp Val Trp Thr Leu Leu Phe Leu Met Ala Ala Gln Ser
 1               5                  10                  15
Ala Gly Ala

<210> SEQ ID NO 5
<211> LENGTH: 30
<212> TYPE: DNA
<213> ORGANISM: Mus sp.

<400> SEQUENCE: 5
gggtatacct tcacaaacta tggaatgaac                                     30

<210> SEQ ID NO 6
<211> LENGTH: 10
<212> TYPE: PRT
<213> ORGANISM: Mus sp.

<400> SEQUENCE: 6

Gly Tyr Thr Phe Thr Asn Tyr Gly Met Asn
 1               5                  10

<210> SEQ ID NO 7
<211> LENGTH: 51
<212> TYPE: DNA
<213> ORGANISM: Mus sp.

<400> SEQUENCE: 7
tggataaaca cctacactgg agagccaaca tatgctgatg ccttcaaggg a             51

<210> SEQ ID NO 8
```

```
<211> LENGTH: 17
<212> TYPE: PRT
<213> ORGANISM: Mus sp.

<400> SEQUENCE: 8

Trp Ile Asn Thr Tyr Thr Gly Glu Pro Thr Tyr Ala Asp Ala Phe Lys
1               5                   10                  15

Gly

<210> SEQ ID NO 9
<211> LENGTH: 27
<212> TYPE: DNA
<213> ORGANISM: Mus sp.

<400> SEQUENCE: 9
gactacggcg actatggtat ggactac                                              27

<210> SEQ ID NO 10
<211> LENGTH: 9
<212> TYPE: PRT
<213> ORGANISM: Mus sp.

<400> SEQUENCE: 10

Asp Tyr Gly Asp Tyr Gly Met Asp Tyr
1               5

<210> SEQ ID NO 11
<211> LENGTH: 396
<212> TYPE: DNA
<213> ORGANISM: Mus sp.

<400> SEQUENCE: 11
atggagacag acacactcct gttatgggta ctgctgctct gggttccagg ttccactggt         60
gacattgtgc tgacacagtc tcctgcttcc ttagctgtat ctctggggca gagggccacc        120
atctcatgca gggccagcaa aagtgtcagt acatctggct atagtttat gcactggtat         180 caacagaaac caggacagcc acccaaactc ctcatctatc ttgcatccaa cctagaatct        240
ggggtccctg ccaggttcag tggcagtggg tctgggacag acttcaccct caacatccat        300
cctgtggagg aggaggatgc tgcaacctat tactgtcagc acagtaggga ggttccgtgg        360
acgttcggtg aggcaccaa gctggaaatc aaacgg                                   396

<210> SEQ ID NO 12
<211> LENGTH: 132
<212> TYPE: PRT
<213> ORGANISM: Mus sp.

<400> SEQUENCE: 12

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Arg Ala Ser Lys Ser
            35                  40                  45

Val Ser Thr Ser Gly Tyr Ser Phe Met His Trp Tyr Gln Gln Lys Pro
        50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95
```

-continued

Leu Asn Ile His Pro Val Glu Glu Asp Ala Ala Thr Tyr Tyr Cys
                100                 105                 110

Gln His Ser Arg Glu Val Pro Trp Thr Phe Gly Gly Gly Thr Lys Leu
        115                 120                 125

Glu Ile Lys Arg
    130

<210> SEQ ID NO 13
<211> LENGTH: 60
<212> TYPE: DNA
<213> ORGANISM: Mus sp.

<400> SEQUENCE: 13
atggagacag acacactcct gttatgggta ctgctgctct gggttccagg ttccactggt    60

<210> SEQ ID NO 14
<211> LENGTH: 20
<212> TYPE: PRT
<213> ORGANISM: Mus sp.

<400> SEQUENCE: 14

Met Glu Thr Asp Thr Leu Leu Leu Trp Val Leu Leu Leu Trp Val Pro
1               5                   10                  15

Gly Ser Thr Gly
            20

<210> SEQ ID NO 15
<211> LENGTH: 45
<212> TYPE: DNA
<213> ORGANISM: Mus sp.

<400> SEQUENCE: 15
agggccagca aaagtgtcag tacatctggc tatagtttta tgcac    45

<210> SEQ ID NO 16
<211> LENGTH: 15
<212> TYPE: PRT
<213> ORGANISM: Mus sp.

<400> SEQUENCE: 16

Arg Ala Ser Lys Ser Val Ser Thr Ser Gly Tyr Ser Phe Met His
1               5                   10                  15

<210> SEQ ID NO 17
<211> LENGTH: 21
<212> TYPE: DNA
<213> ORGANISM: Mus sp.

<400> SEQUENCE: 17
cttgcatcca acctagaatc t    21

<210> SEQ ID NO 18
<211> LENGTH: 7
<212> TYPE: PRT
<213> ORGANISM: Mus sp.

<400> SEQUENCE: 18

Leu Ala Ser Asn Leu Glu Ser
1               5

<210> SEQ ID NO 19
<211> LENGTH: 27
<212> TYPE: DNA
<213> ORGANISM: Mus sp.

<400> SEQUENCE: 19
cagcacagta gggaggttcc gtggacg                                              27

<210> SEQ ID NO 20
<211> LENGTH: 9
<212> TYPE: PRT
<213> ORGANISM: Mus sp.

<400> SEQUENCE: 20

Gln His Ser Arg Glu Val Pro Trp Thr
1               5

<210> SEQ ID NO 21
<211> LENGTH: 411
<212> TYPE: DNA
<213> ORGANISM: Mus sp.

<400> SEQUENCE: 21
atggaatgga cctgggtctt tctcttcctc ctgccagtaa ctgcagatgt ccaatcccag     60
gttcagctgc aacagtctgg aactgagctg atgacgcctg ggcctcagt gacgatgtcc    120 tgcaagactt ctggctacac attcagtacc tactggatag agtgggtaaa acagaggcct    180
ggacatggcc ttgagtggat tggagaaatt ttacctggaa gtggttatac tgactacaat    240
gagaagttca aggccaaggc cacattcact gcagatacat cctccaacac agcctacatg    300
caactcagca gcctggcatc tgaggactct gccgtctatt actgtgcaag atgggatagg    360
ctctatgcta tggactactg gggtcaagga acctcagtca ccgtctcctc a             411

<210> SEQ ID NO 22
<211> LENGTH: 137
<212> TYPE: PRT
<213> ORGANISM: Mus sp.

<400> SEQUENCE: 22

Met Glu Trp Thr Trp Val Phe Leu Phe Leu Leu Ser Val Thr Ala Asp
1               5                   10                  15

Val Gln Ser Gln Val Gln Leu Gln Gln Ser Gly Thr Glu Leu Met Thr
                20                  25                  30

Pro Gly Ala Ser Val Thr Met Ser Cys Lys Thr Ser Gly Tyr Thr Phe
            35                  40                  45

Ser Thr Tyr Trp Ile Glu Trp Val Lys Gln Arg Pro Gly His Gly Leu
        50                  55                  60

Glu Trp Ile Gly Glu Ile Leu Pro Gly Ser Gly Tyr Thr Asp Tyr Asn
65                  70                  75                  80

Glu Lys Phe Lys Ala Lys Ala Thr Phe Thr Ala Asp Thr Ser Ser Asn
                85                  90                  95

Thr Ala Tyr Met Gln Leu Ser Ser Leu Ala Ser Glu Asp Ser Ala Val
            100                 105                 110

Tyr Tyr Cys Ala Arg Trp Asp Arg Leu Tyr Ala Met Asp Tyr Trp Gly
        115                 120                 125

Gly Gly Thr Ser Val Thr Val Ser Ser
    130                 135

<210> SEQ ID NO 23
<211> LENGTH: 57
<212> TYPE: DNA
<213> ORGANISM: Mus sp.

<400> SEQUENCE: 23

```
atggaatgga cctgggtctt tctcttcctc ctgtcagtaa ctgcagatgt ccaatcc        57
```

<210> SEQ ID NO 24
<211> LENGTH: 19
<212> TYPE: PRT
<213> ORGANISM: Mus sp.

<400> SEQUENCE: 24

Met Glu Trp Thr Trp Val Phe Leu Phe Leu Leu Ser Val Thr Ala Asp
1               5                   10                  15

Val Gln Ser

<210> SEQ ID NO 25
<211> LENGTH: 30
<212> TYPE: DNA
<213> ORGANISM: Mus sp.

<400> SEQUENCE: 25

```
ggctacacat tcagtaccta ctggatagag                                     30
```

<210> SEQ ID NO 26
<211> LENGTH: 10
<212> TYPE: PRT
<213> ORGANISM: Mus sp.

<400> SEQUENCE: 26

Gly Tyr Thr Phe Ser Thr Tyr Trp Ile Glu
1               5                   10

<210> SEQ ID NO 27
<211> LENGTH: 51
<212> TYPE: DNA
<213> ORGANISM: Mus sp.

<400> SEQUENCE: 27

```
gaaattttac ctggaagtgg ttatactgac tacaatgaga agttcaaggc c             51
```

<210> SEQ ID NO 28
<211> LENGTH: 17
<212> TYPE: PRT
<213> ORGANISM: Mus sp.

<400> SEQUENCE: 28

Glu Ile Leu Gly Pro Ser Gly Tyr Thr Asp Tyr Asn Glu Lys Phe Lys
1               5                   10                  15

Ala

<210> SEQ ID NO 29
<211> LENGTH: 27
<212> TYPE: DNA
<213> ORGANISM: Mus sp.

<400> SEQUENCE: 29

```
tgggataggc tctatgctat ggactac                                        27
```

<210> SEQ ID NO 30
<211> LENGTH: 9
<212> TYPE: PRT
<213> ORGANISM: Mus sp.

<400> SEQUENCE: 30

Trp Asp Arg Leu Tyr Ala Met Asp Tyr
1               5

```
<210> SEQ ID NO 31
<211> LENGTH: 396
<212> TYPE: DNA
<213> ORGANISM: Mus sp.

<400> SEQUENCE: 31
atggagacag acacactcct gttatgggta ctgctgctct gggttccagg ttccactggt    60
gacattgtgc tgacacagtc tcctgcttcc ttaactgtat ctctgggca aagaccacc    120 atctcatgca gggccagcaa gagtgtcagt acatctggct atagttttat gcactggtac   180
caactgaaac aggacagtc acccaaactc ctcatctatc ttgcgtccaa cctaccatct    240
ggggtccctg ccaggttcag tggcagtggg tctgggacag acttcaccct caaaatccat   300
cctgtggagg aggaggatgc tgcaacctat tactgtcagc acagtaggga gattccgtac   360
acgttcggag gggggaccaa gctggaaata cacgg                              396

<210> SEQ ID NO 32
<211> LENGTH: 132
<212> TYPE: PRT
<213> ORGANISM: Mus sp.

<400> SEQUENCE: 32

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Thr
            20                  25                  30

Val Ser Leu Gly Gln Lys Thr Thr Ile Ser Cys Arg Ala Ser Lys Ser
        35                  40                  45

Val Ser Thr Ser Gly Tyr Ser Phe Met His Trp Tyr Gln Leu Lys Pro
    50                  55                  60

Gly Gln Ser Pro Lys Leu Leu Ile Tyr Leu Ala Ser Asp Leu Pro Ser
65                  70                  75                  80

Gly Val Pro Ala Arg Phe Ser Gly Ser Gly Ser Gly Thr Asp Phe Thr
                85                  90                  95

Leu Lys Ile His Pro Val Glu Glu Glu Asp Ala Ala Thr Tyr Tyr Cys
            100                 105                 110

Gln His Ser Arg Glu Ile Pro Tyr Thr Phe Gly Gly Gly Thr Lys Leu
        115                 120                 125

Glu Ile Thr Arg
    130

<210> SEQ ID NO 33
<211> LENGTH: 60
<212> TYPE: DNA
<213> ORGANISM: Mus sp.

<400> SEQUENCE: 33
atggagacag acacactcct gttatgggta ctgctgctct gggttccagg ttccactggt    60

<210> SEQ ID NO 34
<211> LENGTH: 20
<212> TYPE: PRT
<213> ORGANISM: Mus sp.

<400> SEQUENCE: 34

Met Glu Thr Asp Thr Leu Leu Leu Trp Val Leu Leu Leu Trp Val Pro
1               5                   10                  15

Gly Ser Thr Gly
```

```
<210> SEQ ID NO 35
<211> LENGTH: 45
<212> TYPE: DNA
<213> ORGANISM: Mus sp.

<400> SEQUENCE: 35
agggccagca agagtgtcag tacatctggc tatagttttta tgcac          45

<210> SEQ ID NO 36
<211> LENGTH: 15
<212> TYPE: PRT
<213> ORGANISM: Mus sp.

<400> SEQUENCE: 36

Arg Ala Ser Lys Ser Val Ser Thr Ser Gly Tyr Ser Phe Met His
1               5                   10                  15

<210> SEQ ID NO 37
<211> LENGTH: 21
<212> TYPE: DNA
<213> ORGANISM: Mus sp.

<400> SEQUENCE: 37
cttgcgtcca acctaccatc t                                      21

<210> SEQ ID NO 38
<211> LENGTH: 7
<212> TYPE: PRT
<213> ORGANISM: Mus sp.

<400> SEQUENCE: 38

Leu Ala Ser Asn Leu Pro Ser
1               5

<210> SEQ ID NO 39
<211> LENGTH: 28
<212> TYPE: DNA
<213> ORGANISM: Mus sp.

<400> SEQUENCE: 39
cagcacagta gggagattcc gtacacgt                               28

<210> SEQ ID NO 40
<211> LENGTH: 9
<212> TYPE: PRT
<213> ORGANISM: Mus sp.

<400> SEQUENCE: 40

Gln His Ser Arg Glu Ile Pro Tyr Thr
1               5

<210> SEQ ID NO 41
<211> LENGTH: 25
<212> TYPE: DNA
<213> ORGANISM: Artificial Sequence
<220> FEATURE:
<223> OTHER INFORMATION: primer mIgcK1

<400> SEQUENCE: 41
cttccacttg acattgatgt ctttg                                  25

<210> SEQ ID NO 42
<211> LENGTH: 22
```

```
<212> TYPE: DNA
<213> ORGANISM: Artificial Sequence
<220> FEATURE:
<223> OTHER INFORMATION: primer mIgG1

<400> SEQUENCE: 42
caggtcactg tcactggctc ag                                              22

<210> SEQ ID NO 43
<211> LENGTH: 37
<212> TYPE: DNA
<213> ORGANISM: Artificial Sequence
<220> FEATURE:
<223> OTHER INFORMATION: forward primer

<400> SEQUENCE: 43
gtcgatgagc tctagaattc gtgcccccc cccccc                                37

<210> SEQ ID NO 44
<211> LENGTH: 47
<212> TYPE: DNA
<213> ORGANISM: Artificial Sequence
<220> FEATURE:
<223> OTHER INFORMATION: primer HBS-mck

<400> SEQUENCE: 44
cgtcatgtcg acggatccaa gcttcaagaa gcacacgact gaggcac                   47

<210> SEQ ID NO 45
<211> LENGTH: 47
<212> TYPE: DNA
<213> ORGANISM: Artificial Sequence
<220> FEATURE:
<223> OTHER INFORMATION: primer HBS-mG1

<400> SEQUENCE: 45
cgtcatgtcg acggatccaa gcttgtcacc atggagttag tttgggc                   47

<210> SEQ ID NO 46
<211> LENGTH: 354
<212> TYPE: DNA
<213> ORGANISM: Artificial Sequence
<220> FEATURE:
<223> OTHER INFORMATION: Mature 1F6 Heavy Chain Variable region from
      Figure 1

<400> SEQUENCE: 46
cagatccagt tggtgcagtc tggacctgag gtgaagaagc ctggagagac agtcaagatc     60
tcctgcaagg cttctgggta taccttcaca aactatggaa tgaactgggt gaagcaggct    120
ccaggaaagg gtttaaagtg gatgggctgg ataaacacct acactggaga gccaacatat    180
gctgatgcct tcaagggacg gtttgccttc tctttggaaa cctctgccag cactgcctat    240
ttgcagatca caaccctcaa aaatgaggac acggctacat atttctgtgc aagagactac    300
ggcgactatg gtatggacta ctggggtcaa ggaacctcag tcaccgtctc ctca          354

<210> SEQ ID NO 47
<211> LENGTH: 336
<212> TYPE: DNA
<213> ORGANISM: Artificial Sequence
<220> FEATURE:
<223> OTHER INFORMATION: Mature 1F6 Light Chain Variable Region from
      Figure 1

<400> SEQUENCE: 47
gacattgtgc tgacacagtc tcctgcttcc ttagctgtat ctctggggca gagggccacc     60
```

```
atctcatgca gggccagcaa aagtgtcagt acatctggct atagtttat gcactggtat      120 caacagaaac caggacagcc acccaaactc ctcatctatc ttgcatccaa cctagaatct      180
ggggtccctg ccaggttcag tggcagtggg tctgggacag acttcaccct caacatccat      240
cctgtggagg aggaggatgc tgcaacctat tactgtcagc acagtaggga ggttccgtgg      300
acgttcggtg gaggcaccaa gctggaaatc aaacgg                                336

<210> SEQ ID NO 48
<211> LENGTH: 354
<212> TYPE: DNA
<213> ORGANISM: Artificial Sequence
<220> FEATURE:
<223> OTHER INFORMATION: Mature 2F2 Heavy Chain Variable Region from
      Figure 2

<400> SEQUENCE: 48
caggttcagc tgcaacagtc tggaactgag ctgatgacgc tgggggcctc agtgacgatg       60
tcctgcaaga cttctggcta cacattcagt acctactgga tagagtgggt aaaacagagg      120
cctggacatg gccttgagtg gattggagaa attttacctg gaagtggtta tactgactac      180
aatgagaagt tcaaggccaa ggccacattc actgcagata catcctccaa cacagcctac      240
atgcaactca gcagcctggc atctgaggac tctgccgtct attactgtgc aagatgggat      300
aggctctatg ctatggacta ctggggtcaa ggaacctcag tcaccgtctc ctca             354

<210> SEQ ID NO 49
<211> LENGTH: 336
<212> TYPE: DNA
<213> ORGANISM: Artificial Sequence
<220> FEATURE:
<223> OTHER INFORMATION: Mature 2F2 Light Chain Variable Region from
      Figure 2

<400> SEQUENCE: 49
gacattgtgc tgacacagtc tcctgcttcc ttaactgtat ctctggggca aagaccacc        60 atctcatgca gggccagcaa gagtgtcagt acatctggct atagtttat gcactggtac       120 caactgaaac caggacagtc acccaaactc ctcatctatc ttgcgtccaa cctaccatct      180
ggggtccctg ccaggttcag tggcagtggg tctgggacag acttcaccct caaaatccat      240
cctgtggagg aggaggatgc tgcaacctat tactgtcagc acagtaggga gattccgtac      300
acgttcggag gggggaccaa gctggaaata acacgg                                336

<210> SEQ ID NO 50
<211> LENGTH: 118
<212> TYPE: PRT
<213> ORGANISM: Artificial Sequence
<220> FEATURE:
<223> OTHER INFORMATION: Mature 1F6 Heavy Chain Variable region from
      Figure 1

<400> SEQUENCE: 50

Gln Ile Gln Leu Val Gln Ser Gly Pro Glu Val Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Ala Phe
    50                  55                  60
```

```
Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Asp Tyr Gly Asp Tyr Gly Met Asp Tyr Trp Gly Gln Gly Thr
            100                 105                 110

Ser Val Thr Val Ser Ser
        115

<210> SEQ ID NO 51
<211> LENGTH: 112
<212> TYPE: PRT
<213> ORGANISM: Artificial Sequence
<220> FEATURE:
<223> OTHER INFORMATION: Mature 1F6 Light Chain Variable Region from
      Figure 1

<400> SEQUENCE: 51

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                 85                  90                  95

Glu Val Pro Trp Thr Phe Gly Gly Gly Thr Lys Leu Glu Ile Lys Arg
            100                 105                 110

<210> SEQ ID NO 52
<211> LENGTH: 118
<212> TYPE: PRT
<213> ORGANISM: Artificial Sequence
<220> FEATURE:
<223> OTHER INFORMATION: Mature 2F2 Heavy Chain Variable Region from
      Figure 2

<400> SEQUENCE: 52

Gln Val Gln Leu Gln Gln Ser Gly Thr Glu Leu Met Thr Pro Gly Ala
 1               5                  10                  15

Ser Val Thr Met Ser Cys Lys Thr Ser Gly Tyr Thr Phe Glu Trp Ile
            20                  25                  30

Ser Thr Tyr Trp Ile Glu Trp Val Lys Gln Arg Pro Gly His Gly Leu
        35                  40                  45

Gly Glu Ile Leu Gly Pro Ser Gly Tyr Thr Asp Tyr Asn Glu Lys Phe
 50                  55                  60

Lys Ala Lys Ala Thr Phe Thr Ala Asp Thr Ser Ser Asn Thr Ala Tyr
 65                  70                  75                  80

Met Gln Leu Ser Ser Leu Ala Ser Glu Asp Ser Ala Val Tyr Tyr Cys
                 85                  90                  95

Ala Arg Trp Asp Arg Leu Tyr Ala Met Asp Tyr Trp Gly Gly Gly Thr
            100                 105                 110

Ser Val Thr Val Ser Ser
        115
```

```
<210> SEQ ID NO 53
<211> LENGTH: 112
<212> TYPE: PRT
<213> ORGANISM: Artificial Sequence
<220> FEATURE:
<223> OTHER INFORMATION: Mature 2F2 Light Chain Variable Region from
      Figure 2

<400> SEQUENCE: 53
```

Asp Ile Val Leu Thr Gln Ser Pro Ala Ser Leu Thr Val Ser Leu Gly
1               5                   10                  15

Gln Lys Thr Thr Ile Ser Cys Arg Ala Ser Lys Ser Val Ser Thr Ser
            20                  25                  30

Gly Tyr Ser Phe Met His Trp Tyr Gln Leu Lys Pro Gly Gln Ser Pro
        35                  40                  45

Lys Leu Leu Ile Tyr Leu Ala Ser Asn Leu Pro Ser Gly Val Pro Ala
    50                  55                  60

Arg Phe Ser Gly Ser Gly Ser Gly Thr Asp Phe Thr Leu Lys Ile His
65                  70                  75                  80

Pro Val Glu Glu Glu Asp Ala Ala Thr Tyr Tyr Cys Gln His Ser Arg
                85                  90                  95

Glu Ile Pro Tyr Thr Phe Gly Gly Gly Thr Lys Leu Glu Ile Thr Arg
            100                 105                 110

```
<210> SEQ ID NO 54
<211> LENGTH: 17
<212> TYPE: DNA
<213> ORGANISM: Artificial Sequence
<220> FEATURE:
<223> OTHER INFORMATION: forward primer

<400> SEQUENCE: 54
ccactgctgc tgattag                                                    17

<210> SEQ ID NO 55
<211> LENGTH: 18
<212> TYPE: DNA
<213> ORGANISM: Artificial Sequence
<220> FEATURE:
<223> OTHER INFORMATION: reverse primer

<400> SEQUENCE: 55
caatgccttc tcttgtcc                                                   18

<210> SEQ ID NO 56
<211> LENGTH: 8
<212> TYPE: PRT
<213> ORGANISM: Unknown
<220> FEATURE:
<223> OTHER INFORMATION: Viral M1 peptide

<400> SEQUENCE: 56
```

Gly Ile Leu Gly Val Phe Thr Leu
1               5

```
<210> SEQ ID NO 57
<211> LENGTH: 396
<212> TYPE: DNA
<213> ORGANISM: Artificial Sequence
<220> FEATURE:
<223> OTHER INFORMATION: synthetic construct

<400> SEQUENCE: 57
atggagacag acacactcct gttatgggta ctgctgctct gggttccagg ttccactggt    60
```

```
gacattgtgc tgacacagtc tcctgcttcc ttagctgtat ctctggggca gagggccacc      120
atctcatgca gggccagcaa aagtgtcagt acatctggct atagtttat gcactggtat       180 caacagaaac caggacagcc acccaaactc ctcatctatc ttgcatccaa cctagaatct      240
ggggtccctg ccaggttcag tggcagtggg tctgggacag acttcaccct caacatccat     300
cctgtggagg aggaggatgc tgcaacctat tactgtcagc acagtaggga ggttccgtgg     360
acgttcggtg gaggcaccaa gctggaaatc aaacgg                               396
```

<210> SEQ ID NO 58
<211> LENGTH: 411
<212> TYPE: DNA
<213> ORGANISM: Artificial Sequence
<220> FEATURE:
<223> OTHER INFORMATION: synthetic construct

<400> SEQUENCE: 58

```
atggcttggg tgtggacctt gctattcctg atggcagctg cccaaagtgc ccaagcacag      60
atccagttgg tgcagtctgg acctgaggtg aagaagcctg agagacagt caagatctcc      120 tgcaaggctt ctgggtatac cttcacaaac tatggaatga actgggtgaa gcaggctcca     180
ggaaagggtt taaagtggat gggctggata aacacctaca ctggagagcc aacatatgct     240
gatgccttca agggacggtt tgccttctct ttggaaacct ctgccagcac tgcctatttg     300
cagatcaaca acctcaaaaa tgaggacacg gctacatatt tctgtgcaag agactacggc     360
gactatggta tggactactg gggtcaagga acctcagtca ccgtctcctc a              411
```

<210> SEQ ID NO 59
<211> LENGTH: 396
<212> TYPE: DNA
<213> ORGANISM: Artificial Sequence
<220> FEATURE:
<223> OTHER INFORMATION: synthetic construct

<400> SEQUENCE: 59

```
atggagacag acacactcct gttatgggta ctgctgctct gggttccagg ttccactggt      60
gacattgtgc tgacacagtc tcctgcttcc ttaactgtat ctctggggca gaagaccacc     120
atctcatgca gggccagcaa gagtgtcagt acatctggct atagtttat gcactggtac      180 caactgaaac caggacagtc acccaaactc ctcatctatc ttgcgtccaa cctaccatct     240
ggggtccctg ccaggttcag tggcagtggg tctgggacag acttcaccct caaaatccat     300
cctgtggagg aggaggatgc tgcaacctat tactgtcagc acagtaggga gattccgtac    360
acgttcggag gggggaccaa gctggaaata acacgg                               396
```

<210> SEQ ID NO 60
<211> LENGTH: 411
<212> TYPE: DNA
<213> ORGANISM: Artificial Sequence
<220> FEATURE:
<223> OTHER INFORMATION: synthetic construct

<400> SEQUENCE: 60

```
atggaatgga cctgggtctt tctcttcctc ctgtcagtaa ctgcagatgt ccaatcccag      60
gttcagctgc aacagtctgg aactgagctg atgacgcctg gggcctcagt gacgatgtcc    120
tgcaagactt ctggctacac attcagtacc tactggatag agtgggtaaa acagaggcct    180
ggacatggcc ttgagtggat tggagaaatt ttacctggaa gtggttatac tgactacaat    240
gagaagttca aggccaaggc cacattcact gcagatacat cctccaacac agcctacatg    300
```

```
caactcagca gcctggcatc tgaggactct gccgtctatt actgtgcaag atgggatagg    360
ctctatgcta tggactactg gggtcaagga acctcagtca ccgtctcctc a            411
```